Figure 1:
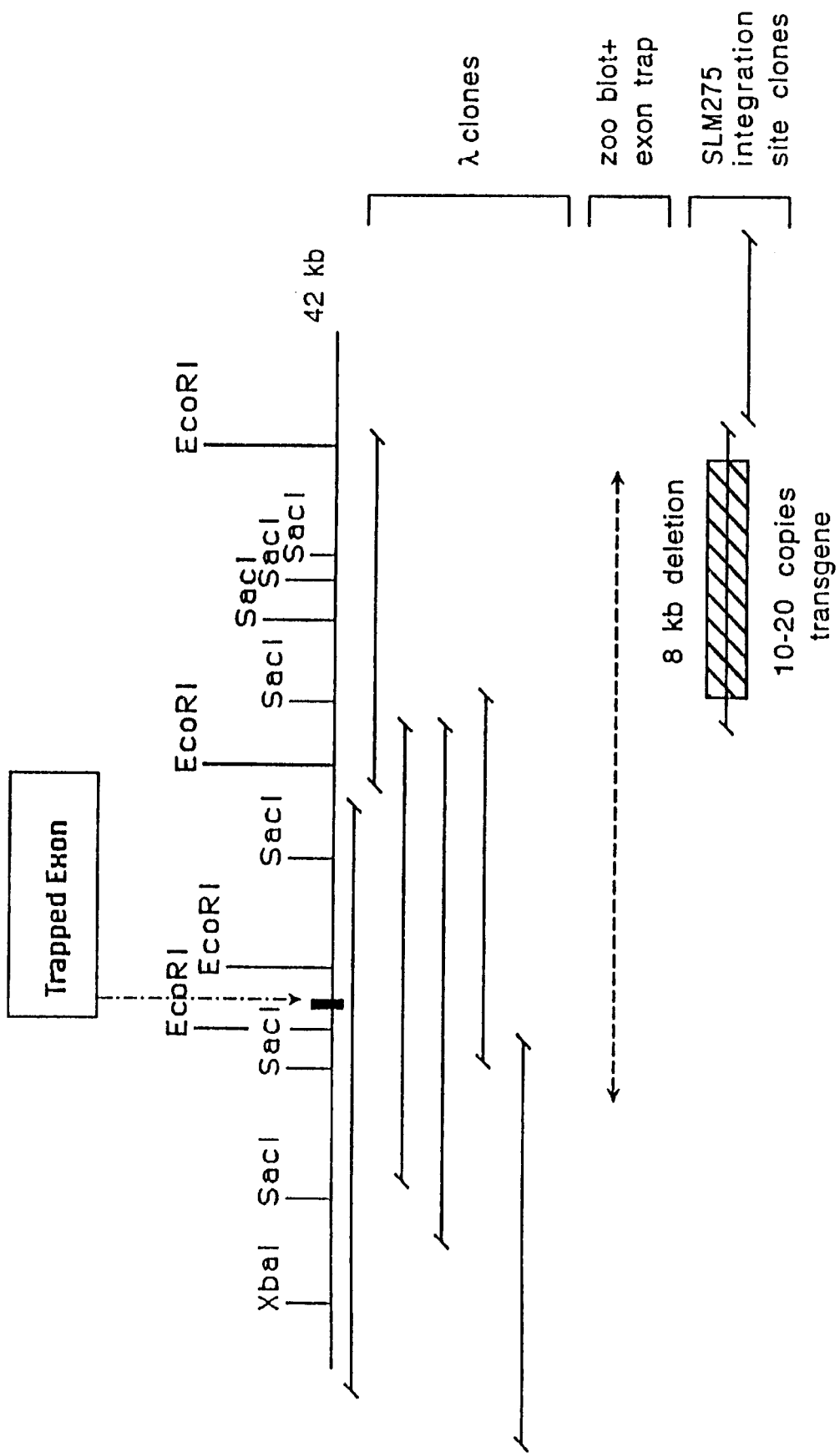

United States Patent [19]
Quertermous et al.

[11] Patent Number: 5,874,562
[45] Date of Patent: Feb. 23, 1999

[54] NUCLEIC ACID ENCODING DEVELOPMENTALLY-REGULATED ENDOTHELIAL CELL LOCUS-1

[75] Inventors: Thomas Quertermous, Nashville; Bridgid Hogan, Brentwood, both of Tenn.; H. Ralph Snodgrass, Powell; Thomas Joel Zupancic, Worthington, both of Ohio

[73] Assignees: Progenitor, Inc., Menlo Park, Calif.; Vanderbilt University, Nashville, Tenn.

[21] Appl. No.: 480,229

[22] Filed: Jun. 7, 1995

[51] Int. Cl.⁶ .............................. C12N 15/12; C12N 5/10; C12N 15/63
[52] U.S. Cl. ...................... 536/23.5; 536/23.4; 435/69.1; 435/320.1; 435/325; 435/252.3; 435/254.11; 530/350
[58] Field of Search .................................. 435/69.1, 325, 435/410, 25.3, 254.11, 320.1; 536/23.4, 23.5; 530/350

[56] References Cited

U.S. PATENT DOCUMENTS

| | | | |
|---|---|---|---|
| 4,868,112 | 9/1989 | Toole, Jr. et al. | 435/68 |
| 5,096,825 | 3/1992 | Barr et al. | 435/255 |
| 5,270,170 | 12/1993 | Schatz et al. | 435/7.37 |
| 5,505,955 | 4/1996 | Peterson et al. | 424/439 |
| 5,506,107 | 4/1996 | Cunningham et al. | 435/7.21 |
| 5,508,199 | 4/1996 | Gonzalez et al. | 435/320.1 |

OTHER PUBLICATIONS

Anderson, 1990, "Adhesion molecules and animal development," *Experientia* 46:2–13.

Brooks et al., 1994, "Integrin $\alpha_v\beta_3$ Antagonists Promote Tumor Regression by Inducing Apoptosis of Angiogenic Blood Vessels," *Cell* 79:1157–1164.

Couso and Arias, 1994, "Notch is Required for wingless Signaling in the Epidermis of Drosophila," *Cell* 79:259–272.

Crowley et al., 1985, "Phenocopy of Discoidin I–Minus Mutants by Antisense Transformation in Dictyostelium," *Cell* 43:633–641.

Fortini and Artavanis–Tsakonas, 1994, "The Suppressor of Hairless Protein Participates in Notch Receptor Signaling," *Cell* 79:273–282.

Fukuzawa and Ochiai, 1988, "Monoclonal Antibodies against Discoidin I and Discoidin II of the Cellular Slime Mold, *Dictyostelium discoideum*," *J. Biochem* 103:884–888.

Henderon et al., 1994, "lag–2 may encode a signaling ligand for the GLP–1 and LIN–12 receptors of *C. elegans*," *Development* 120:2913–2924.

Hynes, 1992, "Integrins: Verstility, Modulation, and Signaling in Cell Adhesion," *Cell* 69:11–25.

Johnson et al., 1993, "A receptor tyrosine kinase found in breast carcinoma cells has an extracellular discoidin I–like domain," *Proc. Natl. Acad. Sci. U.S.A.* 90:5677–5681.

Kane and Davie, 1986, "Cloning of a cDNA coding for human factor V, a blood coagulation factor homologous to factor VIII and ceruloplasmin," *Proc. Natl. Acad. Sci. U.S.A.* 83:6800–6804.

Kronmiller et al., 1991, "EGF Antisense Oligodeoxynucleotides Block Murine Odontogenesis in Vitro," *Dev. Biol.* 147:485–488.

(List continued on next page.)

*Primary Examiner*—Lorraine Spector
*Assistant Examiner*—Claire M. Kaufman
*Attorney, Agent, or Firm*—Pennie & Edmonds LLP

[57] ABSTRACT

The present invention relates to a member of a novel gene family referred to as developmentally-regulated endothelial cell locus-1 (del-1). In particular, the invention relates to del-1 nucleotide sequence, Del-1 amino acid sequence, methods of expressing a functional gene product, and methods of using the gene product.

41 Claims, 21 Drawing Sheets

OTHER PUBLICATIONS

Larocca et al., 1991, "A $M_r$ 46,000 Human Milk Fat Globule Protein That Is Highly Expressed in Human Breast Tumors Contains Factor VIII–like Domains," *Cancer Res.* 51:4994–4998.

Main et al, 1992, "The Three–Dimensional Structure of the Tenth Type III Module of Fibronectin: An Insight into RGD–Mediated Interactions," *Cell* 71:671–678.

Orsini et al., 1991, "Radioimmunoassay of Epidermal Growth Factor in Human Saliva and Gastric Juice," *Clinical Biochem.* 24:135–141.

Rebay et al., 1991, "Specifc EGF Repeats of Notch Mediate Interactions with Delta and Serrate: Implications for Notch as a Multifunctional Receptor," *Cell* 67:687–699.

Stubbs et al., 1990, "cDNA cloning of a mouse mammary epithelial cell surface protein reveals the existence of epidermal growth factor–like domains linked to factor VIII–like sequences," *Proc. Natl. Acad. Sci. U.S.A.* 87:8417–8421.

Hillier et al., GenBank Accession Number R56339 (accessed Dec. 18, 1997), May 23, 1995.

Reddy et al., GenBank Accession Number T09857 (accessed Dec. 18, 1997), Nov. 29, 1993.

Familari et al., GenBank Accession Number L14608 (accessed Dec. 18, 1997), Jul. 14, 1993.

Dumont et al., The endothelial–specific receptor tyrosine kinase, tek, is a member of a new subfamily of receptors, Oncogene 8(5):1293–1301, May 1993.

| | | | | | |
|---|---|---|---|---|---|
| m-dell | DLLVPTKVTG | LTTQG--AKD | FGDVLFVGSY | KLAYSNDGEH | WMVHQDEKQR |
| h-MFG | DLGSSKEVTG | ITTQG--ARN | FGSVQFVASY | KVAYSNDSAN | WTEYQDPRTG |
| h-FV | DLLKIKKITTA | TTTQG--CKS | LSSEMYVKSY | TTGYSEQGVE | WKPYRLKSSM |
| m-FV111 | DLQKTMKVTG | TTTQG--VKS | LFTSMFVKEF | LISSSQDGHH | WT--QILYNG |
| X-A5b1 | DLENLRFVSG | LGTQGAISKE | TKKKYFVKSY | KVDISSNGED | WI--TLKDGN |
| X-A5b2 | DLAEEKIVRG | VITQG--GKH | KENKVFMRKF | KIGYSNNGTE | WEMIMDSSKN |
| dis-1 | GCEVPRTEMC | VALQG---RG | -DADQWTSY | KIRYSLDNVS | WF-----EYR |
| CONSENSUS | DL......VTG | TTTQG--.KA | .....FV.SY | KT.YS.DG.. | W.......... |

| | | | | | |
|---|---|---|---|---|---|
| m-dell | KDKVFQGNFD | NDTHRKNVID | PGTYARFIRI | LPL-- |
| h-MFG | SSKVFQGNLD | NNSHKKNIFE | KPEMARYVRV | LPL-- |
| h-FV | VDKIFEGNITN | TKGHVKNFEN | PPIISRFIRV | IPK-- |
| m-FV111 | KVKVECGNQD | SSTPMMASED | PPELTR---- | ---- |
| X-A5b1 | KHLVFTGNITD | ATEVVYRPES | KEVIITRFVRL | RPVTW |
| X-A5b2 | KPKTEEGNTN | YDIPELRTF- | APTITGFIRI | IP--- |
| dis-1 | NGAAITGVTD | RNTVVNPFFD | TPIRARSIAI | HPLT- |
| CONSENSUS | K.KVF.GNTD | .I...N.F. | .PT.RF.IR. | .P.-- |

FIG.2

```
        EcoRI       HpaI
        ▼           ▼
        GAATTCCGGT TAACTGAGGA CAAAGGGTAA TGCAGAAGTG ATATTTGATT TCCATTCTCA    60

DraI
                            ▼
        TTCCCAGTGG CCTTGATATT TAAACTGATT CCTGCCACCA GGTCCTTGGG CCACCCTGTC   120

EspBI       SphI
                    ▼           ▼
        CCTGCGTCTC ATATTTCTGC ATGCTGCTTT GTTTGTATAT AGTGCGCTCC TGGCCTCAGG   180

CTCGCTCCCC TCCAGCTCTC GCTTCATTGT TCTCCAAGTC AGAAGCCCCC GCATCCGCCG   240

BssHII
                                                            ▼
        CGCAGCAGCG TGAGCCGTAG TCACTGCTGG CCGCTTCGCC TGCGTGCGCG CACGGAAATC   300

GGGGAGCCAG GAACCCAAGG AGCCGCCGTC CGCCCGCTGT GCCTCTGCTA GACCACTCGC   360

AGCCCCAGCC TCTCTCAAGC GCACCCACCT CCGCGCACCC CAGCTCAGGC GAAGCTGGAG   420

TGAGGGTGAA TCACCCTTTC TCTAGGGCCA CCACTCTTTT ATCGCCCTTC CCAAGATTTG   480

Eco47III           AatII
              ▼                  ▼
        AGAAGCGCTG CGGGAGGAAA GACGTCCTCT TGATCTCTGA CAGGGCGGGG TTTACTGCTG   540

BssHIII
              PstI
              ▼▼
        TCCTGCAGGC GCGCCTCGCC TACTGTGCCC TCCGCTACGA CCCCGGACCA GCCCAGGTCA   600

BspHI
                      ▼
        CGTCCGTGAG AAGGGATCAT GAAGCACTTG GTAGCAGCCT GGCTTTTGGT TGGACTCAGC   660
                              M   K   H   L   V   A   A   W   L   L   V   G   L   S

CTCGGGGTGC CCCAGTTCGG CAAAGGTGAC ATTTGCAACC CGAACCCCTG TGAAAATGGT   720
        L   G   V   P   Q   F   G   K   G   D   I   C   N   P   N   P   C   E   N   G
```

FIG.3A

```
                                                              BspMI
                                                               ▼
GGCATCTGTC TGTCAGGACT GGCTGATGAT TCCTTTTCCT GTGAGTGTCC AGAAGGCTTC  780
 G  I  C  L  S  G  L  A  D  D  S  F  S  C  E  C  P  E  G  F
                                                              BspMI
                                                               ▼
GCAGGTCCGA ACTGCTCTAG TGTTGTGGAG GTTGCATCAG ATGAAGAAAA GCCTACTTCA  840
 A  G  P  N  C  S  S  V  V  E  V  A  S  D  E  E  K  P  T  S

GCAGGTCCCT GCATCCCTAA CCCATGCCAT AACGGAGGAA CCTGTGAGAT AAGCCAAGCC  900
 A  G  P  C  I  P  N  P  H  N  G  G  T  C  E  I  S  E  A

TATCGAGGAG ACACATTCAT AGGCTATGTT TGTAAATGTC CTCGGGGATT TAATGGGATT  960
 Y  R  G  D  T  F  I  G  Y  V  C  K  C  P  R  G  F  N  G  I

CACTGTCAGC ACAATATAAA TGAATGTGAA GCTGAGCCTT GCAGAAATGG CGGAATATGT 1020
 H  C  Q  H  N  I  N  E  C  E  A  E  P  C  R  N  G  G  I  C

BsmI
                                     ▼
ACCGACCTTG TTGCTAACTA CTCTTGTGAA TGCCCAGGAG AATTTATGGG ACGAAATTGT 1080
 T  D  L  V  A  N  Y  S  C  E  C  P  G  E  F  M  G  R  N  C

CAATATAAAT GCTCTGGGCA CTTGGGAATC GAAGGTGGGA TCATATCTAA TCAGCAAATC 1140
 Q  Y  K  C  S  G  H  L  G  I  E  G  G  I  I  S  N  Q  Q  I

SacI
              EcI136II
                ▼▼
ACAGCTTCAT CTAATCACCG AGCTCTTTTT GGACTCCAGA AGTGGTATCC CTACTATGCT 1200
 T  A  S  S  N  H  R  A  L  F  G  L  Q  K  W  Y  P  Y  Y  A

NcoI
                                                              MscI
                                        PvuII                 BalI
                                          ▼                    ▼▼
CGACTTAATA AGAAGGGCCT TATAAATGCC TGGACAGCTG CTGAAAATGA CAGATGGCCA 1260
 R  L  N  K  K  G  L  I  N  A  W  T  A  A  E  N  D  R  W  P

TGGATTCAGA TAAATTTGCA AAGAAAAATG AGAGTCACTG GTGTTATTAC CCAAGGAGCA 1320
 W  I  Q  I  N  L  Q  R  K  M  R  V  T  G  V  I  T  Q  G  A

AAAAGGATTG GAAGCCCAGA GTACATAAAA TCCTACAAAA TTGCCTACAG CAATGACGGG 1380
 K  R  I  G  S  P  E  Y  I  K  S  Y  K  I  A  Y  S  N  D  G
```

FIG.3B

```
                    BbsI                        EarI
                     ▼                           ▼
         AAGACCTGGG CAATGTACAA AGTAAAAGGC ACCAATGAAG AGATGGTCTT TCGTGGAAAT 1440
          K  T  W   A  M  Y  K  V  K  G   T  N  E  E  M  V  F   R  G  N

NdeI
                               ▼
         GTTGATAACA ACACACCATA TGCTAATTCT TTCACACCCC CAATCAAAGC TCAGTATGTA 1500
          V  D  N   N  T  P  Y  A  N  S   F  T  P  P  I  K  A   Q  Y  V

AGACTCTACC CCCAAATTTG TCGAAGGCAT TGTACTTTAA GAATGGAACT TCTTGGCTGT 1560
          R  L  Y   P  Q  I  C  R  R  H   C  T  L  R  M  E  L   L  G  C

SacI
            Ecl136II
              ▼▼
         GAGCTCTCAG GCTGTTCAGA ACCTTTGGGG ATGAAATCAG GCATATACA  AGACTACCAG 1620
          E  L  S   G  C  S  E  P  L  G   M  K  S  G  H  I  Q   D  Y  Q

BbsI
                     ▼
         ATCACTGCCT CCAGCGTCTT CAGAACACTC AACATGGACA TGTTTACTTG GAACCAAGG  1680
          I  T  A   S  S  V  F  R  T  L   N  M  D  M  F  T  W   E  P  R

AAAGCCAGGC TGGACAAGCA AGGCAAAGTA AATGCCTGGA CTTCCGGCCA TAACGACCAG 1740
          K  A  R   L  D  K  Q  G  K  V   N  A  W  T  S  G  H   N  D  Q

TCACAATGGT TACAGGTTGA TCTTCTTGTC CCTACTAAGG TGACAGGCAT CATTACACAA 1800
          S  Q  W   L  Q  V  D  L  L  V   P  T  K  V  T  G  I   I  T  Q

PmlI
                               ▼
         GGAGCTAAAG ATTTTGGTCA CGTGCAGTTT GTTGGGTCAT ACAAACTAGC TTACAGCAAT 1860
          G  A  K   D  F  G  H  V  Q  F   V  G  S  Y  K  L  A   Y  S  N

ApaLI
                           ▼
         GATGGAGAAC ACTGGATGGT GCACCAGGAT GAAAAACAGA GGAAAGACAA GGTTTTTCAA 1920
          D  G  E   H  W  M  V  H  Q  D   E  K  Q  R  K  D  K   V  F  Q

GGCAATTTTG ACAATGACAC TCACAGGAAA AATGTCATCG ACCCTCCCAT CTATGCACGA 1980
          G  N  F   D  N  D  T  H  R  K   N  V  I  D  P  P  I   Y  A  R
```

FIG.3C

```
TTCATAAGAA TCCTTCCTTG GTCCTGGTAT GGAAGGATCA CTCTGCCGTC AGAGCTGCTG 2040
 F  I  R  I   L  P  W   S  W  Y   G  R  I  T   L  R  S   E  L  L

Fsp I
           ▼
GGCTGCGCAG AGGAGGAATG AAGTGCGGGG CCGCACATCC CACAATGCTT TTCTTTATTT 2100
 G  C  A   E  E  E

TCCTATAAGT ATCTCCACGA AATGAACTGT GTGAAGCTGA TGGAAACTGC ATTTGTTTTT 2160

Hind III
                                                      ▼
TTCAAAGTGT TCAAATTATG GTAGGCTACT GACTGTCTTT TTAGGAGTTC TAAGCTTGCC 2220

TTTTTAATAA TTTAATTTGG TTTCCTTTGC TCAACTCTCT TATGTAATAT CACACTGTCT 2280

Ear I
                ▼
GTGAGTTACT CTTCTTGTTC TCT                                    2303
```

FIG. 3D

```
                  9              18              27              36              45              54
5' TCT CTT TAG TCA CCA CTC TCG CCC TCT CCA AGA ATT TGT TTA ACA AAG GCG TGA
   --- --- --- --- --- --- --- --- --- --- --- --- --- --- --- --- --- ---
    S   L   *   S   P   L   S   P   S   P   R   I   C   L   T   K   R   *
                 63              72              81              90              99             108
   GGA AAG AGA ACG TCT TCT TGA ATT CTT TAG TAG GGG CGG AGT CTG CTG CTG CCC
   --- --- --- --- --- --- --- --- --- --- --- --- --- --- --- --- --- ---
    G   K   R   T   S   S   *   I   L   *   *   G   R   S   L   L   L   P
                117             126             135             144             153             162
   TGC GCT GCC ACC TCG GCT ACA CTG CCC TCC GCG ACG ACC CCT GAC CAG CCG GGG
   --- --- --- --- --- --- --- --- --- --- --- --- --- --- --- --- --- ---
    C   A   A   T   S   A   T   L   P   S   A   T   T   P   D   Q   P   G
                171             180             189             198             207             216
   TCA CGT CCG GGA GAC GGG ATC ATG AAG CGC TCG GTA GCC GTC TGG CTC TTG GTC
   --- --- --- --- --- --- --- --- --- --- --- --- --- --- --- --- --- ---
    S   R   P   G   D   G   I   M   K   R   S   V   A   V   W   L   L   V
                225             234             243             252             261             270
   GGG CTC AGC CTC GGT GTC CCC CAG TTC GGC AAA GGT GAT ATT TGT GAT CCC AAT
   --- --- --- --- --- --- --- --- --- --- --- --- --- --- --- --- --- ---
    G   L   S   L   G   V   P   Q   F   G   K   G   D   I   C   D   P   N
                279             288             297             306             315             324
   CCA TGT GAA AAT GGA GGT ATC TGT TTG CCA GGA TTG CGT GTC GGC TCC TTT TCC
   --- --- --- --- --- --- --- --- --- --- --- --- --- --- --- --- --- ---
    P   C   E   N   G   G   I   C   L   P   G   L   A   V   G   S   F   S
                333             342             351             360             369             378
   TGT GAG TGT CCA GAT GGC TTC ACA GAC CCC AAG TGT TCT AGT GTT GTG GAG GTT
   --- --- --- --- --- --- --- --- --- --- --- --- --- --- --- --- --- ---
    C   E   C   P   D   G   F   T   D   P   N   C   S   S   V   V   E   V
                387             396             405             414             423             432
   GCA TCA GAT GAA GAA GAA CCA ACT TCA GCA GGT CCC TGC ACT CCT AAT CCA TGC
   --- --- --- --- --- --- --- --- --- --- --- --- --- --- --- --- --- ---
    A   S   D   E   E   E   P   T   S   A   G   P   C   T   P   N   P   C
                441             450             459             468             477             486
   CAT AAT GGA GGA ACC TGT GAA ATA AGT GAA GCA TAC CGA GGG GAT ACA TTC ATA
   --- --- --- --- --- --- --- --- --- --- --- --- --- --- --- --- --- ---
    H   N   G   G   T   C   E   I   S   E   A   Y   R   G   D   T   F   I
                495             504             513             522             531             540
   GGC TAT GTT TGT AAA TGT CCC CGA GGA TTT AAT GGG ATT CAC TGT CAG CAC AAC
   --- --- --- --- --- --- --- --- --- --- --- --- --- --- --- --- --- ---
    G   Y   V   C   K   C   P   R   G   F   N   G   I   H   C   Q   H   N
                549             558             567             576             585             594
   ATA AAT GAA TGC GAA GTT GAG CCT TGC AAA AAT GGT GGA ATA TGT ACA GAT CTT
   --- --- --- --- --- --- --- --- --- --- --- --- --- --- --- --- --- ---
    I   N   E   C   E   V   E   P   C   K   N   G   G   I   C   T   D   L
                603             612             621             630             639             648
   GTT GCT AAC TAT TCC TGT GAG TGC CCA GGC GAA TTT ATG GGA AGA AAT TGT CAA
   --- --- --- --- --- --- --- --- --- --- --- --- --- --- --- --- --- ---
    V   A   N   Y   S   C   E   C   P   G   E   F   M   G   R   N   C   Q
```

FIG. 4A

```
              657           666           675           684           693           702
      TAC AAA TGC TCA GGC CCA CTG GGA ATT GAA GGT GGA ATT ATA TCA AAC CAG CAA
      --- --- --- --- --- --- --- --- --- --- --- --- --- --- --- --- --- ---
       Y   K   C   S   G   P   L   G   I   E   G   G   I   I   S   N   Q   Q
              711           720           729           738           747           756
      ATC ACA GCT TCC TCT ACT CAC CGA GCT CTT TTT GGA CTC CAA AAA TGG TAT CCC
      --- --- --- --- --- --- --- --- --- --- --- --- --- --- --- --- --- ---
       I   T   A   S   S   T   H   R   A   L   F   G   L   Q   K   W   Y   P
              765           774           783           792           801           810
      TAC TAT GCA CGT CTT AAT AAG AAG GGG CTT ATA AAT GCG TGG ACA GCT GCA GAA
      --- --- --- --- --- --- --- --- --- --- --- --- --- --- --- --- --- ---
       Y   Y   A   R   L   N   K   K   G   L   I   N   A   W   T   A   A   E
              819           828           837           846           855           864
      AAT GAC AGA TGG AAC CGG TGG ATT CAG ATA AAT TTG CAA AGA AAA ATG AGA GTT
      --- --- --- --- --- --- --- --- --- --- --- --- --- --- --- --- --- ---
       N   D   R   W   N   R   W   I   Q   I   N   L   Q   R   K   M   R   V
              873           882           891           900           909           918
      ACT GGT GTG ATT ACC CAA GGG GCC AAG AGG ATT GGA AGC CCA GAG TAT ATA AAA
      --- --- --- --- --- --- --- --- --- --- --- --- --- --- --- --- --- ---
       T   G   V   I   T   Q   G   A   K   R   I   G   S   P   E   Y   I   K
              927           936           945           954           963           972
      TTC TAC AAA ATT GCC TAC AGT AAT GAT GGA AAG ACT TGG GCA ATG TAC AAA GTG
      --- --- --- --- --- --- --- --- --- --- --- --- --- --- --- --- --- ---
       F   Y   K   I   A   Y   S   N   D   G   K   T   W   A   M   Y   K   V
              981           990           999          1008          1017          1026
      AAA GGC ACC AAT GAA GAC ATG GTG TTT CGT GGA AAC ATT GAT AAC AAC ACT CCA
      --- --- --- --- --- --- --- --- --- --- --- --- --- --- --- --- --- ---
       K   G   T   N   E   D   M   V   F   R   G   N   I   D   N   N   T   P
             1035          1044          1053          1062          1071          1080
      TAT GCT AAC TCT TTC ACA CCC CCC ATA AAA GCT CAG TAT GTA AGA CTC TAT CCC
      --- --- --- --- --- --- --- --- --- --- --- --- --- --- --- --- --- ---
       Y   A   N   S   F   T   P   P   I   K   A   Q   Y   V   R   L   Y   P
             1089          1098          1107          1116          1125          1134
      CAA GTT TGT CGA AGA CAT TGC ACT TTG CGA ATG GAA CTT CTT GGC TGT GAA CTG
      --- --- --- --- --- --- --- --- --- --- --- --- --- --- --- --- --- ---
       Q   V   C   R   R   H   C   T   L   R   M   E   L   L   G   C   E   L
             1143          1152          1161          1170          1179          1188
      TCG GGT TGT TCT GAG CCT CTG GGT ATG AAA TCA GGA CAT ATA CAA GAC TAT CAG
      --- --- --- --- --- --- --- --- --- --- --- --- --- --- --- --- --- ---
       S   G   C   S   E   P   L   G   M   K   S   G   H   I   Q   D   Y   Q
             1197          1206          1215          1224          1233          1242
      ATC ACT GCC TCC AGC ATC TTC AGA ACG CTC AAC ATG GAC ATG TTC ACT TGG GAA
      --- --- --- --- --- --- --- --- --- --- --- --- --- --- --- --- --- ---
       I   T   A   S   S   I   F   R   T   L   N   M   D   M   F   T   W   E
             1251          1260          1269          1278          1287          1296
      CCA AGG AAA GCT CGG CTG GAC AAG CAA GGC AAA GTG AAT GCC TGG ACC TCT GGC
      --- --- --- --- --- --- --- --- --- --- --- --- --- --- --- --- --- ---
       P   R   K   A   R   L   D   K   Q   G   K   V   N   A   W   T   S   G
```

FIG. 4B

```
      1305        1314        1323        1332        1341        1350
CAC AAT GAC CAG TCA CAA TGG TTA CAG GTG GAT CTT CTT GTT CCA ACC AAA GTG
--- --- --- --- --- --- --- --- --- --- --- --- --- --- --- --- --- ---
 H   N   D   Q   S   Q   W   L   Q   V   D   L   L   V   P   T   K   V
      1359        1368        1377        1386        1395        1404
ACT GGC ATC ATT ACA CAA GGA GCT AAA GAT TTT GGT CAT GTA CAG TTT GTT GGC
--- --- --- --- --- --- --- --- --- --- --- --- --- --- --- --- --- ---
 T   G   I   I   T   Q   G   A   K   D   F   G   H   V   Q   F   V   G
      1413        1422        1431        1440        1449        1458
TCC TAC AAA CTG GCT TAC AGC AAT GAT GGA GAA CAC TGG ACT GTA TAC CAG GAT
--- --- --- --- --- --- --- --- --- --- --- --- --- --- --- --- --- ---
 S   Y   K   L   A   Y   S   N   D   G   E   H   W   T   V   Y   Q   D
      1467        1476        1485        1494        1503        1512
GAA AAG CAA AGA AAA GAT AAG GTT TTC CAG GGA AAT TTT GAC AAT GAC ACT CAC
--- --- --- --- --- --- --- --- --- --- --- --- --- --- --- --- --- ---
 E   K   Q   R   K   D   K   V   F   Q   G   N   F   D   N   D   T   H
      1521        1530        1539        1548        1557        1566
AGA AAA AAT GTC ATC GAC CCT CCC ATC TAT GCA CGA CAC ATA AGA ATC CTT CCT
--- --- --- --- --- --- --- --- --- --- --- --- --- --- --- --- --- ---
 R   K   N   V   I   D   P   P   I   Y   A   R   H   I   R   I   L   P
      1575        1584        1593        1602        1611        1620
TGG TCC TGG TAC GGG AGG ATC ACA TTG GCG TCA GAG CTG CTG GGC TGC ACA GAG
--- --- --- --- --- --- --- --- --- --- --- --- --- --- --- --- --- ---
 W   S   W   Y   G   R   I   T   L   A   S   E   L   L   G   C   T   E
      1629        1638        1647        1656        1665        1674
GAG GAA TGA GGG GAG GCT ACA TTT CAC AAC CGT CTT CCC TAT TTG GGT AAA AGT
--- --- --- --- --- --- --- --- --- --- --- --- --- --- --- --- --- ---
 E   E   *   G   E   A   T   F   H   N   R   L   P   Y   L   G   K   S
      1683        1692        1701        1710        1719        1728
ATC TCC ATG GAA TGA ACT GTG TAA AAT CTG TAG GAA ACT GAA TGG TTT TTT TTT
--- --- --- --- --- --- --- --- --- --- --- --- --- --- --- --- --- ---
 I   S   M   E   *   T   V   *   N   L   *   E   T   E   W   F   F   F
      1737        1746        1755        1764        1773
TTT TCA TGA AAA AGT GGT CAA ATT ATG GTA GGC AAC TAA CGG TGT TTT TAC C 3'
--- --- --- --- --- --- --- --- --- --- --- --- --- --- --- --- --- -
 F   S   *   K   S   G   Q   I   M   V   G   N   *   R   C   F   Y
```

FIG. 4C

```
         10         20         30         40         50         60
GACAGATGGC CATGGATTCA GATAAATTTG CAAAGAAAAA TGAGAGTCAC TGGTGTTATT
         70         80         90        100        110        120
ACCCAAGGAG CAAAAAGGAT TGGAAGCCCA GAGTACATAA AATCCTACAA AATTGCCTAC
        130        140        150        160        170        180
AGCAATGACG GGAAGACCTG GGCAATGTAC AAAGTAAAAG GCACCAATGA AGAGATGGTC
        190        200        210        220        230        240
TTTCGTGGAA ATGTTGATAA CAACACACCA TATGCTAATT CTTTCACACC CCCAATCAAA
        250        260        270        280        290        300
GCTCAGTATG TAAGACTCTA CCCCCAAATT TGTCGAAGGC ATTGTACTTT AAGAATGGAA
        310        320        330        340        350        360
CTTCTTGGCT GTGAGCTC.. .......... .......... .......... ..........
```

FIG. 5

```
       1         10        20        30        40        50        60        70
N- CSTQLGMEGGAIADSQISASYVYMGFMGLQRWGPELARLYRTGIVNAWHASNYD-SKPWIQVNLLRKMRV
   **  ** ***  **         ***    *** *      *           * ***  **  ******
N- CSGPLGIEGGIISNQQITASSTHRALFGLQKWYPYYARLNKKGLINAWTAAENDRWNRWIQINLQRKMRV
   1         10        20        30        40        50        60        70

71        80        90        100       110       120       130       140
   SGVMTQGASRAGRAEYLKTFKVAYSLDG-RKFEFIQDESGGDKEFLGNLDNNSLKVNMFNPTLEAQYIRL
   ** **** *  ** *  *  * *** **    *  ** *      * ***   *      ***  ** **
   TGVITQGAKRIGSPEYIKFYKIAYSNDGKTWAMYKVKGTNEDMVFRGNIDNNTPYANSFTPPIKAQYVRL
   71        80        90        100       110       120       130       140

141       150       160       170       180       190       200       210
   YPVSCHRGCTLRFELLGCELHGCLEPLGLKNNTIPDSQMSASSSYKTWNLRAFGWYPHLGRLDNQGKINA
   ** * **** ********  ** *   *** *      ***   *  **  *** *** *** *** **
   YPQVCRRHCTLRMELLGCELSGCSEPLGMKSGHIQDYQITASSIFRTLNMDMFTWEPRKARLDKQGKVNA
   141       150       160       170       180       190       200       210

211       220       230       240       250       260       270       280
   WTAQSNSAKEWLQVDLGTQRQVTGIITQGARDFGHIQYVESYKVAHSDDGVQWTVY--EEQGSSKVFQGN
   **  *   ****          ***********  *** * * **    * *** *    ***  *****
   WTSGHNDQSQWLQVXLLVPTKVTGIITQGAKDXGHVQFVGSYKLAYSNDGEHWTVXQDEKQRKDKVXQGN
   211       220       230       240       250       260       270       280

281       290       300       310       320
   LDNNSHKKNIFEKPFMARYVRVLPVSWHNRITLRLELLGC* -C
   **  *  **    **  ** ** ****  *    *****
   FDNDTHRKNVIDPPIYARHIRILPWSWYGRITLASELLGCT -C
   281       290       300       310       320
```

1) CDPNPCENGGICLPGLAVG-----SFSCECPDGFTDPNCS SVVEVASDEEEPTSAGP
2) CTPNPCHNGGTCEISEAYRGDTFIGYVCKCPRGFNGIHCQ HNINE
3) CEVEPCKNGGICTDLVA-------NYSCECPGEFMGRNCQ YK

CONCENSUS  C---PC-NGG-C--------------Y-C-C--GY-G--C-
EGF DOMAIN                                F     F

FIG.9

```
              9              18             27             36             45             54
5' -GT CAT ATT TGT GAT CCC AAT CCA TGT GAA AAT GGA GGT ATC TGT TTG CCA GGA
   --- --- --- --- --- --- --- --- --- --- --- --- --- --- --- --- --- ---
    X   D   I   C   D   P   N   P   C   E   N   G   G   I   C   L   P   G
              63             72             81             90             99            108
   TTG GCT GTA GGT TCC TTT TCC TGT GAG TGT CCA GAT GGC TTC ACA GAC CCC AAC
   --- --- --- --- --- --- --- --- --- --- --- --- --- --- --- --- --- ---
    L   A   V   G   S   F   S   C   E   C   P   D   G   F   T   D   P   N
             117            126            135            144            153            162
   TGT TCT AGT GTT GTG GAG GTT GGT CCC TGC ACT CCT AAT CCA TGC CAT AAT GGA
   --- --- --- --- --- --- --- --- --- --- --- --- --- --- --- --- --- ---
    C   S   S   V   V   E   V   G   P   C   T   P   N   P   C   H   N   G
             171            180            189            198            207            216
   GGA ACC TGT GAA ATA AGT GAA GCA TAC CGA GGG GAT ACA TTC ATA GGC TAT GTT
   --- --- --- --- --- --- --- --- --- --- --- --- --- --- --- --- --- ---
    G   T   C   E   I   S   E   A   Y   R   G   D   T   F   I   G   Y   V
             225            234            243            252            216            270
   TGT AAA TGT CCC CGA GGA TTT AAT GGG ATT CAC TGT CAG CAC AAC ATA AAT GAA
   --- --- --- --- --- --- --- --- --- --- --- --- --- --- --- --- --- ---
    C   K   C   P   R   G   F   N   G   I   H   C   Q   H   N   I   N   E
             279            288            297            306
   TGC GAA GTT GAG CCT TGC AAA AAT GGT GGA ATA TGT ACA G 3'
   --- --- --- --- --- --- --- --- --- --- --- -
    C   E   V   E   P   C   K   N   G   G   I   C   T
```

FIG.10

```
            EcoRI                          SacII    ApaI
             ▼                              ▼        ▼
       GAATTCCGGG AGGGAGGGTA GGGGGGCGGG CCGCGGGGGC CCAAAGCCAG CTAGGCTCAG    60

TCTCACACGC GCGCCGCCAC TGTTTGTATA TAGTGCGCTC CTGGCCTCAG CGTCGCTCCC   120

CTCCAGCTCT CGCTTCATTG TTCTCCAAGT CAGAAGCCCC CGCATCCGCC GCGCAGCAGC   180

GTGAGCCGTA GTCACTGCTG GCCGCTTCGC CTGCGTGCGC GCACGGAAAT CGGGGAGCCA   240

GGAACCCAAG GAGCCGCCGT CCGCCCGCTG TGCCTCTGCT AGACCACTCG CAGCCCCAGC   300

CTCTCTCAAG CGCACCCACC TCCGCGCACC CCAGCTCAGG CGAAGCTGGA GTGAGGGTGA   360
                                                              Eco47III
                                                                 ▼
       ATCACCCTTT CTCTAGGGCC ACCACTCTTT TATCGCCCTT CCCAAGATTT GAGAAGCGCT   420

AatII                                      PstI
                            ▼                                         ▼
       GCGGGAGGAA AGACGTCCTC TTGATCTCTG ACAGGGCGGG GTTTACTGCT GTCCTGCAGG   480

CGCGCCTCGC CTACTGTGCC CTCCGCTACG ACCCCGGACC AGCCCAGGTC ACGTCCGTGA   540

BspHI
             ▼
       GAAGGGATCA TGAAGCACTT GGTAGCAGCC TGGCTTTTGG TTGGACTCAG CCTCGGGGTG   600
                    M  K  H  L  V  A  A  W  L  L  V  G  L  S  L  G  V

CCCCAGTTCG GCAAAGGTGA CATTTGCAAC CCGAACCCCT GTGAAAATGG TGGCATCTGT   660
        P  Q  F  G  K  G  D  I  C  N  P  N  P  C  E  N  G  G  I  C

BspMI
                                              ▼
       CTGTCAGGAC TGGCTGATGA TTCCTTTTCC TGTGAGTGTC CAGAAGGCTT CGCAGGTCCG   720
        L  S  G  L  A  D  D  S  F  S  C  E  C  P  E  G  F  A  G  P
```

FIG.11A

```
                                          BspMI
                                            ▼
AACTGCTCTA GTGTTGTGGA GGTTGCATCA GATGAAGAAA AGCCTACTTC AGCAGGTCCC  780
 N  C  S  S  V  V  E  V  A  S  D  E  E  K  P  T  S  A  G  P

TGCATCCCTA ACCCATGCCA TAACGGAGGA ACCTGTGAGA TAAGCGAAGC CTATCGAGGA  840
 C  I  P  N  P  H  N  G  G  T  C  E  I  S  E  A  Y  R  G

GACACATTCA TAGGCTATGT TTGTAAATGT CCTCGGGGAT TAATGGGAT TCACTGTCAG   900
 D  T  F  I  G  Y  V  C  K  C  P  R  G  F  N  G  I  H  C  Q

CACAATATAA ATGAATGTGA AGCTGAGCCT TGCAGAAAAG GCGGAATATG TACCGACCTT  960
 H  N  I  N  E  C  E  A  E  P  C  R  N  G  I  C  T  D  L

BsmI
                        ▼
GTTGCTAACT ACTCTTGTGA ATGCCCAGGA GAATTTATGG GACGAAATTG TCAATATAAA 1020
 V  A  N  Y  S  C  E  C  P  G  E  F  M  G  R  N  C  Q  Y  K

TGCTCTGGGC ACTTGGGAAT CGAAGGTGGG ATCATATCTA ATCAGCAAAT CACAGCTTCA 1080
 C  S  G  H  L  G  I  E  G  G  I  I  S  N  Q  Q  I  T  A  S

SacI
           EclI36II
            ▼▼
TCTAATCACC GAGCTCTTTT TGGACTCCAG AAGTGGTATC CCTACTATGC TAGACTTAAT 1140
 S  N  H  R  A  L  F  G  L  Q  K  W  Y  P  Y  Y  A  R  L  N

NcoI
                                                          MscI
                              PvuII                        BalI
                                ▼                          ▼▼
AAGAAGGGCC TTATAAATGC CTGGACAGCT GCTGAAAATG ACAGATGGCC ATGGATTCAG 1200
 K  K  G  L  I  N  A  W  T  A  A  E  N  D  R  W  P  W  I  Q

GTAACAGTGG GATGAGACAA ATCCATTTCC CAAATTATCA GAATCATTAT AGAAGTAGGT 1260
 V  T  V  G

TAGGGAGAAT TGGCTGTGAT TCTTTCTCAT GGTTAAAATG TGATTTAGTT CAGAATTAAC 1320
```

FIG.11B

ATGGTTGGAA ACTCTAAAAA ATGTGGAAAA CAGGAACATT CTATGTCTGA AAATCTGAAA 1380

ATAGCATCAA GATGAAAACA TTCTTTAGTC ATAAATATAC TCTTTTAAGT TATAGTAGAG 1440

BglII
    ▼
AAAAAGATCT TATCATTTCA TAAGTGGACT TTTGGGATAG CATTGGAAAT GTAAATGAAA 1500

SspI
                                  ▼
TAAATACCTA ATTGAAAAAA GTTTATTCTA AAGTGTTAAT ATTTAGCAAC AGATTCAGAG 1560

ACAAGAAAGT AACAATTCAA TCTGTGTATT TTTTGTGAGA AATAGTTTCC CATGTGCAAA 1620

FspI   BspHI                 PstI
       ▼       ▼                 ▼
TATAAAGTGC GCATCATATC ATGATAATAT CCAACTGTCT GCAGAACTCC CTTTCATAAA 1680

TGAGAGAATT TTAATTCATA GTGCCTTATA TCCTCATCAG CCATCTGACT TTACTACAGA 1740

NsiI
                    ▼
AGAAAACAAT GAAATGATGC ATTAAGTGCT TGCTAGAAG AAACATCATA GCAAAGCTGA 1800

XhoI
              HindIII   PaeR7I
              ▼        ▼
TAGCCCACAT TCTGTGCANN NAAGCTTCCA GAGCACTCGA GAAAAAGCAG AAATGAGATG 1860

BclI
                                      ▼
TTTTATGAAA ACCGAAAAGA TAATCTGATT TCTGTGAAAT ATACTTTTGA TCATGTGGTT 1920

CTTTAAGATA GTCACTAACA AGTCATTAGT AGCAGATACC AAATGGGAGA AAATTTCCAG 1980

Bsl1107I
▼
TATACTGAGG GTCAAGGCAG TCATGCTGAA ACTACATGAG GTCAGGAAAG TTTTGAAATA 2040

FIG.11C

AGGTGATTTT GGAAGGATAC CTTCAACTGG CCTAGATTTT CAAGAAACAG TGTAATCAAC 2100

AGCCAAACAT GAGAATCTAG CTAACAGCAT TTAGAAAACC AGAACTAAGA GTGTTACTGG 2160

DraI
           ▼
GGAATTGCAT TTAAATCCAG TATGAGAGTT TGCAAATGCC GTATTCTTCT AAGGGGTTTG 2220

NcoI
           ▼
TGCCACATTT TGTTACCATG GAGTCCTCTG TAAGAACTTT ATTAGATAAA TCATCTTTAC 2280

EcoRI
           ▼
ACTATAATTT GAATAAAAGC CGGAATTC                             2308

FIG. 11D

NUCLEIC ACID ENCODING DEVELOPMENTALLY-REGULATED ENDOTHELIAL CELL LOCUS-1

This invention was made, in part, with government support under HD25580 awarded by the National Institutes of Health. The government has certain rights in the invention.

1. INTRODUCTION

The present invention relates to a member of a novel gene family referred to as developmentally-regulated endothelial cell locus-1 (del-1). In particular, the invention relates to del-1 nucleotide sequence, Del-1 amino acid sequence, methods of expressing a functional gene product, and methods of using the gene product. Since del-1 is expressed in embryonic endothelial cells, it may be useful in regulating endothelial cell function.

2. BACKGROUND OF THE INVENTION

2.1. ENDOTHELIAL CELL BIOLOGY AND BLOOD VESSEL DEVELOPMENT

The endothelium occupies a pivotal position at the interface between the circulating humoral and cellular elements of the blood, and the solid tissues which constitute the various organs. In this unique position, endothelial cells regulate a large number of critical processes. Such processes include leukocyte adherence and transit through the blood vessel wall, local control of blood vessel tone, modulation of the immune response, the balance between thrombosis and thrombolysis, and new blood vessel development (Bevilacqua et al., 1993, *J. Clin. Invest* 91:379–387; Folkman et al., 1987, *Science* 235:442–447; Folkman et al., 1992, J. Biol. Chem. 267:10931–10934; Gimbrone, 1986, Churchill Livingstone, London; Issekutz, 1992, *Curr. Opin. Immunol.* 4:287–293; Janssens et al., 1992, *J. Biol. Chem.* 267:14519–14522; Lamas et al., 1992, *Proc. Natl. Acad. Sci. U.S.A.* 89:6348–6352; Luscher et al., 1992, *Hypertension* 19:117–130; Williams et al., 1992, *Am. Rev. Respir. Dis.* 146:S45–S50; Yanagisawa, et al., 1988, *Nature* 332:411–415).

Endothelial cell dysfunction has been postulated as a central feature of vascular diseases such as hypertension and atherosclerosis. In this context, the ability of the endothelium to synthesize smooth muscle cell mitogens and factors which control smooth muscle contraction has received much attention (Janssens et al., 1992, *J. Biol. Chem.* 267:14519–14522; Lamas et al., 1992, *Proc. Natl. Acad. Sci. U.S.A.* 89:6348–6352; Luscher et al., 1992, *Hypertension* 19:117–130; Raines et al., 1993, *Br. Heart J.* 69:S30–S37; Yanagisawa et al., 1988, *Nature* 332:411–415). The endothelial cell has also become the focus of attention in the study of diseases which are not primarily vascular in nature. Diverse disease processes such as adult respiratory distress syndrome, septic shock, solid tumor formation, tumor cell metastasis, rheumatoid arthritis, and transplant rejection are now understood to be related to normal or aberrant function of the endothelial cell. A rapidly increasing number of pharmacologic agents are being developed whose primary therapeutic action will be to alter endothelial cell function. In addition, recent attention on gene therapy has focused on the endothelial cell (Nabel et al., 1991, *J. Am. Coll. Cardiol.* 17:189B–194B) . Transfer of genes into the endothelial cell may afford a therapeutic strategy for vascular disease, or the endothelium may serve simply as a convenient cellular factory for a missing blood borne factor. Hence, information regarding fundamental processes in the endothelial cell will aid the understanding of disease processes and allow more effective therapeutic strategies.

Studies from a number of laboratories have characterized the ability of the endothelial cell to dramatically alter basic activities in response to cytokines such as tumor necrosis factor (TNF)-alpha. TNF-alpha stimulation induces significant alterations in the production of vasoactive compounds such as nitric oxide and endothelin, increases surface stickiness toward various types of leukocytes, and modulates the expression of both pro- and anti-coagulant factors (Cotran et al., 1990, *J. Am. Soc. Nephrol.* 1:225–235 ; Mantovani et al., 1992, *FASEB J.* 6:2591–2599). In turn, endothelial cells have been shown to be an important source for the production of cytokines and hormones, including interleukin 1, 6 and 8 (Gimbrone et al., 1989, *Science* 246:1601–1603; Locksley et al. 1987, *J. Immunol.* 139:1891–1895; Loppnow et al., 1989, *Lymphokine. Res.* 8:293–299; Warner et al. , 1987, *J. Immunol.* 139:1911–1917).

The ability of endothelial cells to produce granulocyte, granulocyte-macrophage, and macrophage colony stimulating factors has led to speculation that endothelial cells are an important facet of hematopoietic development (Broudy et al., 1987, *J. Immunol.* 139:464–468; Seelentag et al., 1987, *EMBO J.* 6:2261–2265). Early studies have provided the foundation for the cloning of a large number of "endothelial cell-specific" genes. Some of these include ICAM-1, ICAM-2, VCAM-1, ELAM-1, endothelin-1, constitutive endothelial cell nitric oxide synthetase, thrombomodulin, and the thrombin receptor (Bevilacqua et al., 1989, *Science* 243:1160–1165; Jackman et al., 1986, *Proc. Natl. Acad. Sci. U.S.A.* 83:8834–8838; Janssens et al., 1992, *J. Biol. Chem.* 267:14519–14522; Lamas et al., 1992, *Proc. Natl. Acad. Sci. U.S.A.* 89:6348–6352; Osborn et al., 1989, *Cell* 59:1203–1211; Staunton et al., 1989, *Nature* 339:61–64; Staunton et al., 1988, *Cell* 52:925–933; Vu et al, 1991, *Cell* 64:1057–1068; Yanagisawa et al., 1988, *Nature* 332:411–415).

All blood vessels begin their existence as a capillary, composed of only endothelial cells. Much of the molecular research investigating the role of endothelial cells in blood vessel development has focused on this process in the adult organism, in association with pathological conditions. In these situations, new blood vessels are formed by budding and branching of existing vessels. This process, which depends on endothelial cell division, has been termed angiogenesis. Research on this process has focused primarily on small proteins which are growth factors for endothelial cells (Folkman et al., 1987, *Science* 235:442–447; Folkman et al., 1992, *J. Biol. Chem.* 267:10931–10934). Sensitive bioassays for angiogenesis have allowed the characterization of a number of angiogenic factors, from both diseased and normal tissues. Members of the fibroblast growth factor (FGF) family, platelet-derived endothelial cell growth factor, and vascular endothelial cell growth factor (vascular permeability factor), are a few of the angiogenic factors which have been characterized (Folkman et al., 1987, *Science* 235:442–447; Folkman et al., 1992, *J. Biol. Chem.* 267:10931–10934; Ishikawa et al., 1989, *Nature* 338:557–562; Keck et al., 1989, *Science* 246:1309–1312; Leung et al., 1989, *Science* 246:1306–1309).

Such information has provided some insight into the study of blood vessel development in the embryo. Studies linking vascular development to an angiogenic factor have resulted in the work with vascular endothelial cell growth factor (VEGF). VEGF expression has been correlated in a temporal and spatial fashion with blood vessel development in the embryo (Breier et al., 1992, *Development* 114:521–532). A high affinity VEGF receptor, flk-1, has been shown to be expressed on the earliest endothelial cells in a parallel fashion (Millauer et al., 1993, *Cell* 72:835–846).

Blood vessels form by a combination of two primary processes. Some blood vessel growth depends on angiogenesis, in a process very similar to that associated with pathological conditions in the adult. For instance, the central nervous system depends solely on angiogenesis for development of its vascular supply (Noden, 1989, *Am. Rev. Respir. Dis.* 140:1097–1103; Risau et al., 1988, *EMBO J.* 7:959–962). A second process, vasculogenesis, depends on the incorporation of migratory individual endothelial cells (angioblasts) into the developing blood vessel. These angioblasts appear to be components of almost all mesoderm, and are able to migrate in an invasive fashion throughout the embryo (Coffin et al., 1991, *Anat. Rec.* 231:383–395; Noden, 1989, *Am. Rev. Respir. Dis.* 140:1097–1103; Noden, 1991, *Development* 111:867–876). The precise origin of this cell, and the characteristics of its differentiation have not been defined.

Understanding of the molecular basis of endothelial cell differentiation in blood vessel development may allow manipulation of blood vessel growth for therapeutic benefit. The ability to suppress blood vessel growth may also provide therapeutic strategies for diseases such as solid tumors and diabetic retinopathy. On the other hand, diseases such as coronary artery disease may be treated through pharmacologic induction of directed blood vessel growth, through increasing collateral circulation in the coronary vascular bed. Both vascular diseases such as atherosclerosis and hypertension and nonvascular diseases which depend on the endothelial cell will benefit from a better understanding of endothelial cells.

2.2. EPIDERMAL GROWTH FACTOR-LIKE DOMAIN

Epidermal growth factor (EGF) stimulates growth of a variety of cell types. EGF-like domains have been found in a large number of extracellular and membrane bound proteins (Anderson, 1990, *Experientia* 46(1):2; and Doolittle, 1985, *TIBS*, June:233). These proteins include molecules that function as soluble secreted proteins, growth factors, transmembrane signal and receptor molecules, and components of the extracellular matrix (Lawler and Hynes, 1986, *J. Cell. Biol.* 103:1635; Durkin et al., 1988, *J. Cell Biol.* 107:2749; Wu et al., 1990, *Gene* 86:275; Bisgrove and Raff, 1993, *Develop. Biol.* 157:526;).

In many cases, multiple tandem repeats of a characteristic 40 amino acid long, 6 cysteine-containing sequence are observed (Anderson, 1990, *Experientia* 46(12):2). EGF-like domains are homologous to the peptide growth factor EGF which consists of a single copy of the standard EGF domain. These domains have been highly conserved in evolution, being found in species as diverse as nematodes, Drosophila, sea urchins, and vertebrates.

The EGF molecule and the closely related transforming growth factor (TGF) alpha induce cell proliferation by binding to a tyrosine kinase receptor. It has been suggested that other EGF-like domains also function as ligands for receptor molecules (Engel, 1989, *FEBS Lett.* 251:1–7). Fundamentally, EGF repeats are protein structures that participate in specific protein-protein binding interactions.

The Drosophila Notch protein, the Nematode lin-12 and glp-1 proteins, and the closely related vertebrate homologs, Motch (mouse Notch), Xotch (Xenopus Notch), rat Notch, and TAN 1 (human Notch) are membrane bound receptor molecules that control the specification of cell fate for a variety of cell types early in embryogenesis (Rebay et al., 1991, *Cell* 67:687; Hutter and Schnabel, 1994, *Development* 120:2051; Del Amo et al 1992, *Development* 115:737; Reaume et al. 1992 *Develop. Biol.* 154:377; and Ellisen et al., 1991, *Cell* 66:649). Specific EGF-like repeats in the Notch receptors are binding sites that attach to protein ligands leading to signal transduction (Rebay et al., 1991 *Cell* 67:687; Couso and Arias, 1994, *Cell* 79:259; Fortini and Artavanis-Tsakonas, 1994, *Cell* 79:273; Henderson et al., 1994, *Development* 120:2913). Extracellular matrix proteins such as thrombospondin, entactin, tenascin and laminin play key roles in morphogenesis by providing the physical scaffold to which cells attach to form and maintain tissue morphologies (Frazier, 1987, *J. Cell. Biol.* 105:625; Taraboletti et al., 1990, *J. Cell. Biol.* 111:765; Ekblom et al., 1994, *Development* 120:2003).

2.3. DISCOINDIN I/FACTOR VIII-LIKE DOMAINS

A homologous domain structure has been discovered in coagulation factors VIII and V (Kane and Davie, 1986, *Proc. Natl. Acad. Sci. U.S.A.* 83:6800). This domain is related to a more ancient structure first observed in the discoidin I protein produced by the cellular slime mold *Dictyostelium discoideum*. Discoidin I is a carbohydrate binding lectin secreted by Dictyostelium cells during the process of cellular aggregation and is involved in cell-substratum attachment and ordered cell migration (Springer et al., 1984, *Cell* 39:557).

Discoidin I/factor VIII-like domains have also been observed in a number of other proteins. For example, milk fat globule protein (BA46), milk fat globule membrane protein (MFG-E8) (SEQ ID NO:21), breast cell carcinoma discoidin domain receptor (DDR), and the Xenopus neuronal recognition molecule (A5) (Stubbs et al., 1990, *Proc. Natl. Acad. Sci. U.S.A.* 87:8417; Larocca et al., 1991, *Cancer Res.* 51:4994; Johnson et al., 1993, *Proc. Natl. Acad. Sci. U.S.A.* 90:5677). The discoidin I/factor VIII-like domains of the vertebrate proteins are all distantly related to the Dictyostelium sequence but more closely related to each other.

Discoidin I/factor VIII-like domains are rich in positively charged basic amino acids and are believed to bind to negatively charged substrates such as anionic phospholipids or proteoglycans. Both of the milk fat globule proteins have been shown to associate closely with cell membranes and the coagulation factors VIII and V interact with specific platelet membrane proteins (Stubbs et al., 1990 *Proc. Nat. Acad. Sci. U.S.A.* 87:8417; Larocca et al., 1991, *Cancer Res.* 51:4994).

3. SUMMARY OF THE INVENTION

The present invention relates to a novel gene family. In particular, it relates to del-1 nucleotide sequence, expression vectors, host cells expressing del-1, Del-1 protein, methods of expressing del-1 and methods of using del-1 in various normal and disease conditions.

The invention is based, in part, upon Applicants' isolation of a murine DNA clone (SEQ ID NO:9), del-1, and its homologous human counterpart (SEQ ID NO:11). Structural features of the Del-1 protein are deduced by homology comparisons with sequences in the Genbank and NBRF-PIR databases. The protein is a modular molecule composed of repeats of two different sequence motifs which are present in a number of distinct proteins. The two sequence motifs are known as the EGF-like domain (SEQ ID NO:26) and the discoidin I/Factor VIII domain. These domains are defined by characteristic patterns of conserved amino acids distributed throughout the molecule at specific locations. While Del-1 shows certain sequence homology with other proteins, it is unique in both its primary sequence and its overall structure. In all cases in which EGF (SEQ ID NOS:23, 24, 25 & 26) and discoidin I domains (SEQ ID NOS:1–8) have been identified, both of these structures are always found in extracellular locations. This indicates that the Del-1 protein may also be an extracellular molecule. The expression pattern of del-1 further indicates that it is involved in endothelial cell function. Therefore, a wide variety of uses are encompassed by the present invention, including but not limited to, the diagnosis of cancer, the isolation of embryonic endothelial cells, the identification of a Del-1 binding partner, and the stimulation or inhibition of endothelial cell growth.

4. BRIEF DESCRIPTION OF THE DRAWINGS

FIG. 1. Genomic organization of 42 kb of the murine del-1 locus, as characterized by cloning from a λfix library constructed from the SLM275 transgenic mouse, and a wildtype 129SV λfix library. The dashed line indicates DNA studied to date by zoo blot and exon trapping. The location of the exon identified by exon trapping is shown.

FIG. 2. Homology analysis between the deduced amino acid sequence of the putative del-1 gene (mdel-1) (SEQ ID NO:1) and other proteins with "discoidin-like domains." Identical residues are boxed, conserved residues are shaded (Geneworks, Intelligenetics, Mountain View, Calif.). mdel-1 sequence (SEQ ID NO:1) was derived from a trapped exon and mouse embryo cDNAs. Abbreviations:h-MFG (SEQ ID NO:2), human milk fat globule protein; h-FV (SEQ ID NO:3), human coagulation factor V; M-FVIII (SEQ ID NO:4), mouse coagulation factor VIII; X-A5b1 (SEQ ID NO:5) and X-A5b2 (SEQ ID NO:6), b1 and b2 domains of Xenopus neuronal antigen A5; dis-I (SEQ ID NO:7), discoidin I.

FIGS. 3A–3D. Nucleotide sequence of murine del-1 cDNA (SEQ ID NO:9).

FIGS. 4A–C. Nucleotide sequence and deduced amino acid sequence of human del-1 cDNA (SEQ ID NO:11).

FIG. 5. Murine del-1 fragment (SEQ ID NO:13) used as probe for human del-1 cloning and Northern blot analysis.

Figure 6:
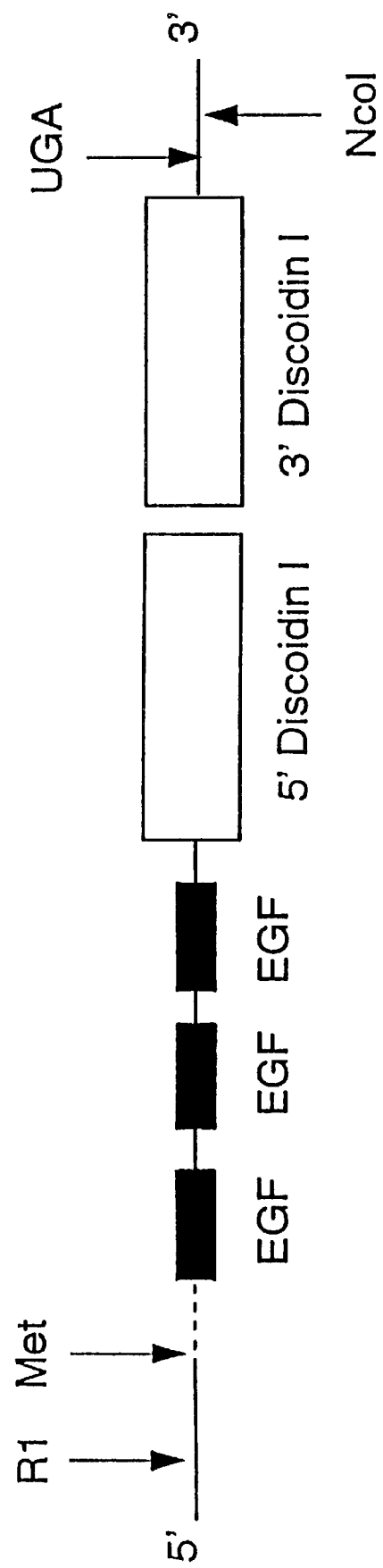

FIG. 6. The small rectangles labeled "EGF" show the location and relative sizes of the three EGF-like domains of del-1. These regions of the protein are approximately 40 amino acids long. Each EGF-like domain contains six cysteine residues and additional conserved amino acids, distributed in a pattern which is highly conserved among proteins that contain this common motif. In addition, the amino acid sequence RGD occurs in the center of the second EGF-like repeat. This sequence is found in a variety of extracellular matrix proteins and, in come cases, it is required for binding to integrin proteins. An RGD sequence is present in the same position in the second EGF-like repeat of MFG-E8. The large rectangles on the right side represent tandem discoidin I/factor VIII-like domains. This protein motif is based on a conserved pattern of amino acids defined by the homology between the *D. discoidium* discoidin I protein and mammalian coagulation factor VIII.

FIG. 7. The 54.2% amino acid homology between human del-1 (SEQ ID NO:20) and MFG-E8 (SEQ ID NO:21) in the tandem discoidin I/factor VIII domains is shown. These domains are rich in the basic amino acids arginine and lysine. The 5' domain contains 12 arginines and 12 lysines versus 9 acidic residues, while the 3' domain contains 8 arginines and 10 lysines versus 16 acidic residues. A similar domain in the coagulation factor VIII protein is believed to bind to negatively charged phospholipids on the surface of platelets. The MFG-E8 protein has been found to associate tightly with milk fat globule membranes.

FIG. 8. The predicted amino acid sequence at the amino terminus of the Del-1 (SEQ ID NO:22) protein shows characteristics common to signal peptides. The putative signal begins with a basic arginine residue and is followed by a stretch of 18 amino acids rich in hydrophobic residues. Signal peptides typically end with a small amino acid such as glycine or alanine. In addition, the Chou and Fasman algorithm predicts that the putative signal sequence is followed by a protein turn structure, a feature commonly found after signal peptides. It is likely the Del-1 protein is secreted by expressing cells.

FIG. 9. Sequence similarities between the three EGF-like domains of Del-1 (SEQ ID NOS:23, 24, & 25) and homology with the consensus EGF-like domain amino acid sequence (SEQ ID NO:26) are shown. Also, the amino acid sequence RGD is in the center of the second EGF-like repeat. This sequence is found in a variety of extracellular matrix proteins and, in some cases, is required for binding to integrin proteins. An RGD sequence is present in the same position in the second EGF-like repeat of MFG-E8.

FIG. 10. Human del-1 splicing variant sequence (SEQ ID NO:27).

FIGS. 11A–11D. Murine del-1 truncated minor sequence (SEQ ID NO:28 and SEQ ID NO:29).

FIG. 12A–12H. X-gal staining in whole mount and tissue sections of embryos from the SLM275 line. (12A) Embryo at 7.5 days pc (headfold stage) stained as whole mount. X-gal staining is seen in cells of the extraembryonic mesoderm (xm) which will give rise to the yolk sac and associated blood islands. Abbreviations: ng, neural groove. Photographed at 70×. (12B) Section of yolk sac blood islands from 8 day pc embryo stained as a whole mount with membranes intact and subsequently sectioned and counterstained. Clusters of round cells in the blood islands show X-gal staining (arrow), while mature endothelial cells do not stain (open arrowhead). Photographed at 400×. (12C) Embryo at 9.5 days pc. Prominent X-gal staining (blue-green) is seen in the heart and outflow tract (mid-portion of embryo). In addition, the aorta (arrowhead) and intervertebral vessels are stained. Photographed at approximately 30×, darkfield illumination. (12D) Section of 9.5 day embryo showing heart and outflow tract. This section indicates that X-gal staining in the heart and outflow tract is restricted to the endothelial cells (endocardium). Section was counterstained with hematoxylin and eosin, photographed at 200×. (12E) Embryo 13.5 days pc, dissected and X-gal stained as a whole mount. At this stage, as confirmed by study of tissue sections, endothelial cells lining the ventricle (v) and large vessels such as the aorta (filled arrowhead) have lost most of their staining. Staining of the endothelial cells of the atrium (a) has diminished but is still apparent in the whole mount. Most pronounced at this stage is staining in the developing lungs (open arrowheads). X-gal staining cells are clearly associated with the glandular buds of the lung, but it is not possible to identify these cells in the whole mount. The only non-cardiovascular cells which exhibit X-gal staining are cells in the regions of ossification, such as in the proximal ribs shown here. Photographed at 50x. (12F) Embryo 13.5 days, stained as whole mount, sectioned, counterstained with nuclear fast red. X-gal staining in lung tissue shown here is associated with endothelial cells, as seen in vascular channels cut in transverse (arrow) and longitudinal (arrowhead) planes. Staining is not associated with bronchial cells. Section was photographed at 400x. (12G) Cross-section through a valve forming in the outflow tract of a 13.5 day embryo. Endothelial cells in blood vessel wall are undergoing an epithelial-mesenchymal transformation, leading to formation of the valve tissue. Stained cells are seen within the forming valve structure, indicating that these cells continue to express the del-1 marker during this phenotypic transformation. The embryo was stained as a whole mount, sectioned, counterstained with nuclear fast red and photographed at 400x. (12H) Spiral septal formation in the outflow tract of the heart at 9.5 days pc. Endothelial cells are undergoing an epithelial-mesenchymal transformation, becoming mesenchymal in morphology and behavior. Endothelial cells continue to express the transgene marker for some time after this transformation. Section from whole mount stained embryo, 200x.

5. DETAILED DESCRIPTION OF THE INVENTION

The present invention relates to a novel family of nucleotide sequences referred to herein as del-1. Described below are methods for cloning members of this gene family, characteristics of a murine member and its human homolog, and methods of using the gene product. Structurally, members of this gene family contain three EGF-like domains and two discoidin I/factor VIII domains.

The overall structure of the del-1 molecule is similar to the milk fat globule membrane protein (MFG-E8) (Stubbs et al., 1990, *Proc. Natl. Acad. Sci . USA* 87:8417). MFG-E8 is highly expressed by a large portion of human breast tumors as well as by lactating mammary epithelial cells. It consists of two tandem EGF-like domains followed by two discoidin I/factor VIII domains (SEQ ID NO:21). The function of MFG-E8 is not known but it has been shown to associate closely with cell membranes and has been investigated as a target for antibody-based tumor imaging techniques. The observed association of MFG-E8 with cell membranes indicates the potential use of antibodies against Del-1 to identify and sort endothelial cells from mixed cell populations.

The second EGF-like repeat of MFG-E8 contains the amino acid sequence arg-gly-asp (RGD) in the same position as the second EGF-like repeat of Del-1. The RGD sequence has been shown to be a cell binding site for fibronectin, discoidin I, nidogen/entactin, and tenascin (Anderson, 1990, *Experientia* 46:2). The binding of fibronectin to cell surface integrin molecules through the RGD sequence has been extensively studied (Main et al., 1992, *Cell* 71:671; Hynes, 1992, *Cell* 69:11). Integrins appear to be the major receptors by which cells attach to extracellular matrices. Substrate binding to integrins has been shown to initiate signal transduction leading to events such as tyrosine phosphorylation, cytoplasmic alkalinization, activation of secretion and differentiation (Hynes, 1992, *Cell* 69:11). The presence of the RGD sequence in Del-1 indicates that this portion of the molecule may bind cell surface integrins, possibly triggering certain developmental events. In several cases, synthetic peptides containing the RGD sequence have been shown to compete with native protein for integrin binding and prevent the initiation of downstream events (Brooks et al., 1994, *Cell* 79:1157).

For clarity of discussion, the invention is described in the subsections below by way of example for the del-1 gene in mice and in humans. However, the findings disclosed herein may be analogously applied to other members of the del-1 family in all species.

5.1. THE DEL-1 CODING SEQUENCE

The present invention relates to nucleic acid and amino acid sequences of the del-1 gene family. In a specific embodiment by way of example in Section 6, infra, murine and human del-1 nucleotide and deduced amino acid sequences were cloned and characterized. Both the nucleotide coding sequence and deduced amino acid sequence of del-1 are unique. In accordance with the invention, any nucleotide sequence which encodes the amino acid sequence of the del-1 gene product can be used to generate recombinant molecules which direct the expression of del-1 gene.

Enhancer trapping is a strategy which has been successfully employed in genetic analysis in Drosophila but is also applicable to higher organisms. This method identifies regulatory regions in genomic loci through their influence on reporter genes (Okane et al., 1987, *Proc. Natl. Acad. Sci. U.S.A.* 84:9123–9127). The reporter gene, as a transcriptional unit under the control of a weak constitutively expressed eukaryotic promoter, is introduced into a large number of organisms. The offsprings of these organisms are then screened by analysis of the pattern of reporter gene expression. Lines which show expression in the appropriate cells at the appropriate time are maintained for further study. This strategy has successfully identified a number of loci in Drosophila involved in complex developmental processes.

Enhancer trap experiments have been employed in mice to a limited extent (Allen et al., 1988, *Nature* 333:852–855). A number of such experiments were through fortuitous integration of a reporter gene into a locus of interest (Kothary et al., 1988, *Nature* 335:435–437). Using this method coupled with genomic and cDNA cloning, the murine del-1 locus associated with the transgene was identified. A genomic library is generated from the-transgenic mouse, and a probe from the transgene used to isolate clones containing the transgene and sequences flanking the integration site. Characterization of the regulatory region is accomplished by employing flanking sequences in functional assays, via transfection experiments with an appropriate cell culture line, or via further transgenic experiments (Bhat et al., 1988, *Mol. Cell. Biol.* 8:3251–3259).

For analysis of the transcription unit, it is necesIsary to identify a region of flanking sequence which contains a portion of exon. This has been accomplished by blindly using flanking genomic sequences as probes in northern blots or zoo blots (Soinen et al., 1992, *Mechanisms of Development* 39:111–123). DNA fragments thus identified to contain exon sequence are employed as probes for cDNA cloning. Similar cloning experiments have been conducted to characterize loci inactivated by insertional mutagenesis associated with transgene integration. These experiments indicate that deletions of large regions of genomic DNA may accompany transgene integration, and that complexity of the transcription unit may greatly complicate this type of analysis (Karls et al., 1992, *Mol. Cell. Biol.* 12:3644–3652; Woychik et al., 1990, *Nature* 346:850–853).

Subsequent analysis of the del-1 sequence has revealed both EGF-like (SEQ ID NO:26) and discoidin I/factor VIII-like domains. The shared homology between del-1 and other known molecules is discussed in Section 6.2, infra. However, this molecule also contains regions of previously unreported unique nucleotide sequences. Northern blot hybridization analysis indicates that del-1 mRNA is highly expressed in fetal cells. In addition, the del-1 sequence is expressed in certain tumor cells.

In order to clone the full length cDNA sequence from any species encoding the entire del-1 cDNA or to clone variant forms of the molecule, labeled DNA probes made from nucleic acid fragments corresponding to any murine and human of the partial cDNA disclosed herein may be used to screen a cDNA library. More specifically, oligonucleotides corresponding to either the 5' or 3' terminus of the cDNA sequence may be used to obtain longer nucleotide sequences. Briefly, the library may be plated out to yield a maximum of 30,000 pfu for each 150 mm plate. Approximately 40 plates may be screened. The plates are incubated at 37° C. until the plaques reach a diameter of 0.25 mm or are just beginning to make contact with one another (3–8 hours). Nylon filters are placed onto the soft top agarose and after 60 seconds, the filters are peeled off and floated on a DNA denaturing solution consisting of 0.4N sodium hydroxide. The filters are then immersed in neutralizing solution consisting of 12M Tris HCL, pH 7.5, before being allowed to air dry. The filters are prehybridized in casein hybridization buffer containing 10% dextran sulfate, 0.5M NaCl, 50 mM Tris HCL, pH 7.5, 0.1% sodium pyrophosphate, 1% casein, 1% SDS, and denatured salmon sperm DNA at 0.5 mg/ml for 6 hours at 60° C. The radiolabelled probe is then denatured by heating to 95° C. for 2 minutes and then added to the prehybridization solution containing the filters. The filters are hybridized at 60° C. for 16 hours. The filters are then washed in 1× wash mix (10× wash mix contains 3M NaCl, 0.6M Tris base, and 0.02M EDTA) twice for 5 minutes each at room temperature, then in 1× wash mix containing 1% SDS at 60° C. for 30 minutes, and finally in 0.3× wash mix containing 0.1% SDS at 60° C. for 30 minutes. The filters are then air dried and exposed to x-ray film for autoradiography. After developing, the film is aligned with the filters to select a positive plaque. If a single, isolated positive plaque cannot be obtained, the agar plug containing the plaques will be removed and placed in lambda dilution buffer containing 0.1M NaCl, 0.01M magnesium sulfate, 0.035M Tris HCl, pH 7.5, 0.01% gelatin. The phage may then be replated and rescreened to obtain single, well isolated positive plaques. Positive plaques may be isolated and the cDNA clones sequenced using primers based on the known cDNA sequence. This step may be repeated until a full length cDNA is obtained.

It may be necessary to screen multiple cDNA libraries from different tissues to obtain a full length cDNA. In the event that it is difficult to identify cDNA clones encoding the complete 5' terminal coding region, an often encountered situation in cDNA cloning, the RACE (Rapid Amplification of cDNA Ends) technique may be used. RACE is a proven PCR-based strategy for amplifying the 5' end of incomplete cDNAs. 5'-RACE-Ready cDNA synthesized from human fetal liver containing a unique anchor sequence is commercially available (Clontech). To obtain the 5' end of the cDNA, PCR is carried out on 5'-RACE-Ready cDNA using the provided anchor primer and the 3' primer. A secondary PCR reaction is then carried out using the anchored primer and a nested 3' primer according to the manufacturer's instructions. Once obtained, the full length cDNA sequence may be translated into amino acid sequence and examined for certain landmarks such as a continuous open reading frame flanked by translation initiation and termination sites, EGF-like domain, discoidin I-like domain, a potential signal sequence and transmembrane domain, and finally overall structural similarity to the del-1 genes disclosed herein.

5.2. EXPRESSION OF DEL-1 SEQUENCE

In accordance with the invention, del-1 polynucleotide sequence which encodes the Del-1 protein, peptide fragments of Del-1, Del-1 fusion proteins or functional equivalents thereof, may be used to generate recombinant DNA molecules that direct the expression of Del-1 protein, Del-1 peptide fragment, fusion proteins or a functional equivalent thereof, in appropriate host cells. Such del-1 polynucleotide sequences, as well as other polynucleotides which selectively hybridize to at least a part of such del-1 polynucleotides or their complements, may also be used in nucleic acid hybridization assays, Southern and Northern blot analyses, etc.

Due to the inherent degeneracy of the genetic code, other DNA sequences which encode substantially the same or a functionally equivalent amino acid sequence, may be used in the practice of the invention for the cloning and expression of the Del-1 protein. Such DNA sequences include those which are capable of hybridizing to the murine and/or human del-1 sequences under stringent conditions. The phrase "stringent conditions" as used herein refers to those hybridizing conditions that (1) employ low ionic strength and high temperature for washing, for example, 0.015M NaCl/0.0015M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75M NaCl, 0.075M Sodium pyrophosphate, 5×Denhardt's solution, sonicated salmon sperm DNA (50 g/ml), 0.1% SDS, and 10% dextran sulfate at 42° C., with washes at 42° C. in 0.2×SSC and 0.1% SDS.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within a Del-1 sequence, which result in a silent change thus producing a functionally equivalent Del-1 protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine, tyrosine; and amino acids with nonpolar head groups include alanine, valine, isoleucine, leucine, phenylalanine, proline, methionine, tryptophan.

The DNA sequences of the invention may be engineered in order to alter a del-1 coding sequence for a variety of ends, including but not limited to, alterations which modify processing and expression of the gene product. For example, mutations may be introduced using techniques which are well known in the art, e.g., site-directed mutagenesis, to insert new restriction sites, to alter glycosylation patterns, phosphorylation, etc.

In another embodiment of the invention, a del-1 or a modified del-1 sequence may be ligated to a heterologous sequence to encode a fusion protein. For example, for screening of peptide libraries for molecules that bind Del-1, it may be useful to encode a chimeric Del-1 protein expressing a heterologous epitope that is recognized by a commercially available antibody. A fusion protein may also be engineered to contain a cleavage site located between a Del-1 sequence and the heterologous protein sequence, so that the Del-1 may be cleaved away from the heterologous moiety.

In an alternate embodiment of the invention, the coding sequence of Del-1 could be synthesized in whole or in part, using chemical methods well known in the art. See, for example, Caruthers et al., 1980, Nuc. Acids Res. Symp. Ser. 7:215–233; Crea and Horn, 180, Nuc. Acids Res. 9(10):2331; Matteucci and Caruthers, 1980, Tetrahedron Letter 21:719; and Chow and Kempe, 1981, Nuc. Acids Res. 9(12):2807–2817. Alternatively, the protein itself could be produced using chemical methods to synthesize an Del-1 amino acid sequence in whole or in part. For example, peptides can be synthesized by solid phase techniques, cleaved from the resin, and purified by preparative high performance liquid chromatography. (e.g., see Creighton, 1983, Proteins Structures And Molecular Principles, W.H. Freeman and Co., N.Y. pp. 50–60). The composition of the synthetic peptides may be confirmed by amino acid analysis or sequencing (e.g., the Edman degradation procedure; see Creighton, 1983, Proteins, Structures and Molecular Principles, W.H. Freeman and Co., N.Y., pp. 34–49).

In order to express a biologically active Del-1, the nucleotide sequence coding for Del-1, or a functional equivalent, is inserted into an appropriate expression vector, i.e., a vector which contains the necessary elements for the transcription and translation of the inserted coding sequence. The del-1 gene products as well as host cells or cell lines transfected or transformed with recombinant del-1 expression vectors can be used for a variety of purposes. These include but are not limited to generating antibodies (i.e., monoclonal or polyclonal) that competitively inhibit activity of Del-1 protein and neutralize its activity; and antibodies that mimic the activity of Del-1 binding partners such as a receptor. Anti-Del-1 antibodies may be used in detecting and quantifying expression of Del-1 levels in cells and tissues, as well as isolating Del-1-positive cells.

5.3. EXPRESSION SYSTEMS

Methods which are well known to those skilled in the art can be used to construct expression vectors containing the del-1 coding sequence and appropriate transcriptional/translational control signals. These methods include in vitro recombinant DNA techniques, synthetic techniques and in vivo recombination/genetic recombination. See, for example, the techniques described in Sambrook et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the del-1 coding sequence. These include but are not limited to microorganisms such as bacteria transformed with recombinant bacteriophage DNA, plasmid DNA or cosmid DNA expression vectors containing the del-1 coding sequence; yeast expression vectors containing the del-1 coding sequence; insect cell systems infected with recombinant virus expression vectors (e.g., baculovirus) containing the del-1 coding sequence; plant cell systems infected with recombinant virus expression vectors (e.g., cauliflower mosaic virus, CAMV; tobacco mosaic virus, TMV) or transformed with recombinant plasmid expression vectors (e.g., Ti plasmid) containing the del-1 coding sequence; or animal cell systems. The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll $\alpha/\beta$ binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the del-1 DNA, SV40-, BPV- and EBV-based vectors may be used with an appropriate selectable marker.

In bacterial systems a number of expression vectors may be advantageously selected depending upon the use intended for the del-1 expressed. For example, when large quantities of del-1 are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., 1983, EMBO J. 2:1791), in which the del-1 coding sequence may be ligated into the vector in frame with the lacZ coding region so that a hybrid AS-lacZ protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned polypeptide of interest can be released from the GST moiety.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II.

In cases where plant expression vectors are used, the expression of the del-1 coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

An alternative expression system which could be used to express del-1 is an insect system. In one such system, *Autographa californica* nuclear polyhidrosis virus (AcNPV) is used as a vector to express foreign genes. The virus grows in *Spodoptera frugiperda* cells. The del-1 coding sequence may be cloned into non-essential regions (for example the polyhedrin gene) of the virus and placed under control of an AcNPV promoter (for example the polyhedrin promoter). Successful insertion of the del-1 coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Viol. 46:584; Smith, U.S. Pat. No. 4,215,051).

In mammalian host cells, a number of viral based expression systems may be utilized. In cases where an adenovirus is used as an expression vector, the del-1 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing del-1 in infected hosts. (e.g., See Logan & Shenk, 1984, Proc. Natl. Acad. Sci. USA 81:3655–3659). Alternatively, the vaccinia 7.5K promoter may be used. (See, e.g., Mackett et al., 1982, Proc. Natl. Acad. Sci. USA 79:7415–7419; Mackett et al., 1984, J. Virol. 49:857–864; Panicali et al., 1982, Proc. Natl. Acad. Sci. USA 79:4927–4931).

Specific initiation signals may also be required for efficient translation of inserted del-1 coding sequences. These signals include the ATG initiation codon and adjacent sequences. In cases where the entire del-1 gene, including its own initiation codon and adjacent sequences, is inserted into the appropriate expression vector, no additional translational control signals may be needed. However, in cases where only a portion of the del-1 coding sequence is inserted, exogenous translational control signals, including the ATG initiation codon, must be provided. Furthermore, the initiation codon must be in phase with the reading frame of the del-1 coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. The presence of several consensus N-glycosylation sites in the del-1 extracellular domain support the possibility that proper modification may be important for Del-1 function. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, etc.

For long-term, high-yield production of recombinant proteins, stable expression is preferred. For example, cell lines which stably express the del-1 may be engineered. Rather than using expression vectors which contain viral origins of replication, host cells can be transformed with the del-1 DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the Del-1 protein on the cell surface. Such engineered cell lines are particularly useful in screening for molecules or drugs that affect del-1 function.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk-, hgprt- or aprt- cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981), Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

5.4. IDENTIFICATION OF CELLS THAT EXPRESS DEL-1

The host cells which contain the coding sequence and which express the biologically active gene product may be identified by at least four general approaches; (a) DNA— DNA or DNA-RNA hybridization; (b) the presence or absence of "marker" gene functions; (c) assessing the level of transcription as measured by the expression of del-1

MRNA transcripts in the host cell; and (d) detection of the gene product as measured by immunoassay or by its biological activity. Prior to the identification of gene expression, the host cells may be first mutagenized in an effort to increase the level of expression of del-1, especially in cell lines that produce low amounts of del-1.

In the first approach, the presence of the del-1 coding sequence inserted in the expression vector can be detected by DNA—DNA or DNA-RNA hybridization using probes comprising nucleotide sequences that are homologous to the del-1 coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the del-1 coding sequence is inserted within a marker gene sequence of the vector, recombinants containing the del-1 coding sequence can be identified by the absence of the marker gene function. Alternatively, a marker gene can be placed in tandem with the del-1 sequence under the control of the same or different promoter used to control the expression of the del-1 coding sequence. Expression of the marker in response to induction or selection indicates expression of the del-1 coding sequence.

In the third approach, transcriptional activity for the del-1 coding region can be assessed by hybridization assays. For example, RNA can be isolated and analyzed by Northern blot using a probe homologous to the del-1 coding sequence or particular portions thereof. Alternatively, total nucleic acids of the host cell may be extracted and assayed for hybridization to such probes.

In the fourth approach, the expression of the Del-1 protein product can be assessed immunologically, for example by Western blots, immunoassays such as radioimmunoprecipitation, enzyme-linked immunoassays and the like.

5.5. USES OF DEL-1 ENGINEERED CELL LINES

In an embodiment of the invention, the Del-1 protein and/or cell lines that express Del-1 may be used to screen for antibodies, peptides, or other cell bound or soluble molecules that bind to the Del-1 protein. For example, anti-Del-1 antibodies may be used to inhibit or stimulate Del-1 function. Alternatively, screening of peptide libraries with recombinantly expressed soluble Del-1 protein or cell lines expressing Del-1 protein may be useful for identification of therapeutic molecules that function by inhibiting or stimulating the biological activity of Del-1. The uses of the Del-1 protein and engineered cell lines, described in the subsections below, may be employed equally well for other members of the del-1 gene family in various species.

In an embodiment of the invention, engineered cell lines which express most of the del-1 coding region or a portion of it fused to another molecule such as the immunoglobulin constant region (Hollenbaugh and Aruffo, 1992, Current Protocols in Immunology, Unit 10.19; Aruffo et al., 1990, Cell 61:1303) may be utilized to produce a soluble molecule to screen and identify its binding partners. The soluble protein or fusion protein may be used to identify such a molecule in binding assays, affinity chromatography, immunoprecipitation, Western blot, and the like. Alternatively, portions of del-1 may be fused to the coding sequence of the EGF receptor transmembrane and cytoplasmic regions. Assuming that Del-1 can function as a cell-bound receptor, this approach provides for the use of the EGF receptor signal transduction pathway as a means for detecting molecules that bind to Del-1 in a manner capable of triggering an intracellular signal. On the other hand, Del-1 may be used as a soluble factor in binding to cell lines that express specific known cytokine receptors. Synthetic compounds, natural products, and other sources of potentially biologically active materials can be screened in a number of ways.

Random peptide libraries consisting of all possible combinations of amino acids attached to a solid phase support may be used to identify peptides that are able to bind to the ligand binding site of a given receptor or other functional domains of a receptor such as kinase domains (Lam, K. S. et al., 1991, Nature 354:82–84). The screening of peptide libraries may have therapeutic value in the discovery of pharmaceutical agents that stimulate or inhibit the biological activity of receptors through their interactions with the given receptor.

Identification of molecules that are able to bind to the Del-1 protein may be accomplished by screening a peptide library with recombinant soluble Del-1 protein. Methods for expression and purification of Del-1 are described in Section 5.2, supra, and may be used to express recombinant full length del-1 or fragments of del-1 depending on the functional domains of interest. For example, the EGF-like and discoidin I/factor VIII domains of del-1 may be separately expressed and used to screen peptide libraries.

To identify and isolate the peptide/solid phase support that interacts and forms a complex with Del-1, it is necessary to label or "tag" the Del-1 molecule. The Del-1 protein may be conjugated to enzymes such as alkaline phosphatase or horseradish peroxidase or to other reagents such as fluorescent labels which may include fluorescein isothiocyanate (FITC), phycoerythrin (PE) or rhodamine. Conjugation of any given label to Del-1 may be performed using techniques that are well known in the art. Alternatively, del-1 expression vectors may be engineered to express a chimeric Del-1 protein containing an epitope for which a commercially available antibody exist. The epitope specific antibody may be tagged using methods well known in the art including labeling with enzymes, fluorescent dyes or colored or magnetic beads.

The "tagged" Del-1 conjugate is incubated with the random peptide library for 30 minutes to one hour at 22° C. to allow complex formation between Del-1 and peptide species within the library. The library is then washed to remove any unbound protein. If Del-1 has been conjugated to alkaline phosphatase or horseradish peroxidase the whole library is poured into a petri dish containing substrates for either alkaline phosphatase or peroxidase, for example, 5-bromo-4-chloro-3-indoyl phosphate (BCIP) or 3,3',4,4"-diaminobenzidine (DAB), respectively. After incubating for several minutes, the peptide/solid phase-Del-1 complex changes color, and can be easily identified and isolated physically under a dissecting microscope with a micromanipulator. If a fluorescent tagged Del-1 molecule has been used, complexes may be isolated by fluorescence activated sorting. If a chimeric Del-1 protein expressing a heterologous epitope has been used, detection of the peptide/Del-1 complex may be accomplished by using a labeled epitope specific antibody. Once isolated, the identity of the peptide attached to the solid phase support may be determined by peptide sequencing.

In addition to using soluble Del-1 molecules, in another embodiment, it is possible to detect peptides that bind to cell surface receptors using intact cells. The use of intact cells is preferred for use with receptors that are multi-subunits or labile or with receptors that require the lipid domain of the cell membrane to be functional. Methods for generating cell lines expressing del-1 are described in Section 5.3. The cells used in this technique may be either live or fixed cells. The cells may be incubated with the random peptide library and bind to certain peptides in the library to form a "rosette" between the target cells and the relevant solid phase support/peptide. The rosette can thereafter be isolated by differential centrifugation or removed physically under a dissecting microscope.

As an alternative to whole cell assays for membrane bound receptors or receptors that require the lipid domain of the cell membrane to be functional, the receptor molecules can be reconstituted into liposomes where label or "tag" can be attached.

Various procedures known in the art may be used for the production of antibodies to epitopes of the natural and recombinantly produced Del-1 protein. Such antibodies include but are not limited to polyclonal, monoclonal, chimeric, single chain, Fab fragments and fragments produced by an Fab expression library. Neutralizing antibodies i.e., those which compete for the ligand binding site of the receptor are especially preferred for diagnostics and therapeutics.

Monoclonal antibodies that bind Del-1 may be radioactively labeled allowing one to follow their location and distribution in the body after injection. Radioisotope tagged antibodies may be used as a non-invasive diagnostic tool for imaging de novo cells of tumors and metastases.

Immunotoxins may also be designed which target cytotoxic agents to specific sites in the body. For example, high affinity Del-1 specific monoclonal antibodies may be covalently complexed to bacterial or plant toxins, such as diphtheria toxin, ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate Del-1 expressing tumor cells.

For the production of antibodies, various host animals may be immunized by injection with the Del-1 protein including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to Del-1 may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce Del-1-specific single chain antibodies.

Antibody fragments which contain specific binding sites of Del-1 may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to Del-1. Anti-Del-1 antibodies may be used to isolate Del-1-expressing cells or eliminate such cells from a cell mixture.

5.6. USES OF DEL-1 POLYNUCLEOTIDE

A del-1 polynucleotide may be used for diagnostic and/or therapeutic purposes. For diagnostic purposes, a del-1 polynucleotide may be used to detect del-1 gene expression or aberrant del-1 gene expression in disease states. Included in the scope of the invention are oligonucleotide sequences, that include antisense RNA and DNA molecules and ribozymes, that function to inhibit translation of a del-1.

5.6.1. DIAGNOSTIC USES OF A DEL-1 POLYNUCLEOTIDE

A del-1 polynucleotide may have a number of uses for the diagnosis of diseases resulting from aberrant expression of del-1. For example, the del-1 DNA sequence may be used in hybridization assays of biopsies or autopsies to diagnose abnormalities of del-1 expression; e.g., Southern or Northern analysis, including in situ hybridization assays. Such techniques are well known in the art, and are in fact the basis of many commercially available diagnostic kits.

5.6.2. THERAPEUTIC USES OF A DEL-1 POLYNUCLEOTIDE

A del-1 polynucleotide may be useful in the treatment of various abnormal conditions. By introducing gene sequences into cells, gene therapy can be used to treat conditions in which the cells do not proliferate or differentiate normally due to underexpression of normal del-1 or expression of abnormal/inactive del-1 . In some instances, the polynucleotide encoding a del-1 is intended to replace or act in the place of a functionally deficient endogenous gene. Alternatively, abnormal conditions characterized by overproliferation can be treated using the gene therapy techniques described below.

Abnormal cellular proliferation is an important component of a variety of disease states. Recombinant gene therapy vectors, such as viral vectors, may be engineered to express variant, signalling incompetent forms of Del-1 which may be used to inhibit the activity of the naturally occurring endogenous Del-1. A signalling incompetent form may be, for example, a truncated form of the protein that is lacking all or part of its signal transduction domain. Such a truncated form may participate in normal binding to a substrate but lack signal transduction activity. Thus recombinant gene therapy vectors may be used therapeutically for treatment of diseases resulting from aberrant expression or activity of an Del-1. Accordingly, the invention provides a method of inhibiting the effects of signal transduction by an endogenous Del-1 protein in a cell comprising delivering a DNA molecule encoding a signalling incompetent form of the Del-1 protein to the cell so that the signalling incompetent Del-1 protein is produced in the cell and competes with the endogenous Del-1 protein for access to molecules in the Del-1 protein signalling pathway which activate or are activated by the endogenous Del-1 protein.

Expression vectors derived from viruses such as retroviruses, vaccinia virus, adeno-associated virus, herpes viruses, or bovine papilloma virus, may be used for delivery of recombinant Del-1 into the targeted cell population. Methods which are well known to those skilled in the art can be used to construct recombinant viral vectors containing an del-1 polynucleotide sequence. See, for example, the techniques described in Maniatis et al. , 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y. Alternatively, recombinant Del-1 molecules can be reconstituted into liposomes for delivery to target cells.

Oligonucleotide sequences, that include anti-sense RNA and DNA molecules and ribozymes that function to inhibit the translation of a del-1 mRNA are within the scope of the invention. Anti-sense RNA and DNA molecules act to directly block the translation of mRNA by binding to targeted mRNA and preventing protein translation. In regard to antisense DNA, oligodeoxyribonucleotides derived from the translation initiation site, e.g. , between −10 and +10 regions of a del-1 nucleotide sequence, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Within the scope of the invention are engineered hammerhead motif ribozyme molecules that specifically and efficiently catalyze endonucleolytic cleavage of del-1 RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

Methods for introducing polynucleotides into such cells or tissue include methods for in vi tro introduction of polynucleotides such as the insertion of naked polynucleotide, i.e., by injection into tissue, the introduction of a del-1 polynucleotide in a cell ex vivo, i .e., for use in autologous cell therapy, the use of a vector such as a virus, retrovirus, phage or plasmid, etc. or techniques such as electroporation which may be used in vivo or ex vivo.

5.7. USES OF DEL-1 PROTEIN

Analysis of β-gal expression in transgenic mice in which β-gal gene expression is controlled by the del-1 enhancer indicates that the del-1 gene is activated in endothelial cells undergoing vasculogenesis. Vasculogenesis refers to the development of blood vessels de novo from embryonic precursor cells. The related process of angiogenesis is the process through which existing blood vessels arise by outgrowth from preexisting ones. Vasculogenesis is limited to the embryo while angiogenesis continues throughout life as a wound healing response or to increase oxygenation of chronically stressed tissues (Pardanaud et al., 1989 *Development* 105:473; Granger 1994, *Cell and Mol. Biol. Res.* 40:81).

It is likely that Del-1 functions during embryonic vasculogenesis and in angiogenesis. For therapeutic use, it is essential that Del-1, portions of Del-1 or antibodies that block Del-1, may interact with angiogenic cells since it is stimulation or inhibition of these cells that is clinically relevant. Manipulation of Del-1 function may have significant effects on angiogenesis if Del-1 normally participates in this process.

It is also possible that Del-1 may have an effect on angiogenesis even if it does not naturally participate in this process. Del-1 protein or recombinant proteins consisting of portions of Del-1 may function to activate or stimulate angiogenesis. This function could be clinically useful to promote neovascularization of tissues which are not receiving an adequate oxygen supply. Manipulation of Del-1 function may also be useful in inhibiting angiogenesis. It has been demonstrated that inhibition of angiogenesis is useful in preventing tumor metastases (Fidler and Ellis, 1994, *Cell* 79:185). Recently, O'Reilly et al (1994, *Cell* 79:315) reported that a novel angiogenesis inhibitor isolated from tumor-bearing mice, angiostatin, specifically inhibited endothelial cell proliferation. In vivo, angiostatin was a potent inhibitor of neovascularization and growth of tumor metastases. In a related report, Brooks et al (1994, *Cell* 79:115) showed that integrin antagonists promoted tumor regression by inducing apoptosis of angiogenic blood vessels. These integrin antagonists included cyclic peptides containing an RGD amino acid sequence. Since Del-1 contains an RGD sequence, manipulation of this portion of the Del-1 molecule may have similar effects.

Manipulation of the discoidin I/factor VIII-like domains of Del-1 may alsc-be used to inhibit angiogenesis. Apolipoprotein E (ApoE) has been shown to inhibit basic fibroblast growth factor (bFGF)-stimulated proliferation of endothelial cells in vitro (Vogel et al., 1994, *J. Cell. Biochem.* 54:299). This effect could also be produced with synthetic peptides based on a portion of the ApoE sequence. These results could be due to direct competition of ApoE with growth factors for binding to heparin sulfate proteoglycans, or through disruption-by ApoE of cell-matrix interactions. It has been proposed that discoidin I/factor VIII-like domains such as those in Del-1 bind to proteoglycans. In addition, Del-1 is similar in structure to a number of extracellular matrix proteins. Thus, Del-1 may be manipulated to effect the activity of growth factors such as BFGF or to alter interactions between endothelial cells and the extracellular matrix.

6. MOLECULAR CLONING OF HUMAN AND DEL-1 NUCLEOTIDE SEQUENCES

6.1. MATERIALS AND METHODS

6.1.1. GENERATION OF TRANSGENTIC MICE

The SLM275 transgenic mouse line was generated in a C57BL6xDBA/F1 background, and the transgenic animals had been crossed back against similar B6D2F1 animals for maintenance of the line and the generation of embryos. This transgene had been maintained in the heterozygous state, and these heterozygous mice had normal breeding capacity. However, preliminary experiments indicated that these animals were not viable in the homozygous state.

6.1.2. MOLECULAR CLONING OF DEL-1

A genomic library was constructed from high molecular weight DNA isolated from the kidney of a SLM275 transgenic animal. This DNA was subjected to partial digestion with Sau3A to obtain an average size of 20 kb, subjected to a partial fill-in reaction, and then cloned into a similarly treated lambdaphage vector (lambdaFix, Stratagene). The library constructed in this fashion had a base of approximately 2 million clones. These clones were amplified and the library stored at −70° C. A 200 basepair (bp) probe derived from the SV40 polyadenylation signal of the transgene was used as a probe and allowed the isolation of 12 lambdaphage clones. Six of these clones were randomly chosen for further investigation. These clones were mapped, and restriction fragments which did not contain transgene sequence identified. The clones were divided into two groups on the basis of common non-transgenic fragments. One such fragment from the first group of phage allowed specific hybridization to genomic blots and provided evidence that it was derived from a region adjacent to the integration site. Genomic DNA from a non-transgenic mouse of the same genetic background (B6D2F1) was compared to that of a SLM275 transgene animal by hybridization to this probe. Rearranged bands representing fragments disrupted by transgene integration were seen in the SLM275 lanes with both EcoR1 and BamH1 digests. The flanking sequence probe was employed to screen a commercially available lambdaFixII genomic library constructed from the 129SV mouse strain (Stratagene).

A murine cDNA fragment (SEQ ID NO:19) was used as a probe to identify cDNA clones of its human homolog. The probe corresponded to nucleotides 1249 through 1566 in the murine del-1 major sequence. Human cDNA clones were isolated from a human fetal lung cDNA library (Clonetech, Inc.) following standard procedures.

6.2. RESULTS

A transgenic mouse line was created through a fortuitous enhancer trap event. The original studies were designed to map the cell-specific and developmental-specific regulatory regions of the mouse SPARC promoter, 2.2 kilobases (kb) of the SPARC 5' flanking sequence were placed upstream of the E. coli lacZ (beta-galactosidase or β-gal) reporter gene. The mouse SPARC gene is normally expressed in a wide variety of adult and embryonic cells which synthesize a specific extracellular matrix (Nomura et al., 1989, J. Biol. Chem. 264:12201–12207). However, one of the founder mouse lines showed a highly restricted pattern of expression quite distinct from the native SPARC gene. Expression of the lacZ reporter in this particular line of mice referred to as SLM275 was seen very early in cells of the endothelial lineage. Whole mount lacZ staining was employed for initial studies, and these embryos subsequently sectioned and examined by light-microscopy. The first cells to stain were endothelial cells forming the endocardium, the outflow tract, and the developing intervertebral vessels. Staining appeared to be predominantly restricted to endothelial cells associated with forming major blood vessels. Expression began to decline after 11.5 days pc.

The genomic region targeted by this transgene is herein referred to as del-1. Initial cloning experiments were aimed at isolating genomic sequences flanking the transgene integration site. A number of lambdaphage clones were isolated and mapped (FIG. 1). Approximately 40 kb of the wild-type del-1 sequence was contained in these clones. By probing Southern blots containing restriction digests of these lambdaphages with non-transgenic fragments from the SLM275 lambdaphage clones, the site of transgene integration was mapped. Insertion of the transgene complex was associated with the deletion of approximately 8 kb of DNA. There were approximately 25 kb of flanking sequence on one side of the integration, and approximately 5 kb of the other flanking sequence contained on these clones.

Exon trapping was used to evaluate genomic fragments for the presence of exons. This approach utilized a vector with a constitutive promoter driving transcription through a DNA fragment containing a splice donor site and a splice acceptor site. Between these splicing signals was a common cloning site where the genomic DNA fragment to be evaluated was cloned. Exons within this fragment would be spliced into the transcript when the construct was transfected into eukaryotic cells, such as COS cells. The transcript containing the trapped exon sequence was rescued from the COS cells by reverse transcriptase polymerase chain reaction (RT-PCR). PCR amplified DNA was cloned and evaluated.

A 160 bp exon was trapped from a fragment of genomic DNA located approximately 10 kb from the "left" integration site. Nucleotide sequence of the trapped exon was employed to screen various nucleic acid databanks through the BLAST routine at the NCBI, revealing no other gene with significant nucleic acid homology. The deduced amino acid sequence of the single open reading frame was subsequently employed in databank searches. These revealed that the protein domain encoded in the trapped exon was similar in part to domains in a number of proteins, including Factor V, Factor VIII and discoidin I (SEQ ID NO:7) (FIG. 2) (Jenny et al., 1987, Proc. Natl. Acad. Sci. U.S.A. 84:4846–4850; Poole et al., 1981, J. Mol. Biol. 153:273–289; Toole et al., 1984, Nature 312:342–347). The protein which was most similar was milkfat globule protein, which had been found on the surface of mammary epithelial cells. It has been hypothesized that the discoidin I-like domain in this protein allows it to localize to the surface of the epithelial cell (Larocca et al., 1991, Cancer Res. 51:4994–4998; Stubbs et al., 1990, Proc. Natl. Acad. Sci. U.S.A. 87:8417–8421). The homologous regions of Factor V and Factor VIII have been implicated in their interaction with phospholipids on the surface of endothelial cells and platelets (Jenny et al., 1987, Proc. Natl. Acad. Sci. U.S.A.

84:4846–4850; Toole et al., 1984, *Nature* 312:342–347). Homology to the Xenopus protein A5 was also observed. A5 is a neuronal cell surface molecule which is expressed in retinal neurons and the neurons in the visual center with which the retinal neurons contact (Takagi et al., 1991, *Neuron* 7:295–307). A5 has been proposed to play a role as a neuronal recognition molecule in the development of this neural circuit, perhaps through mediating intercellular signaling. The protein for which this discoidin I-like domain was named is a protein expressed in *Dictyostelium discoideum*, which serves an essential role in the aggregation of individual cells.

The DNA fragment encoding the trapped exon was employed as a probe in a Southern blot experiment and shown to hybridize with regions of the del-1 locus outside of the region that was employed in the exon trap construct. Given this finding, cDNA cloning was pursued by using the exon trap probe to screen an 11.5 day embryonic mouse cDNA library. Clones were plaque purified, and inserts subcloned into plasmid for further analysis. Nucleotide sequence analysis showed that two of the embryonic cDNA clones contained the sequence of the trapped exon. Sequence from the clones was used to expand the deduced amino acid sequence of the discoidin I-like domain (SEQ ID NO:8) (FIG. 2). The full nucleotide sequence of these cDNAs (SEQ ID NO:9) was analyzed and cloned into plasmid vectors which allowed the generation of CRNA transcripts for RNAse protection and in situ hybridization (FIG. 3A–3E).

A human cDNA (SEQ ID NO:11) was isolated from a human fetal lung cDNA lambdaphage library purchased from Clontech Inc. (FIGS. 4A–4C). A portion of the mouse del-1 cDNA was used as a probe (SEQ ID NO:19) (FIG. 5). The identity of the human cDNA clone was confirmed by comparing the human and mouse DNA sequences. These clones show approximately 80% DNA sequence homology and 90% amino acid sequence homology. Upon initial isolation of del-1, standard molecular biology methods were used for isolating additional clones.

DNA sequence analysis of the human del-1 revealed an open reading frame of 1,446 base pairs predicted to encode a 482 amino acid protein with a molecular weight of 53,797. Homology comparisons with DNA and protein databases indicated that the del-1 protein was composed of three EGF-like protein domains, followed by two discoidin I/factor VIII-like domains (FIG. 6). Genes similar to del-1 included some key regulators of cell determination and differentiation such as Notch. Overall, the Del-1 protein has a structure similar to the membrane-associated milk fat globule membrane protein, MGF-E8 (SEQ ID NO:20), which has been used to develop antibodies for imaging breast cancer tumors (FIG. 7).

A physiologic function for the del-1 protein is implicated by the activities which have been demonstrated for EGF-like and discoidin I/factor VIII-like domains in other proteins. EGF-like domains have been shown to participate in protein-protein binding interactions, while the discoidin I-like domains of factor VIII are believed to mediate binding to cell membranes through association with negatively charged phospholipids. Thus, the Del-1 protein may generate a signal for endothelial cell determination or differentiation by binding to the membranes of precursor cells and interacting with an EGF-like domain receptor protein.

Key structural features of the open reading frame of human Del-1 include:

1) the presumed initiator methionine and putative secretion signal sequence (SEQ ID NO:22) (FIG. 8)
2) the three EGF-like domains (SEQ ID NOS:23, 24 & 25) (FIG. 9)
3) the two discoidin I-like domains.

Further cloning and analysis of both the human and murine del-1 genes revealed additional variant forms. For example, a human splicing variant (SEQ ID NO:27) (Z20 clone) was obtained in which 30 bp between the first and second EGF-like domains of the common form of del-1 had been removed (FIG. 10). In addition, a truncated version of murine del-1 (SEQ ID NO:28 and SEQ ID NO:29) was isolated, which contained all three EGF-like domains and only a partial first discoidin I/factor VIII-like domain (about 40%). This variant is referred to as murine del-1 minor sequence, which is disclosed in FIGS. 11A–11E.

7. TISSUE DISTRIBUTION OF DEL-1 GENE EXPRESSION

7.1. MATERIALS AND METHODS

7.1.1. WHOLE MOUNT STAINING OF TRANSGENIC MOUSE EMBRYOS

Male transgenic animals of second or third generation had been crossed with 8–10 week B6D2F1 females, and embryos harvested at 7.5, 8.5, 9.5, 10.5, and 13.5 days. Timing was based on the convention that noon of the day of plugging was 0.5 day post-coitum (pc). Embryos were harvested, dissected free of decidua and membranes, fixed in 2% glutaraldehyde, and stained as a whole mount in a standard X-gal indicator solution according to standard protocols. An exception was that embryos older than 11.5 days were bisected which allowed better penetration of the fixative and staining solution. Stained tissues were identified in whole mount embryos by examination at 7–70× with an Olympus SZH10 stereomicroscope, and photographed under darkfield illumination. Embryos 7.5, 8.5, 9.5, and 13.5 days pc were embedded in paraffin, sectioned, counterstained with nuclear fast red and examined under brightfield with a Zeiss Axioplan microscope.

7.1.2. NORTHERN BLOT ANALYSIS

In order to study the expression of the del-1 gene, Northern blots containing RNA obtained from a variety of human and mouse tissues (Clontech, Palo Alto, Calif.) were hybridized with a radiolabeled DNA probe as shown in FIG. 5. Briefly, the blots were prehybridized at 42° C. for 3–6 hours in a solution containing 5× SSPE, 10× Denhardt's solution, 100 μg/ml freshly denatured, sheared salmon sperm DNA, 50% formamide (freshly deionized), and 2% SDS. The radiolabeled probe was heat denatured and added to the prehybridization mix and allowed to hybridize at 42° C. for 18–24 hours with constant shaking. The blots were rinsed in 2× SSC, 0.05% SDS several times at room temperature before being transferred to a wash solution containing 0.1× SSC, 0.1% SDS and agitated at 50° C. for 40 minutes. The blots were then covered with plastic wrap, mounted on Whatman paper and exposed to x-ray film at −70° C. using an intensifying screen.

7.1.3 REVERSE TRANSCRIPTION/POLYMERASE CHAIN REACTION (RT/PCR)

Total RNA was isolated using standard laboratory procedures (Sambrook et al., 1989, Molecular Cloning, A Laboratory Manual, Cold Spring Harbor Laboratory, N.Y.). Approximately 1 μg of total RNA was reverse transcribed and the cDNA was amplified by PCR (Perkin Elmer, Norwalk, Conn.). The PCR amplification conditions were: 94° C. for 30 sec. 60° C. for 30 sec. 72° C. for 30 sec for a total of 40 cycles. The amplified products were resolved by agarose gel electrophoresis and visualized by ethidium bromide staining. The amplimers were:

+ strand primer: ACC CAA GGG GCA AAA AGG A
− strand primer: CCT GTA ACC ATT GTG ACT G

7.2. RESULTS

Expression of del-1 in various human and mouse tissues and cell lines was investigated by whole mount staining, Northern blot analysis and RT-PCR. Results of experiments are summarized in the sections below.

7.2.1 EXPRESSION ANALYSIS BY HISTOCHEMISTRY

Figure 12A:
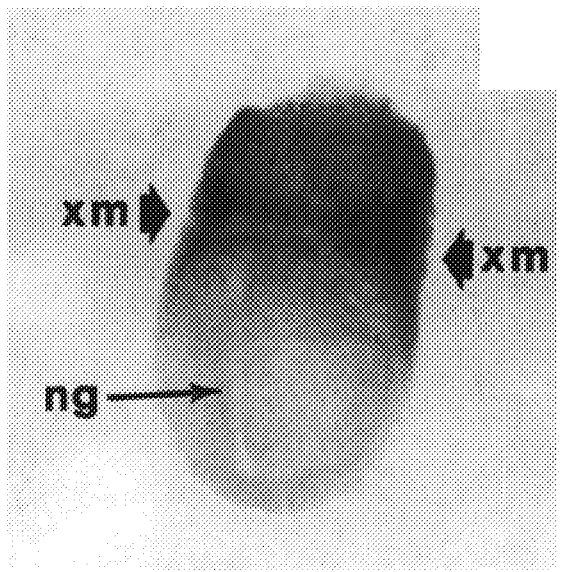

When the earliest time point was investigated by whole mount and histochemical staining in transgenic mice at day 7.5 pc, expression of the lacZ reporter gene was shown in cells forming the extra embryonic mesoderm (FIG. 12A). These cells would form the yolk sac and give rise to cells of the blood island. Expression of the lacZ reporter gene in this locus is thus one of the earliest known markers of the endothelial cell lineage. The only other marker which has been shown to be expressed in precursors of endothelial cells at this early stage of development is the receptor tyrosine kinase flk-1 (Millauer et al., 1993, *Cell* 72:835–846).

Figure 12B:
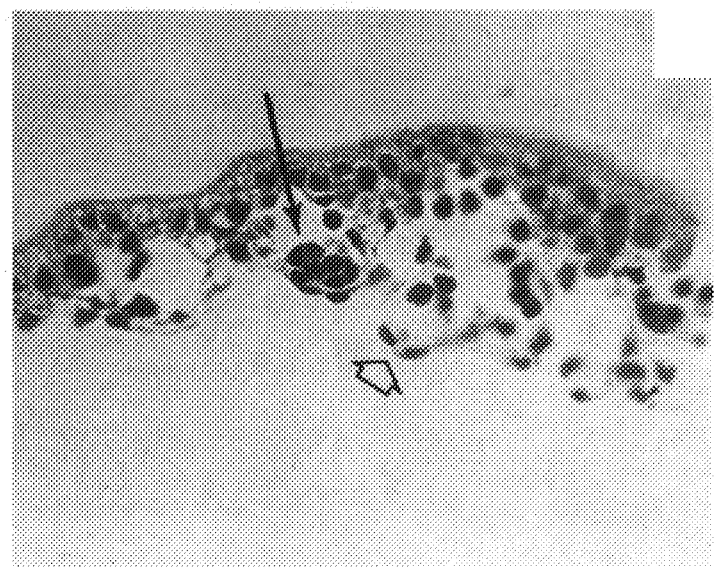
Figure 12C:
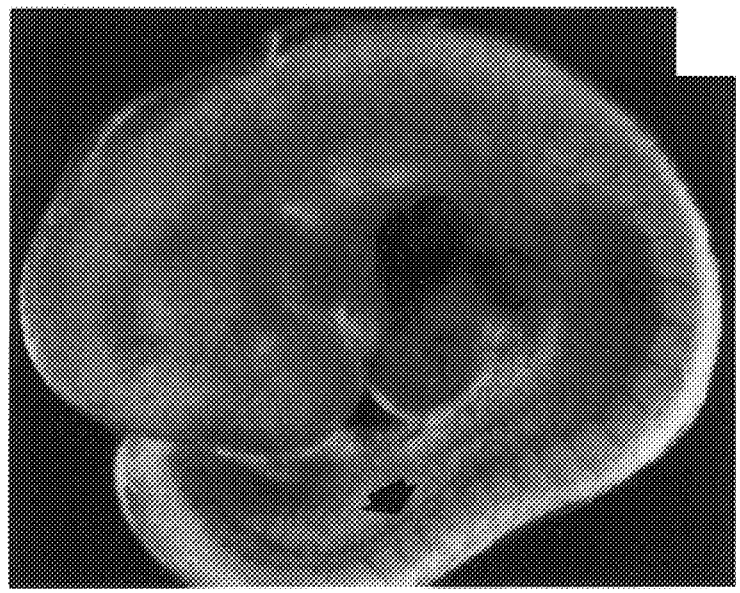
Figure 12D:
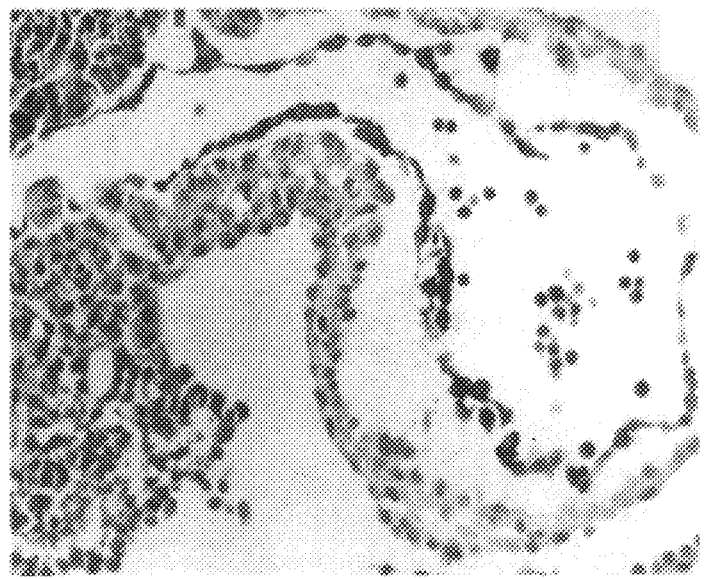

At day 8.5, lacZ staining was seen in cells in the blood islands of the yolk sac. Interestingly, staining was not detected in the endothelial cells lining the blood island, but rather in round cells found in clumps within the blood island (FIG. 12B). These round cells had large nuclei and were closer in appearance to hematopoietic precursors rather than endothelial cells. Thus, the del-1 locus might be expressed in early embryonic cells which were precursors to both endothelial and hematopoeitic lineages. In the late primitive streak stage embryo at 8.5 days pc, there was also staining of endothelial cells associated with the developing paired dorsal aortae. LacZ staining was seen in cells in the region of the forming heart at this stage, and these were presumably endothelial cells that would form the endocardium. By day 9.5 (10–14 somites), the endocardium and endothelial cells forming the outflow tract and aorta showed lacZ staining (FIGS. 12C, 12D). This staining persisted until day 10.5 and 11.5, and by whole mount analysis endothelial cells associated with all large vascular structures were expressing the reporter gene.

Figure 12E:
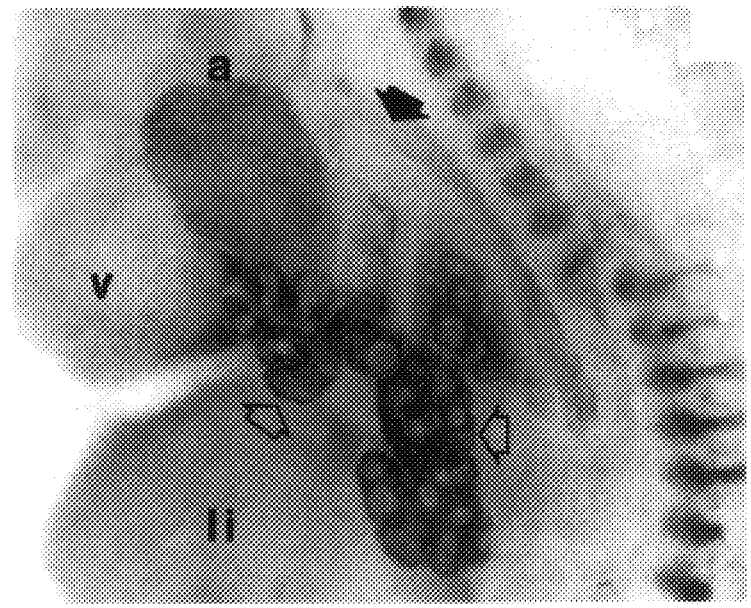
Figure 12F:
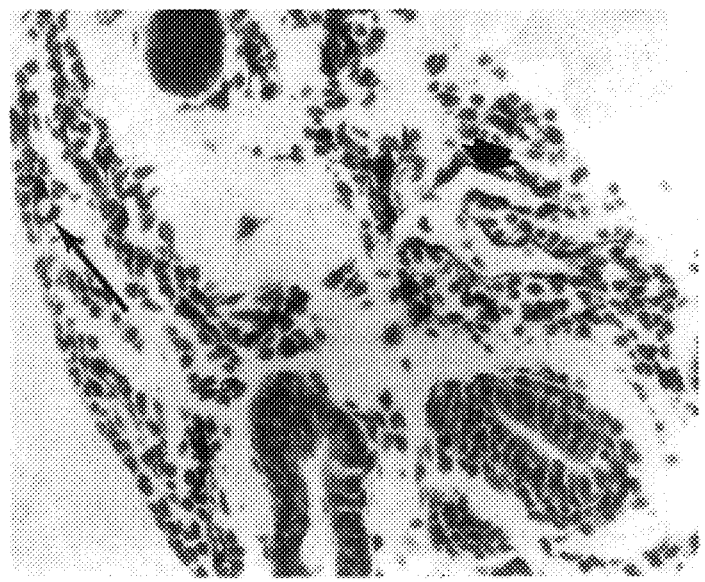
Figure 12G:
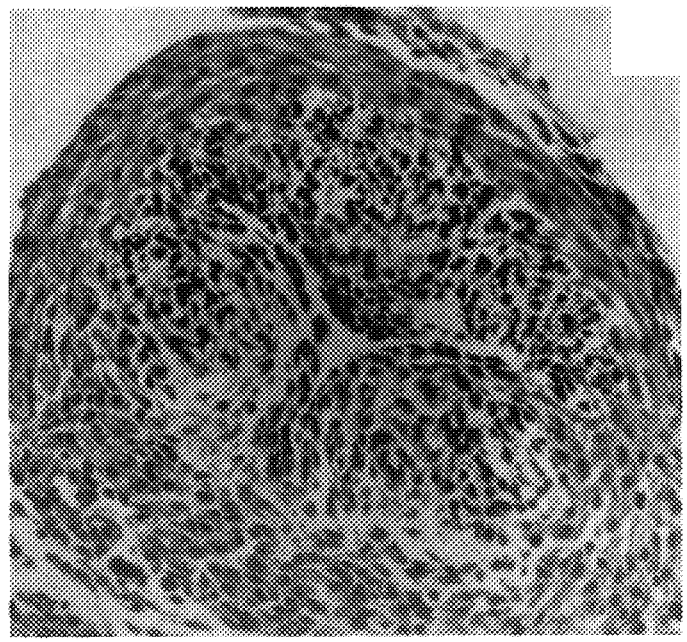
Figure 12H:
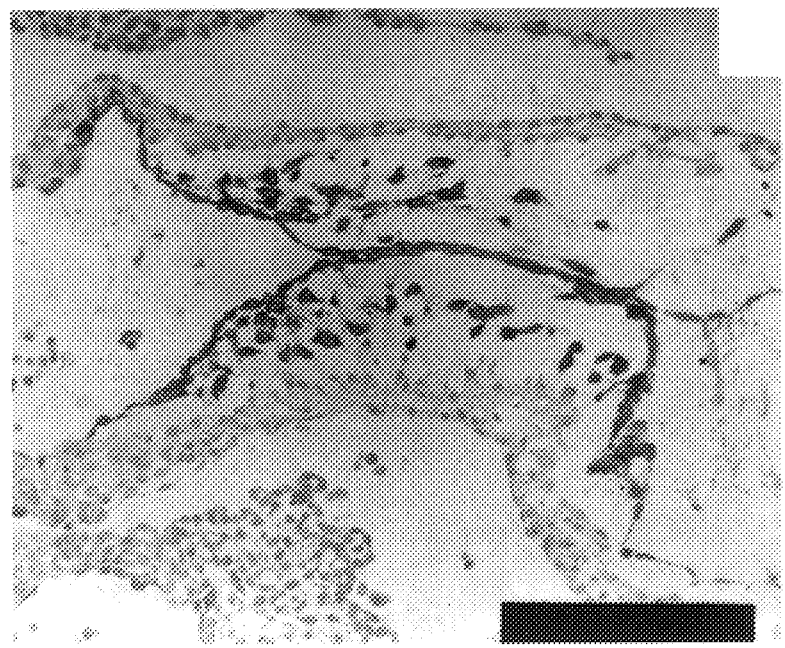

LacZ staining of embryos at day 13.5 of development was evaluated in the whole mount, and in sections made from paraffin embedded embryos. By this time, there was only patchy staining of endothelial cells in large vessels such as the aorta, whereas smaller vessels had virtually no staining (FIG. 12E). The only blood vessels which showed prominent lacZ staining at this stage were the pulmonary capillaries. The developing pulmonary vascular network stained intensely, making the entire lung appear grossly blue-green (FIG. 12E). Identification of the stained cells was made by microscopy of stained sections (FIG. 12F). Also, visualization of X-gal stained cells forming vascular channels was possible by viewing thick sections with Nomarski differential interference contrast optics. Organ vasculature associated the liver, brain and kidney showed no staining. In the heart, there was some residual staining of endothelial cells of the atrium. The majority of endothelial cells lining the ventricle no longer stained. The striking finding in the ventricle was that the cells forming the papillary muscle and the mitral valve showed marked staining. This labeling was seen not only in the endothelial cells on the surface, but in cells forming these structures. In a similar fashion, cells in the area of the forming valves of the aorta and pulmonary showed lacZ activity. Again, cells in the forming valve and in the wall of the vessel were stained (FIGS. 12G, 12H). The only non-cardiovascular staining was observed in cells in the areas of active bone formation. In particular, staining was most prominent in the proximal portions of the ribs, vertebrae, and the limb girdles (FIG. 12E). After 13.5 days, the only cells expressing the lacZ gene were pulmonary endothelial cells.

The aforementioned observations indicate that the protein encoded by the transcription unit in the del-1 locus is involved in early developmental processes in the cardiovascular system. This gene is not only a lineage marker, since it is expressed in restricted groups of endothelial cells in a temporally regulated fashion. The restricted expression seen at later stages indicates a connection with the origin of these endothelial cells, the mechanism of blood vessel formation, or the context-derived phenotype of these cells. Cells of the primordial endocardium express this marker, indicating a role in cardiogenesis. Most striking is the pattern of expression in the developing valvular apparatus of the heart. Competent endothelial cells in the forming septum and valves have been shown to undergo an epithelial-mesenchymal transformation. This transformation appears to be due, at least in part, to an inductive signal, such as transforming growth factor beta 3, which is released by the myocardium (Potts et al., 1991, *Proc. Natl. Acad. Sci. U.S.A.* 88:1516–1520; Sinning et al., 1992, *Anat. Rec.* 232:285–292). Reporter gene expression in the SLM275 mouse marked the competent cells of the endocardium which would respond to this signal, and expression appeared to persist for some time after the transformation (FIGS. 12G, 12H). This pattern of gene expression is unlike that described for any known molecule. Although the early endothelial expression pattern is similar to that characterized for the tyrosine kinases tek and flk-1 (Dumont et al., 1992, *Oncogene* 7:1471–1480; Millauer et al., 1993, *Cell* 72:835–846), there are striking differences at later stages which clearly indicate that lacZ expression in the transgenic animals marks a novel gene.

7.2.2. EXPRESSION ANALYSIS BY NORTHERN BLOT

Expression of del-1 in various fetal and adult tissues was examined by Northern blot analysis. A portion of the mouse cDNA clone (0.3 kb Sac I probe) was used as a probe on six poly A RNA filters purshased from Clontech Inc. Human fetal tissues which were undergoing vasculogenesis were positive (Tables 1 and 2). Also, the time course of expression in whole mouse embryos was consistent with the β-gal straining results observed in transgenic mice (Table 3). In general, adult tissues were negative, or only weakly positive, with the exception of adult brain. Mouse cDNA clones isolated from a brain cDNA library appeared to be identical to the embryonic del-1 (Table 4). Two human cancer cell lines tested were weakly positive (Table 5). The results of Northern blot analysis were basically consistent with the pattern for a gene which was specifically active during endothelial cell development.

TABLE 1

| Human Adult | |
| --- | --- |
| heart | + |
| brain | ++++ |
| placenta | − |
| lung | − |
| liver | − |
| spleen | − |
| thymus | − |
| prostate | − |

TABLE 1-continued

Human Adult

| | |
|---|---|
| testis | − |
| ovary | + |
| skeletal muscle | − |
| kidney | − |
| pancreas | − |
| small intestine | + |
| colon | − |
| peripheral blood leukocyte | +/− |

TABLE 2

Human Fetal

| | |
|---|---|
| brain | +++ |
| lung | +++ |
| liver | + |
| kidney | ++ |

(Pooled from 17–26 wks)

TABLE 3

Mouse Embryo

| | |
|---|---|
| 7-day | − |
| 11-day | ++ |
| 15-day | +++ |
| 17-day | ++ |

TABLE 4

Mouse Adult

| | |
|---|---|
| heart | − |
| brain | − |
| spleen | + |
| lung | − |
| liver | − |
| skeletal muscle | − |
| kidney | − |

TABLE 5

Human Cancer Cell

| | |
|---|---|
| Promyelocytic leukemia HL60 | +/− |
| HeLa cell S3 | + |
| chronic myelogenous leukemia K-562 | − |
| lymphoblastic leukemia MOLT4 | − |
| Burkit's lymphoma Raji | − |
| colorectal adenocarcinoma SW480 | − |
| lung carcinoma A549 | |
| melanoma G361 | − |

7.2.3. EXPRESSION ANALYSIS BY RT-PCR

RNA from mouse yolk sac (day 8 through day 12) and mouse fetal liver (day 13 through day 18) were tested for del-1 expression by RT-PCR.

All tested samples were positive, consistent with the Northern blot analysis and results from β-gal staining in transgenic mice (Table 6). Several mouse yolk sac-derived cell lines were also tested by RT-PCR for expression of del-1. For comparison, several other cell lines and total d15 mouse fetal liver RNA samples were tested. All samples shown in Table 7 except ECV304 (a human endothelial cell line) were of mouse origin. The yolk sac-derived cell lines grown in long-term culture were not expressing del-1 at a detectable level. These cell cultures were not forming endothelial cell-like structures under these conditions. In contrast, an endothelial tumor line, EOMA, expressed high

TABLE 6

| Sample | Result |
|---|---|
| d8 Yolk Sac | + |
| d9 Yolk Sac | + |
| d10 Yolk Sac | + |
| d11 Yolk Sac | + |
| d12 Yolk Sac | + |
| d13 Fetal Liver | + |
| d14 Fetal Liver | + |
| d15 Fetal Liver | + |
| d16 Fetal Liver | + |
| d17 Fetal Liver | + |
| d18 Fetal Liver | + |

TABLE 7

| cell line | del-1 |
|---|---|
| 3T3 A31 | − |
| Sto 1 | ++ |
| YS4 | − |
| Pro135 | − |
| Pro175 | − |
| D-1 | − |
| A10 | − |
| ROSA02 | − |
| d15FL | ++ |
| EOMA | +++ |
| hECv304 | − |

8. DEPOSIT OF MICROORGANISMS

The following organisms were deposited with the American Type Culture Collection (ATCC), 12301 Parklawn Drive, Rockville, Md. 20852.

| Strain Designation | Accession No. |
|---|---|
| Hu DEL-1.Z1 | ATCC 97155 |
| Hu DEL-1.Z20 | ATCC 97154 |
| mus DEL-1.1 | |
| mus DEL-1.18 | |

The present invention is not to be limited in scope by the exemplified embodiments or deposited organisms which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

It is also to be understood that all base pair sizes given for nucleotides are approximate and are used for purposes of description.

What is claimed is:

1. An isolated polynucleotide, comprising a nucleotide sequence that hybridizes under stringent conditions to a second polynucleotide having a nucleotide sequence as shown in SEQ ID NO: 9 from residues #619 through #2058, or to the complementary sequence of the second polynucleotide, and which isolated polynucleotide encodes a naturally-occurring polypeptide.

2. The isolated polynucleotide of claim 1 that encodes a secreted polypeptide.

3. The isolated polynucleotide of claim 1 that encodes an extracellular matrix-associated polypeptide.

4. An isolated polynucleotide, comprising a nucleotide sequence that hybridizes under stringent conditions to a second polynucleotide having a nucleotide sequence as shown in SEQ ID NO: 11 from residues #184 through #1626, or to the complementary sequence of the second polynucleotide, and which isolated polynucleotide encodes a naturally-occurring polypeptide.

5. The isolated polynucleotide of claim 4 that encodes a secreted polypeptide.

6. The isolated polynucleotide of claim 4 that encodes an extracellular matrix-associated polypeptide.

7. An isolated polynucleotide, comprising a nucleotide sequence that hybridizes under stringent conditions to a second polynucleotide having a nucleotide sequence as shown in SEQ ID NO: 11 from residues #184 through #1626, with the exception that the nucleotide sequence from nucleotide #379 through #408 has been removed, or to the complementary sequence of the second polynucleotide, and which isolated polynucleotide encodes a naturally-occurring polypeptide.

8. The isolated polynucleotide of claim 7 that encodes a secreted polypeptide.

9. The isolated polynucleotide of claim 7 that encodes an extracellular matrix-associated polypeptide.

10. An isolated polynucleotide, comprising a nucleotide sequence that hybridizes under stringent conditions to a second polynucleotide having a nucleotide sequence as shown in SEQ ID NO: 28 from residues #550 through #1212, or to the complementary sequence of the second polynucleotide, and which isolated polynucleotide encodes a naturally-occurring polypeptide.

11. The isolated polynucleotide of claim 10 that encodes a secreted polypeptide.

12. The isolated polynucleotide of claim 10 that encodes an extracellular matrix-associated polypeptide.

13. An isolated polynucleotide, comprising a nucleotide sequence that encodes a polypeptide comprising the amino acid sequence as shown in SEQ ID NO: 10 from residue #22 through #480.

14. The polynucleotide of claim 13 in which the nucleotide sequence is shown in SEQ ID NO: 9 from nucleotide #682 through #2058.

15. An isolated polynucleotide, comprising a nucleotide sequence that encodes a polypeptide comprising the amino acid sequence as shown in SEQ ID NO: 10 from residue #1 through #480.

16. The polynucleotide of claim 15 in which the nucleotide sequence is shown in SEQ ID NO: 9 from nucleotide #619 through #2058.

17. An isolated polynucleotide, comprising a nucleotide sequence that encodes a polypeptide comprising the amino acid sequence as shown in SEQ ID NO: 29 from residue #22 through #221.

18. The-polynucleotide of claim 17 in which the nucleotide sequence is shown in SEQ ID NO:28 from nucleotide #613 through #1212.

19. An isolated polynucleotide, comprising a nucleotide sequence that encodes a polypeptide comprising the amino acid sequence as shown in SEQ ID NO:29 from residue #1 through #221.

20. The polynucleotide of claim 19 in which the nucleotide sequence is shown in SEQ ID NO:28 from nucleotide #550 through #1212.

21. An isolated polynucleotide, comprising a nucleotide sequence that encodes a polypeptide comprising the amino acid sequence as shown in SEQ ID NO:14 from residue #54 through #513.

22. The polynucleotide of claim 21 in which the nucleotide sequence is shown in SEQ ID NO:11 from nucleotide #247 through #1626.

23. An isolated polynucleotide, comprising a nucleotide sequence that encodes a polypeptide comprising the amino acid sequence as shown in SEQ ID NO:14 from residue #33 through #513.

24. The polynucleotide of claim 23 in which the nucleotide sequence is shown in SEQ ID NO:11 from nucleotide #184 through #1626.

25. An isolated polynucleotide, comprising a nucleotide sequence that encodes a polypeptide comprising the amino acid sequence as shown in SEQ ID NO:14 from residue #54 through #513, with the exception that the amino acid sequence from residue #98 through #107 has been removed.

26. The polynucleotide of claim 25 in which the nucleotide sequence is shown in SEQ ID NO:11 from nucleotide #247 through #1626, with the exception that the nucleotide sequence from nucleotide #379 through #408 has been removed.

27. An isolated polynucleotide, comprising a nucleotide sequence that encodes a polypeptide comprising the amino acid sequence as shown in SEQ ID NO:14 from residue #33 through #513, with the exception that the amino acid sequence from residue #98 through #107 has been removed.

28. The polynucleotide of claim 27 in which the nucleotide sequence is shown in SEQ ID NO:11 from nucleotide #184 through #1626, with the exception that the nucleotide sequence from nucleotide #379 through #408 has been removed.

29. The polynucleotide of any one of claims 1–9, 10–15, 21, 23, 25, 27, 17, and 19 which is not naturally-occuring.

30. The polynucleotide of any one of claims 1–9, 10–15, 18, 20–28, 17, and 19 which is chemically synthesized.

31. The polynucleotide of any one of claims 1–16, 18, 20, 28, 17 and 19 which is DNA.

32. The polynucleotide of claim 31 which is cDNA.

33. The polynucleotide of any one of claims 1–9, 10–15, 21, 23, 25, 27, 17 and 19 which is RNA.

34. A recombinant vector containing the polynucleotide of any one of claims 1–16, 18, 20, 28, 17 and 19.

35. A recombinant expression vector containing the polynucleotide of any one of claims 1–16, 18, 20, 28, 17, and 19 in which the nucleotide sequence of the polynucleotide is operatively associated with a regulatory sequence that controls expression of the polynucleotide in a host cell.

36. A genetically-engineered host cell containing the polynucleotide of any one of claims 1–16, 18, 20, 28, 17, 19 or progeny thereof.

37. A genetically-engineered host cell containing the polynucleotide of any one of claims 1–16, 18, 20, 28, 17 and 19 in which the nucleotide sequence of the polynucleotide is operatively associated with a regulatory sequence that controls expression of the polynucleotide in a host cell, or progeny thereof.

38. The genetically-engineered host cell of claim 37 which is a prokaryote.

39. A method for producing a polypeptide, comprising:
(a) culturing the genetically-engineered host cell of claim 38; and
(b) recovering the polypeptide from the cultured host cell or its culture medium.

40. The genetically-engineered host cell of claim 37 which is an eukaryote.

41. A method for producing a polypeptide, comprising:
(a) culturing the genetically-engineered host cell of claim 40; and
(b) recovering the polypeptide from the cultured host cell or its culture medium.

* * * * *

UNITED STATES PATENT AND TRADEMARK OFFICE
CERTIFICATE OF CORRECTION

PATENT NO. : 5,874,562
DATED : February 23, 1999
INVENTOR(S) : Thomas Quertermous, et al.

It is certified that error appears in the above-identified patent and that said Letters Patent is hereby corrected as shown below:

Column 23, line 29, change "3E" to --3D--.

Column 24, line 14, change "11E" to --11D--.

Signed and Sealed this

Eighth Day of June, 1999

Attest:

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 85 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:1:

```
Asp Leu Leu Val Pro Thr Lys Val Thr Gly Ile Ile Thr Gln Gly Xaa
 1               5                  10                  15
Xaa Ala Lys Asp Phe Gly Asp Val Leu Phe Val Gly Ser Tyr Lys Leu
            20                  25                  30
Ala Tyr Ser Asn Asp Gly Glu His Trp Met Val His Gln Asp Glu Lys
        35                  40                  45
Gln Arg Lys Asp Lys Val Phe Gln Gly Asn Phe Asp Asn Asp Thr His
    50                  55                  60
Arg Lys Asn Val Ile Asp Pro Pro Ile Tyr Ala Arg Phe Ile Arg Ile
65                  70                  75                  80
Leu Pro Leu Xaa Xaa
                85
```

( 2 ) INFORMATION FOR SEQ ID NO:2:

( i ) SEQUENCE CHARACTERISTICS:
        ( A ) LENGTH: 85 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:2:

```
Asp Leu Gly Ser Ser Lys Glu Val Thr Gly Ile Ile Thr Gln Gly Xaa
 1               5                  10                  15
Xaa Ala Arg Asn Phe Gly Ser Val Gln Phe Val Ala Ser Tyr Lys Val
            20                  25                  30
Ala Tyr Ser Asn Asp Ser Ala Asn Trp Thr Glu Tyr Gln Asp Pro Arg
        35                  40                  45
Thr Gly Ser Ser Lys Val Phe Gln Gly Asn Leu Asp Asn Asn Ser His
    50                  55                  60
Lys Lys Asn Ile Phe Glu Lys Pro Phe Met Ala Arg Tyr Val Arg Val
65                  70                  75                  80
Leu Pro Val Xaa Xaa
                85
```

( 2 ) INFORMATION FOR SEQ ID NO:3:

( i ) SEQUENCE CHARACTERISTICS:
        ( A ) LENGTH: 85 amino acids
        ( B ) TYPE: amino acid
        ( C ) STRANDEDNESS:
        ( D ) TOPOLOGY: unknown ( i i ) MOLECULE TYPE: peptide (xi) SEQUENCE DESCRIPTION: SEQ ID NO:3:

| Asp | Leu | Leu | Lys | Ile | Lys | Lys | Ile | Thr | Ala | Ile | Ile | Thr | Gln | Gly | Xaa |
| --- | --- | --- | --- | --- | --- | --- | --- | --- | --- | --- | --- | --- | --- | --- | --- |
| 1 | | | | 5 | | | | | 10 | | | | | | 15 |
| Xaa | Cys | Lys | Ser | Leu | Ser | Ser | Glu | Met | Tyr | Val | Lys | Ser | Tyr | Thr | Ile |
| | | | 20 | | | | | 25 | | | | | 30 | | |
| His | Tyr | Ser | Glu | Gln | Gly | Val | Glu | Trp | Lys | Pro | Tyr | Arg | Leu | Lys | Ser |
| | | 35 | | | | | 40 | | | | | 45 | | | |
| Ser | Met | Val | Asp | Lys | Ile | Phe | Glu | Gly | Asn | Thr | Asn | Thr | Lys | Gly | His |
| | 50 | | | | | 55 | | | | | 60 | | | | |
| Val | Lys | Asn | Phe | Phe | Asn | Pro | Pro | Ile | Ile | Ser | Arg | Phe | Ile | Arg | Val |
| 65 | | | | | 70 | | | | | 75 | | | | | 80 |
| Ile | Pro | Lys | Xaa | Xaa | | | | | | | | | | | |
| | | | | 85 | | | | | | | | | | | |

(2) INFORMATION FOR SEQ ID NO:4:

(i) SEQUENCE CHARACTERISTICS:
  (A) LENGTH: 85 amino acids
  (B) TYPE: amino acid
  (C) STRANDEDNESS:
  (D) TOPOLOGY: unknown (ii) MOLECULE TYPE: peptide (xi) SEQUENCE DESCRIPTION: SEQ ID NO:4:

| Asp | Leu | Gln | Lys | Thr | Met | Lys | Val | Thr | Gly | Ile | Ile | Thr | Gln | Gly | Xaa |
| --- | --- | --- | --- | --- | --- | --- | --- | --- | --- | --- | --- | --- | --- | --- | --- |
| 1 | | | | 5 | | | | | 10 | | | | | | 15 |
| Xaa | Val | Lys | Ser | Leu | Phe | Thr | Ser | Met | Phe | Val | Lys | Glu | Phe | Leu | Ile |
| | | | 20 | | | | | 25 | | | | | 30 | | |
| Ser | Ser | Ser | Gln | Asp | Gly | His | His | Trp | Thr | Xaa | Xaa | Gln | Ile | Leu | Tyr |
| | | 35 | | | | | 40 | | | | | 45 | | | |
| Asn | Gly | Lys | Val | Lys | Val | Phe | Gln | Gly | Asn | Gln | Asp | Ser | Ser | Thr | Pro |
| | 50 | | | | | 55 | | | | | 60 | | | | |
| Met | Met | Asn | Ser | Leu | Asp | Pro | Pro | Leu | Leu | Thr | Arg | Xaa | Xaa | Xaa | Xaa |
| 65 | | | | | 70 | | | | | 75 | | | | | 80 |
| Xaa | Xaa | Xaa | Xaa | Xaa | | | | | | | | | | | |
| | | | | 85 | | | | | | | | | | | |

(2) INFORMATION FOR SEQ ID NO:5:

(i) SEQUENCE CHARACTERISTICS:
  (A) LENGTH: 85 amino acids
  (B) TYPE: amino acid
  (C) STRANDEDNESS:
  (D) TOPOLOGY: unknown (ii) MOLECULE TYPE: peptide (xi) SEQUENCE DESCRIPTION: SEQ ID NO:5:

| Asp | Leu | Glu | Asn | Leu | Arg | Phe | Val | Ser | Gly | Ile | Gly | Thr | Gln | Gly | Ala |
| --- | --- | --- | --- | --- | --- | --- | --- | --- | --- | --- | --- | --- | --- | --- | --- |
| 1 | | | | 5 | | | | | 10 | | | | | | 15 |
| Ile | Ser | Lys | Glu | Thr | Lys | Lys | Tyr | Phe | Val | Lys | Ser | Tyr | Lys | Val | |
| | | | 20 | | | | | 25 | | | | | 30 | | |
| Asp | Ile | Ser | Ser | Asn | Gly | Glu | Asp | Trp | Ile | Xaa | Xaa | Thr | Leu | Lys | Gly |
| | | 35 | | | | | 40 | | | | | 45 | | | |
| Asp | Asn | Lys | His | Leu | Val | Phe | Thr | Gly | Asn | Thr | Asp | Ala | Thr | Asp | Val |
| | 50 | | | | | 55 | | | | | 60 | | | | |
| Val | Tyr | Arg | Pro | Phe | Ser | Lys | Pro | Val | Ile | Thr | Arg | Phe | Val | Arg | Leu |
| 65 | | | | | 70 | | | | | 75 | | | | | 80 |
| Arg | Pro | Val | Thr | Trp | | | | | | | | | | | |

85

(2) INFORMATION FOR SEQ ID NO:6:

(i) SEQUENCE CHARACTERISTICS:
        (A) LENGTH: 85 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:6:

```
Asp Leu Ala Glu Glu Lys Ile Val Arg Gly Val Ile Ile Gln Gly Xaa
 1               5                  10                  15
Xaa Gly Lys His Lys Glu Asn Lys Val Phe Met Arg Lys Phe Lys Ile
             20                  25                  30
Gly Tyr Ser Asn Asn Gly Thr Glu Trp Glu Met Ile Met Asp Ser Ser
             35                  40                  45
Lys Asn Lys Pro Lys Thr Phe Glu Gly Asn Thr Asn Tyr Asp Thr Pro
         50                  55                  60
Glu Leu Arg Thr Phe Xaa Ala His Ile Thr Thr Gly Phe Ile Arg Ile
 65                  70                  75                  80
Ile Pro Xaa Xaa Xaa
             85
```

(2) INFORMATION FOR SEQ ID NO:7:

(i) SEQUENCE CHARACTERISTICS:
        (A) LENGTH: 85 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:7:

```
Gly Cys Glu Val Pro Arg Thr Phe Met Cys Val Ala Leu Gln Gly Xaa
 1               5                  10                  15
Xaa Xaa Arg Gly Xaa Asp Ala Asp Gln Trp Val Thr Ser Tyr Lys Ile
             20                  25                  30
Arg Tyr Ser Leu Asp Asn Val Ser Trp Phe Xaa Xaa Xaa Xaa Glu
             35                  40                  45
Tyr Arg Asn Gly Ala Ala Ile Thr Gly Val Thr Asp Arg Asn Thr Val
         50                  55                  60
Val Asn His Phe Phe Asp Thr Pro Ile Arg Ala Arg Ser Ile Ala Ile
 65                  70                  75                  80
His Pro Leu Thr Xaa
             85
```

(2) INFORMATION FOR SEQ ID NO:8:

(i) SEQUENCE CHARACTERISTICS:
        (A) LENGTH: 85 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:8:

```
Asp Leu Xaa Xaa Xaa Xaa Xaa Val Thr Gly Ile Ile Thr Gln Gly Xaa
 1               5                  10                  15
```

Xaa Xaa Lys Xaa Xaa Xaa Xaa Xaa Xaa Phe Val Xaa Ser Tyr Lys Ile
         20                   25                  30

Xaa Tyr Ser Xaa Asp Gly Xaa Xaa Trp Xaa Xaa Xaa Xaa Xaa Xaa Xaa
         35              40                  45

Xaa Xaa Lys Xaa Lys Val Phe Xaa Gly Asn Thr Asp Xaa Xaa Thr Xaa
     50              55                  60

Xaa Xaa Asn Xaa Phe Xaa Xaa Pro Ile Xaa Xaa Arg Phe Ile Arg Xaa
 65              70              75                          80

Xaa Pro Xaa Xaa Xaa
             85

( 2 ) INFORMATION FOR SEQ ID NO:9:

( i ) SEQUENCE CHARACTERISTICS:
        ( A ) LENGTH: 2303 base pairs
        ( B ) TYPE: nucleic acid
        ( C ) STRANDEDNESS: single
        ( D ) TOPOLOGY: unknown ( i i ) MOLECULE TYPE: cDNA ( i x ) FEATURE:
        ( A ) NAME/KEY: CDS
        ( B ) LOCATION: 619..2058

( x i ) SEQUENCE DESCRIPTION: SEQ ID NO:9:

```
GAATTCCGGT  TAACTGAGGA  CAAAGGGTAA  TGCAGAAGTG  ATATTTGATT  TCCATTCTCA     60

TTCCCAGTGG  CCTTGATATT  TAAACTGATT  CCTGCCACCA  GGTCCTTGGG  CCACCCTGTC    120

CCTGCGTCTC  ATATTTCTGC  ATGCTGCTTT  GTTTGTATAT  AGTGCGCTCC  TGGCCTCAGG    180

CTCGCTCCCC  TCCAGCTCTC  GCTTCATTGT  TCTCCAAGTC  AGAAGCCCCC  GCATCCGCCG    240

CGCAGCAGCG  TGAGCCGTAG  TCACTGCTGG  CCGCTTCGCC  TGCGTGCGCG  CACGGAAATC    300

GGGGAGCCAG  GAACCCAAGG  AGCCGCCGTC  CGCCCGCTGT  GCCTCTGCTA  GACCACTCGC    360

AGCCCCAGCC  TCTCTCAAGC  GCACCCACCT  CCGCGCACCC  CAGCTCAGGC  GAAGCTGGAG    420

TGAGGGTGAA  TCACCCTTTC  TCTAGGGCCA  CCACTCTTTT  ATCGCCCTTC  CCAAGATTTG    480

AGAAGCGCTG  CGGGAGGAAA  GACGTCCTCT  TGATCTCTGA  CAGGGCGGGG  TTTACTGCTG    540

TCCTGCAGGC  GCGCCTCGCC  TACTGTGCCC  TCCGCTACGA  CCCCGGACCA  GCCCAGGTCA    600
```

CGTCCGTGAG   AAGGGATC   ATG   AAG   CAC   TTG   GTA   GCA   GCC   TGG   CTT   TTG   GTT       651
                        Met   Lys   His   Leu   Val   Ala   Ala   Trp   Leu   Leu   Val
                         1                  5                              10

GGA   CTC   AGC   CTC   GGG   GTG   CCC   CAG   TTC   GGC   AAA   GGT   GAC   ATT   TGC   AAC   699
Gly   Leu   Ser   Leu   Gly   Val   Pro   Gln   Phe   Gly   Lys   Gly   Asp   Ile   Cys   Asn
                  15                        20                        25

CCG   AAC   CCC   TGT   GAA   AAT   GGT   GGC   ATC   TGT   CTG   TCA   GGA   CTG   GCT   GAT   747
Pro   Asn   Pro   Cys   Glu   Asn   Gly   Gly   Ile   Cys   Leu   Ser   Gly   Leu   Ala   Asp
            30                              35                              40

GAT   TCC   TTT   TCC   TGT   GAG   TGT   CCA   GAA   GGC   TTC   GCA   GGT   CCG   AAC   TGC   795
Asp   Ser   Phe   Ser   Cys   Glu   Cys   Pro   Glu   Gly   Phe   Ala   Gly   Pro   Asn   Cys
      45                              50                              55

TCT   AGT   GTT   GTG   GAG   GTT   GCA   TCA   GAT   GAA   GAA   AAG   CCT   ACT   TCA   GCA   843
Ser   Ser   Val   Val   Glu   Val   Ala   Ser   Asp   Glu   Glu   Lys   Pro   Thr   Ser   Ala
 60                        65                        70                        75

GGT   CCC   TGC   ATC   CCT   AAC   CCA   TGC   CAT   AAC   GGA   GGA   ACC   TGT   GAG   ATA   891
Gly   Pro   Cys   Ile   Pro   Asn   Pro   Cys   His   Asn   Gly   Gly   Thr   Cys   Glu   Ile
                        80                              85                              90

AGC   GAA   GCC   TAT   CGA   GGA   GAC   ACA   TTC   ATA   GGC   TAT   GTT   TGT   AAA   TGT   939
Ser   Glu   Ala   Tyr   Arg   Gly   Asp   Thr   Phe   Ile   Gly   Tyr   Val   Cys   Lys   Cys
                  95                              100                           105

| | | | | | | | | | | | | | | | | |
|---|---|---|---|---|---|---|---|---|---|---|---|---|---|---|---|---|
| CCT | CGG | GGA | TTT | AAT | GGG | ATT | CAC | TGT | CAG | CAC | AAT | ATA | AAT | GAA | TGT | 987 |
| Pro | Arg | Gly | Phe | Asn | Gly | Ile | His | Cys | Gln | His | Asn | Ile | Asn | Glu | Cys | |
| | 110 | | | | | 115 | | | | | 120 | | | | | |
| GAA | GCT | GAG | CCT | TGC | AGA | AAT | GGC | GGA | ATA | TGT | ACC | GAC | CTT | GTT | GCT | 1035 |
| Glu | Ala | Glu | Pro | Cys | Arg | Asn | Gly | Gly | Ile | Cys | Thr | Asp | Leu | Val | Ala | |
| 125 | | | | | 130 | | | | | 135 | | | | | | |
| AAC | TAC | TCT | TGT | GAA | TGC | CCA | GGA | GAA | TTT | ATG | GGA | CGA | AAT | TGT | CAA | 1083 |
| Asn | Tyr | Ser | Cys | Glu | Cys | Pro | Gly | Glu | Phe | Met | Gly | Arg | Asn | Cys | Gln | |
| 140 | | | | | 145 | | | | | 150 | | | | | 155 | |
| TAT | AAA | TGC | TCT | GGG | CAC | TTG | GGA | ATC | GAA | GGT | GGG | ATC | ATA | TCT | AAT | 1131 |
| Tyr | Lys | Cys | Ser | Gly | His | Leu | Gly | Ile | Glu | Gly | Gly | Ile | Ile | Ser | Asn | |
| | | | | 160 | | | | | 165 | | | | | 170 | | |
| CAG | CAA | ATC | ACA | GCT | TCA | TCT | AAT | CAC | CGA | GCT | CTT | TTT | GGA | CTC | CAG | 1179 |
| Gln | Gln | Ile | Thr | Ala | Ser | Ser | Asn | His | Arg | Ala | Leu | Phe | Gly | Leu | Gln | |
| | | | 175 | | | | | 180 | | | | | 185 | | | |
| AAG | TGG | TAT | CCC | TAC | TAT | GCT | CGA | CTT | AAT | AAG | AAG | GGC | CTT | ATA | AAT | 1227 |
| Lys | Trp | Tyr | Pro | Tyr | Tyr | Ala | Arg | Leu | Asn | Lys | Lys | Gly | Leu | Ile | Asn | |
| | | 190 | | | | | 195 | | | | | 200 | | | | |
| GCC | TGG | ACA | GCT | GCT | GAA | AAT | GAC | AGA | TGG | CCA | TGG | ATT | CAG | ATA | AAT | 1275 |
| Ala | Trp | Thr | Ala | Ala | Glu | Asn | Asp | Arg | Trp | Pro | Trp | Ile | Gln | Ile | Asn | |
| | 205 | | | | | 210 | | | | | 215 | | | | | |
| TTG | CAA | AGA | AAA | ATG | AGA | GTC | ACT | GGT | GTT | ATT | ACC | CAA | GGA | GCA | AAA | 1323 |
| Leu | Gln | Arg | Lys | Met | Arg | Val | Thr | Gly | Val | Ile | Thr | Gln | Gly | Ala | Lys | |
| 220 | | | | | 225 | | | | | 230 | | | | | 235 | |
| AGG | ATT | GGA | AGC | CCA | GAG | TAC | ATA | AAA | TCC | TAC | AAA | ATT | GCC | TAC | AGC | 1371 |
| Arg | Ile | Gly | Ser | Pro | Glu | Tyr | Ile | Lys | Ser | Tyr | Lys | Ile | Ala | Tyr | Ser | |
| | | | | 240 | | | | | 245 | | | | | 250 | | |
| AAT | GAC | GGG | AAG | ACC | TGG | GCA | ATG | TAC | AAA | GTA | AAA | GGC | ACC | AAT | GAA | 1419 |
| Asn | Asp | Gly | Lys | Thr | Trp | Ala | Met | Tyr | Lys | Val | Lys | Gly | Thr | Asn | Glu | |
| | | | 255 | | | | | 260 | | | | | 265 | | | |
| GAG | ATG | GTC | TTT | CGT | GGA | AAT | GTT | GAT | AAC | AAC | ACA | CCA | TAT | GCT | AAT | 1467 |
| Glu | Met | Val | Phe | Arg | Gly | Asn | Val | Asp | Asn | Asn | Thr | Pro | Tyr | Ala | Asn | |
| | | 270 | | | | | 275 | | | | | 280 | | | | |
| TCT | TTC | ACA | CCC | CCA | ATC | AAA | GCT | CAG | TAT | GTA | AGA | CTC | TAC | CCC | CAA | 1515 |
| Ser | Phe | Thr | Pro | Pro | Ile | Lys | Ala | Gln | Tyr | Val | Arg | Leu | Tyr | Pro | Gln | |
| | 285 | | | | | 290 | | | | | 295 | | | | | |
| ATT | TGT | CGA | AGG | CAT | TGT | ACT | TTA | AGA | ATG | GAA | CTT | CTT | GGC | TGT | GAG | 1563 |
| Ile | Cys | Arg | Arg | His | Cys | Thr | Leu | Arg | Met | Glu | Leu | Leu | Gly | Cys | Glu | |
| 300 | | | | | 305 | | | | | 310 | | | | | 315 | |
| CTC | TCA | GGC | TGT | TCA | GAA | CCT | TTG | GGG | ATG | AAA | TCA | GGG | CAT | ATA | CAA | 1611 |
| Leu | Ser | Gly | Cys | Ser | Glu | Pro | Leu | Gly | Met | Lys | Ser | Gly | His | Ile | Gln | |
| | | | | 320 | | | | | 325 | | | | | 330 | | |
| GAC | TAC | CAG | ATC | ACT | GCC | TCC | AGC | GTC | TTC | AGA | ACA | CTC | AAC | ATG | GAC | 1659 |
| Asp | Tyr | Gln | Ile | Thr | Ala | Ser | Ser | Val | Phe | Arg | Thr | Leu | Asn | Met | Asp | |
| | | | 335 | | | | | 340 | | | | | 345 | | | |
| ATG | TTT | ACT | TGG | GAA | CCA | AGG | AAA | GCC | AGG | CTG | GAC | AAG | CAA | GGC | AAA | 1707 |
| Met | Phe | Thr | Trp | Glu | Pro | Arg | Lys | Ala | Arg | Leu | Asp | Lys | Gln | Gly | Lys | |
| | | 350 | | | | | 355 | | | | | 360 | | | | |
| GTA | AAT | GCC | TGG | ACT | TCC | GGC | CAT | AAC | GAC | CAG | TCA | CAA | TGG | TTA | CAG | 1755 |
| Val | Asn | Ala | Trp | Thr | Ser | Gly | His | Asn | Asp | Gln | Ser | Gln | Trp | Leu | Gln | |
| | 365 | | | | | 370 | | | | | 375 | | | | | |
| GTT | GAT | CTT | CTT | GTC | CCT | ACT | AAG | GTG | ACA | GGC | ATC | ATT | ACA | CAA | GGA | 1803 |
| Val | Asp | Leu | Leu | Val | Pro | Thr | Lys | Val | Thr | Gly | Ile | Ile | Thr | Gln | Gly | |
| 380 | | | | | 385 | | | | | 390 | | | | | 395 | |
| GCT | AAA | GAT | TTT | GGT | CAC | GTG | CAG | TTT | GTT | GGG | TCA | TAC | AAA | CTA | GCT | 1851 |
| Ala | Lys | Asp | Phe | Gly | His | Val | Gln | Phe | Val | Gly | Ser | Tyr | Lys | Leu | Ala | |
| | | | | 400 | | | | | 405 | | | | | 410 | | |
| TAC | AGC | AAT | GAT | GGA | GAA | CAC | TGG | ATG | GTG | CAC | CAG | GAT | GAA | AAA | CAG | 1899 |
| Tyr | Ser | Asn | Asp | Gly | Glu | His | Trp | Met | Val | His | Gln | Asp | Glu | Lys | Gln | |
| | | | 415 | | | | | 420 | | | | | 425 | | | |

-continued

```
AGG AAA GAC AAG GTT TTT CAA GGC AAT TTT GAC AAT GAC ACT CAC AGG            1947
Arg Lys Asp Lys Val Phe Gln Gly Asn Phe Asp Asn Asp Thr His Arg
        430                 435                 440

AAA AAT GTC ATC GAC CCT CCC ATC TAT GCA CGA TTC ATA AGA ATC CTT            1995
Lys Asn Val Ile Asp Pro Pro Ile Tyr Ala Arg Phe Ile Arg Ile Leu
    445                 450                 455

CCT TGG TCC TGG TAT GGA AGG ATC ACT CTG CGG TCA GAG CTG CTG GGC            2043
Pro Trp Ser Trp Tyr Gly Arg Ile Thr Leu Arg Ser Glu Leu Leu Gly
460                 465                 470                 475

TGC GCA GAG GAG GAA TGAAGTGCGG GGCCGCACAT CCCACAATGC TTTTCTTTAT            2098
Cys Ala Glu Glu Glu
                480

TTTCCTATAA GTATCCCAC GAAATGAACT GTGTGAAGCT GATGGAAACT GCATTTGTTT           2158

TTTTCAAAGT GTTCAAATTA TGGTAGGCTA CTGACTGTCT TTTTAGGAGT TCTAAGCTTG          2218

CCTTTTTAAT AATTTAATTT GGTTTCCTTT GCTCAACTCT CTTATGTAAT ATCACACTGT          2278

CTGTGAGTTA CTCTTCTTGT TCTCT                                                2303
```

( 2 ) INFORMATION FOR SEQ ID NO:10:

( i ) SEQUENCE CHARACTERISTICS:
        ( A ) LENGTH: 480 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Lys His Leu Val Ala Ala Trp Leu Leu Val Gly Leu Ser Leu Gly
 1               5                  10                  15

Val Pro Gln Phe Gly Lys Gly Asp Ile Cys Asn Pro Asn Pro Cys Glu
            20                  25                  30

Asn Gly Gly Ile Cys Leu Ser Gly Leu Ala Asp Asp Ser Phe Ser Cys
        35                  40                  45

Glu Cys Pro Glu Gly Phe Ala Gly Pro Asn Cys Ser Ser Val Val Glu
    50                  55                  60

Val Ala Ser Asp Glu Glu Lys Pro Thr Ser Ala Gly Pro Cys Ile Pro
65                  70                  75                  80

Asn Pro Cys His Asn Gly Gly Thr Cys Glu Ile Ser Glu Ala Tyr Arg
                85                  90                  95

Gly Asp Thr Phe Ile Gly Tyr Val Cys Lys Cys Pro Arg Gly Phe Asn
            100                 105                 110

Gly Ile His Cys Gln His Asn Ile Asn Glu Cys Glu Ala Glu Pro Cys
        115                 120                 125

Arg Asn Gly Gly Ile Cys Thr Asp Leu Val Ala Asn Tyr Ser Cys Glu
    130                 135                 140

Cys Pro Gly Glu Phe Met Gly Arg Asn Cys Gln Tyr Lys Cys Ser Gly
145                 150                 155                 160

His Leu Gly Ile Glu Gly Gly Ile Ile Ser Asn Gln Ile Thr Ala
                165                 170                 175

Ser Ser Asn His Arg Ala Leu Phe Gly Leu Gln Lys Trp Tyr Pro Tyr
            180                 185                 190

Tyr Ala Arg Leu Asn Lys Lys Gly Leu Ile Asn Ala Trp Thr Ala Ala
        195                 200                 205

Glu Asn Asp Arg Trp Pro Trp Ile Gln Ile Asn Leu Gln Arg Lys Met
    210                 215                 220

Arg Val Thr Gly Val Ile Thr Gln Gly Ala Lys Arg Ile Gly Ser Pro
225                 230                 235                 240
```

-continued

| | | | | | | | | | | | | | | | |
|---|---|---|---|---|---|---|---|---|---|---|---|---|---|---|---|
| Glu | Tyr | Ile | Lys | Ser | Tyr | Lys | Ile | Ala | Tyr | Ser | Asn | Asp | Gly | Lys | Thr |
| | | | | 245 | | | | | 250 | | | | | 255 | |
| Trp | Ala | Met | Tyr | Lys | Val | Lys | Gly | Thr | Asn | Glu | Glu | Met | Val | Phe | Arg |
| | | | 260 | | | | | 265 | | | | | 270 | | |
| Gly | Asn | Val | Asp | Asn | Asn | Thr | Pro | Tyr | Ala | Asn | Ser | Phe | Thr | Pro | Pro |
| | | 275 | | | | | 280 | | | | | 285 | | | |
| Ile | Lys | Ala | Gln | Tyr | Val | Arg | Leu | Tyr | Pro | Gln | Ile | Cys | Arg | Arg | His |
| | 290 | | | | | 295 | | | | | 300 | | | | |
| Cys | Thr | Leu | Arg | Met | Glu | Leu | Leu | Gly | Cys | Glu | Leu | Ser | Gly | Cys | Ser |
| 305 | | | | | 310 | | | | | 315 | | | | | 320 |
| Glu | Pro | Leu | Gly | Met | Lys | Ser | Gly | His | Ile | Gln | Asp | Tyr | Gln | Ile | Thr |
| | | | | 325 | | | | | 330 | | | | | 335 | |
| Ala | Ser | Ser | Val | Phe | Arg | Thr | Leu | Asn | Met | Asp | Met | Phe | Thr | Trp | Glu |
| | | | 340 | | | | | 345 | | | | | 350 | | |
| Pro | Arg | Lys | Ala | Arg | Leu | Asp | Lys | Gln | Gly | Lys | Val | Asn | Ala | Trp | Thr |
| | | 355 | | | | | 360 | | | | | 365 | | | |
| Ser | Gly | His | Asn | Asp | Gln | Ser | Gln | Trp | Leu | Gln | Val | Asp | Leu | Leu | Val |
| | 370 | | | | | 375 | | | | | 380 | | | | |
| Pro | Thr | Lys | Val | Thr | Gly | Ile | Ile | Thr | Gln | Gly | Ala | Lys | Asp | Phe | Gly |
| 385 | | | | | 390 | | | | | 395 | | | | | 400 |
| His | Val | Gln | Phe | Val | Gly | Ser | Tyr | Lys | Leu | Ala | Tyr | Ser | Asn | Asp | Gly |
| | | | | 405 | | | | | 410 | | | | | 415 | |
| Glu | His | Trp | Met | Val | His | Gln | Asp | Glu | Lys | Gln | Arg | Lys | Asp | Lys | Val |
| | | | 420 | | | | | 425 | | | | | 430 | | |
| Phe | Gln | Gly | Asn | Phe | Asp | Asn | Asp | Thr | His | Arg | Lys | Asn | Val | Ile | Asp |
| | | 435 | | | | | 440 | | | | | 445 | | | |
| Pro | Pro | Ile | Tyr | Ala | Arg | Phe | Ile | Arg | Ile | Leu | Pro | Trp | Ser | Trp | Tyr |
| | 450 | | | | | 455 | | | | | 460 | | | | |
| Gly | Arg | Ile | Thr | Leu | Arg | Ser | Glu | Leu | Leu | Gly | Cys | Ala | Glu | Glu | Glu |
| 465 | | | | | 470 | | | | | 475 | | | | | 480 |

( 2 ) INFORMATION FOR SEQ ID NO:11:

( i ) SEQUENCE CHARACTERISTICS:
        ( A ) LENGTH: 1780 base pairs
        ( B ) TYPE: nucleic acid
        ( C ) STRANDEDNESS: single
        ( D ) TOPOLOGY: unknown ( i i ) MOLECULE TYPE: cDNA ( i x ) FEATURE:
        ( A ) NAME/KEY: CDS
        ( B ) LOCATION: 1..1779

( x i ) SEQUENCE DESCRIPTION: SEQ ID NO:11:

| | | | | | | | | | | | | | | | | |
|---|---|---|---|---|---|---|---|---|---|---|---|---|---|---|---|---|
| TCT | CTT | TAG | TCA | CCA | CTC | TCG | CCC | TCT | CCA | AGA | ATT | TGT | TTA | ACA | AAG | 48 |
| Ser | Leu | * | Ser | Pro | Leu | Ser | Pro | Ser | Pro | Arg | Ile | Cys | Leu | Thr | Lys | |
| 1 | | | | 5 | | | | | 10 | | | | | 15 | | |
| CGC | TGA | GGA | AAG | AGA | ACG | TCT | TCT | TGA | ATT | CTT | TAG | TAG | GGG | CGG | AGT | 96 |
| Arg | * | Gly | Lys | Arg | Thr | Ser | Ser | * | Ile | Leu | * | * | Gly | Arg | Ser | |
| | | | 20 | | | | | 25 | | | | | 30 | | | |
| CTG | CTG | CTG | CCC | TGC | GCT | GCC | ACC | TCG | GCT | ACA | CTG | CCC | TCC | GCG | ACG | 144 |
| Leu | Leu | Leu | Pro | Cys | Ala | Ala | Thr | Ser | Ala | Thr | Leu | Pro | Ser | Ala | Thr | |
| | | | 35 | | | | | 40 | | | | | 45 | | | |
| ACC | CCT | GAC | CAG | CCG | GGG | TCA | CGT | CCG | GGA | GAC | GGG | ATC | ATG | AAG | CGC | 192 |
| Thr | Pro | Asp | Gln | Pro | Gly | Ser | Arg | Pro | Gly | Asp | Gly | Ile | Met | Lys | Arg | |
| | 50 | | | | | 55 | | | | | 60 | | | | | |
| TCG | GTA | GCC | GTC | TGG | CTC | TTG | GTC | GGG | CTC | AGC | CTC | GGT | GTC | CCC | CAG | 240 |

```
Ser Val Ala Val Trp Leu Leu Val Gly Leu Ser Leu Gly Val Pro Gln
 65              70                  75                  80

TTC GGC AAA GGT GAT ATT TGT GAT CCC AAT CCA TGT GAA AAT GGA GGT        288
Phe Gly Lys Gly Asp Ile Cys Asp Pro Asn Pro Cys Glu Asn Gly Gly
             85                  90                  95

ATC TGT TTG CCA GGA TTG GCT GTA GGT TCC TTT TCC TGT GAG TGT CCA        336
Ile Cys Leu Pro Gly Leu Ala Val Gly Ser Phe Ser Cys Glu Cys Pro
            100                 105                 110

GAT GGC TTC ACA GAC CCC AAC TGT TCT AGT GTT GTG GAG GTT GCA TCA        384
Asp Gly Phe Thr Asp Pro Asn Cys Ser Ser Val Val Glu Val Ala Ser
            115                 120                 125

GAT GAA GAA GAA CCA ACT TCA GCA GGT CCC TGC ACT CCT AAT CCA TGC        432
Asp Glu Glu Glu Pro Thr Ser Ala Gly Pro Cys Thr Pro Asn Pro Cys
        130                 135                 140

CAT AAT GGA GGA ACC TGT GAA ATA AGT GAA GCA TAC CGA GGG GAT ACA        480
His Asn Gly Gly Thr Cys Glu Ile Ser Glu Ala Tyr Arg Gly Asp Thr
145                 150                 155                 160

TTC ATA GGC TAT GTT TGT AAA TGT CCC CGA GGA TTT AAT GGG ATT CAC        528
Phe Ile Gly Tyr Val Cys Lys Cys Pro Arg Gly Phe Asn Gly Ile His
                165                 170                 175

TGT CAG CAC AAC ATA AAT GAA TGC GAA GTT GAG CCT TGC AAA AAT GGT        576
Cys Gln His Asn Ile Asn Glu Cys Glu Val Glu Pro Cys Lys Asn Gly
            180                 185                 190

GGA ATA TGT ACA GAT CTT GTT GCT AAC TAT TCC TGT GAG TGC CCA GGC        624
Gly Ile Cys Thr Asp Leu Val Ala Asn Tyr Ser Cys Glu Cys Pro Gly
            195                 200                 205

GAA TTT ATG GGA AGA AAT TGT CAA TAC AAA TGC TCA GGC CCA CTG GGA        672
Glu Phe Met Gly Arg Asn Cys Gln Tyr Lys Cys Ser Gly Pro Leu Gly
        210                 215                 220

ATT GAA GGT GGA ATT ATA TCA AAC CAG CAA ATC ACA GCT TCC TCT ACT        720
Ile Glu Gly Gly Ile Ile Ser Asn Gln Gln Ile Thr Ala Ser Ser Thr
225                 230                 235                 240

CAC CGA GCT CTT TTT GGA CTC CAA AAA TGG TAT CCC TAC TAT GCA CGT        768
His Arg Ala Leu Phe Gly Leu Gln Lys Trp Tyr Pro Tyr Tyr Ala Arg
                245                 250                 255

CTT AAT AAG AAG GGG CTT ATA AAT GCG TGG ACA GCT GCA GAA AAT GAC        816
Leu Asn Lys Lys Gly Leu Ile Asn Ala Trp Thr Ala Ala Glu Asn Asp
            260                 265                 270

AGA TGG AAG CGG TGG ATT CAG ATA AAT TTG CAA AGA AAA ATG AGA GTT        864
Arg Trp Lys Arg Trp Ile Gln Ile Asn Leu Gln Arg Lys Met Arg Val
        275                 280                 285

ACT GGT GTG ATT ACC CAA GGG GCC AAG AGG ATT GGA AGC CCA GAG TAT        912
Thr Gly Val Ile Thr Gln Gly Ala Lys Arg Ile Gly Ser Pro Glu Tyr
        290                 295                 300

ATA AAA TTC TAC AAA ATT GCC TAC AGT AAT GAT GGA AAG ACT TGG GCA        960
Ile Lys Phe Tyr Lys Ile Ala Tyr Ser Asn Asp Gly Lys Thr Trp Ala
305                 310                 315                 320

ATG TAC AAA GTG AAA GGC ACC AAT GAA GAC ATG GTG TTT CGT GGA AAC       1008
Met Tyr Lys Val Lys Gly Thr Asn Glu Asp Met Val Phe Arg Gly Asn
                325                 330                 335

ATT GAT AAC AAC ACT CCA TAT GCT AAC TCT TTC ACA CCC CCA ATA AAA       1056
Ile Asp Asn Asn Thr Pro Tyr Ala Asn Ser Phe Thr Pro Pro Ile Lys
            340                 345                 350

GCT CAG TAT GTA AGA CTC TAT CCC CAA GTT TGT CGA AGA CAT TGC ACT       1104
Ala Gln Tyr Val Arg Leu Tyr Pro Gln Val Cys Arg Arg His Cys Thr
        355                 360                 365

TTG CGA ATG GAA CTT CTT GGC TGT GAA CTG TCG GGT TGT TCT GAG CCT       1152
Leu Arg Met Glu Leu Leu Gly Cys Glu Leu Ser Gly Cys Ser Glu Pro
370                 375                 380

CTG GGT ATG AAA TCA GGA CAT ATA CAA GAC TAT CAG ATC ACT GCC TCC       1200
```

| Leu | Gly | Met | Lys | Ser | Gly | His | Ile | Gln | Asp | Tyr | Gln | Ile | Thr | Ala | Ser | |
|---|---|---|---|---|---|---|---|---|---|---|---|---|---|---|---|---|
| 385 | | | | | 390 | | | | | 395 | | | | | 400 | |

| AGC | ATC | TTC | AGA | ACG | CTC | AAC | ATG | GAC | ATG | TTC | ACT | TGG | GAA | CCA | AGG | 1248 |
|---|---|---|---|---|---|---|---|---|---|---|---|---|---|---|---|---|
| Ser | Ile | Phe | Arg | Thr | Leu | Asn | Met | Asp | Met | Phe | Thr | Trp | Glu | Pro | Arg | |
| | | | | 405 | | | | | 410 | | | | | 415 | | |

| AAA | GCT | CGG | CTG | GAC | AAG | CAA | GGC | AAA | GTG | AAT | GCC | TGG | ACC | TCT | GGC | 1296 |
|---|---|---|---|---|---|---|---|---|---|---|---|---|---|---|---|---|
| Lys | Ala | Arg | Leu | Asp | Lys | Gln | Gly | Lys | Val | Asn | Ala | Trp | Thr | Ser | Gly | |
| | | | 420 | | | | | 425 | | | | | 430 | | | |

| CAC | AAT | GAC | CAG | TCA | CAA | TGG | TTA | CAG | GTG | GAT | CTT | CTT | GTT | CCA | ACC | 1344 |
|---|---|---|---|---|---|---|---|---|---|---|---|---|---|---|---|---|
| His | Asn | Asp | Gln | Ser | Gln | Trp | Leu | Gln | Val | Asp | Leu | Leu | Val | Pro | Thr | |
| | | 435 | | | | | 440 | | | | | 445 | | | | |

| AAA | GTG | ACT | GGC | ATC | ATT | ACA | CAA | GGA | GCT | AAA | GAT | TTT | GGT | CAT | GTA | 1392 |
|---|---|---|---|---|---|---|---|---|---|---|---|---|---|---|---|---|
| Lys | Val | Thr | Gly | Ile | Ile | Thr | Gln | Gly | Ala | Lys | Asp | Phe | Gly | His | Val | |
| | 450 | | | | | 455 | | | | | 460 | | | | | |

| CAG | TTT | GTT | GGC | TCC | TAC | AAA | CTG | GCT | TAC | AGC | AAT | GAT | GGA | GAA | CAC | 1440 |
|---|---|---|---|---|---|---|---|---|---|---|---|---|---|---|---|---|
| Gln | Phe | Val | Gly | Ser | Tyr | Lys | Leu | Ala | Tyr | Ser | Asn | Asp | Gly | Glu | His | |
| 465 | | | | | 470 | | | | | 475 | | | | | 480 | |

| TGG | ACT | GTA | TAC | CAG | GAT | GAA | AAG | CAA | AGA | AAA | GAT | AAG | GTT | TTC | CAG | 1488 |
|---|---|---|---|---|---|---|---|---|---|---|---|---|---|---|---|---|
| Trp | Thr | Val | Tyr | Gln | Asp | Glu | Lys | Gln | Arg | Lys | Asp | Lys | Val | Phe | Gln | |
| | | | | 485 | | | | | 490 | | | | | 495 | | |

| GGA | AAT | TTT | GAC | AAT | GAC | ACT | CAC | AGA | AAA | AAT | GTC | ATC | GAC | CCT | CCC | 1536 |
|---|---|---|---|---|---|---|---|---|---|---|---|---|---|---|---|---|
| Gly | Asn | Phe | Asp | Asn | Asp | Thr | His | Arg | Lys | Asn | Val | Ile | Asp | Pro | Pro | |
| | | | 500 | | | | | 505 | | | | | 510 | | | |

| ATC | TAT | GCA | CGA | CAC | ATA | AGA | ATC | CTT | CCT | TGG | TCC | TGG | TAC | GGG | AGG | 1584 |
|---|---|---|---|---|---|---|---|---|---|---|---|---|---|---|---|---|
| Ile | Tyr | Ala | Arg | His | Ile | Arg | Ile | Leu | Pro | Trp | Ser | Trp | Tyr | Gly | Arg | |
| | | 515 | | | | | 520 | | | | | 525 | | | | |

| ATC | ACA | TTG | GCG | TCA | GAG | CTG | CTG | GGC | TGC | ACA | GAG | GAG | GAA | TGA | GGG | 1632 |
|---|---|---|---|---|---|---|---|---|---|---|---|---|---|---|---|---|
| Ile | Thr | Leu | Ala | Ser | Glu | Leu | Leu | Gly | Cys | Thr | Glu | Glu | Glu | * | Gly | |
| | 530 | | | | | 535 | | | | | 540 | | | | | |

| GAG | GCT | ACA | TTT | CAC | AAC | CGT | CTT | CCC | TAT | TTG | GGT | AAA | AGT | ATC | TCC | 1680 |
|---|---|---|---|---|---|---|---|---|---|---|---|---|---|---|---|---|
| Glu | Ala | Thr | Phe | His | Asn | Arg | Leu | Pro | Tyr | Leu | Gly | Lys | Ser | Ile | Ser | |
| 545 | | | | | 550 | | | | | 555 | | | | | 560 | |

| ATG | GAA | TGA | ACT | GTG | TAA | AAT | CTG | TAG | GAA | ACT | GAA | TGG | TTT | TTT | TTT | 1728 |
|---|---|---|---|---|---|---|---|---|---|---|---|---|---|---|---|---|
| Met | Glu | * | Thr | Val | * | Asn | Leu | * | Glu | Thr | Glu | Trp | Phe | Phe | Phe | |
| | | | | 565 | | | | | 570 | | | | | 575 | | |

| TTT | TCA | TGA | AAA | AGT | GGT | CAA | ATT | ATG | GTA | GGC | AAC | TAA | CGG | TGT | TTT | 1776 |
|---|---|---|---|---|---|---|---|---|---|---|---|---|---|---|---|---|
| Phe | Ser | * | Lys | Ser | Gly | Gln | Ile | Met | Val | Gly | Asn | * | Arg | Cys | Phe | |
| | | 580 | | | | | 585 | | | | | 590 | | | | |

| TAC | C | | | | | | | | | | | | | | | 1780 |
|---|---|---|---|---|---|---|---|---|---|---|---|---|---|---|---|---|
| Tyr | | | | | | | | | | | | | | | | |

( 2 ) INFORMATION FOR SEQ ID NO:12:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

Ser  Pro  Leu  Ser  Pro  Ser  Pro  Arg  Ile  Cys  Leu  Thr  Lys  Arg
       1                 5                10             14

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
            Gly  Lys  Arg  Thr  Ser  Ser
            1                   5
```

(2) INFORMATION FOR SEQ ID NO:14:

(i) SEQUENCE CHARACTERISTICS:
      (A) LENGTH: 513 amino acids
      (B) TYPE: amino acid
      (C) STRANDEDNESS: unknown
      (D) TOPOLOGY: linear (ii) MOLECULE TYPE: protein (xi) SEQUENCE DESCRIPTION: SEQ ID NO:14:

```
Gly  Arg  Ser  Leu  Leu  Leu  Pro  Cys  Ala  Ala  Thr  Ser  Ala  Thr  Leu  Pro
1                   5                        10                       15

Ser  Ala  Thr  Thr  Pro  Asp  Gln  Pro  Gly  Ser  Arg  Pro  Gly  Asp  Gly  Ile
                    20                  25                       30

Met  Lys  Arg  Ser  Val  Ala  Val  Trp  Leu  Leu  Val  Gly  Leu  Ser  Leu  Gly
               35                       40                  45

Val  Pro  Gln  Phe  Gly  Lys  Gly  Asp  Ile  Cys  Asp  Pro  Asn  Pro  Cys  Glu
          50                       55                  60

Asn  Gly  Gly  Ile  Cys  Leu  Pro  Gly  Leu  Ala  Val  Gly  Ser  Phe  Ser  Cys
65                       70                  75                            80

Glu  Cys  Pro  Asp  Gly  Phe  Thr  Asp  Pro  Asn  Cys  Ser  Ser  Val  Val  Glu
               85                       90                       95

Val  Ala  Ser  Asp  Glu  Glu  Pro  Thr  Ser  Ala  Gly  Pro  Cys  Thr  Pro
               100                      105                      110

Asn  Pro  Cys  His  Asn  Gly  Gly  Thr  Cys  Glu  Ile  Ser  Glu  Ala  Tyr  Arg
               115                      120                      125

Gly  Asp  Thr  Phe  Ile  Gly  Tyr  Val  Cys  Lys  Cys  Pro  Arg  Gly  Phe  Asn
     130                      135                      140

Gly  Ile  His  Cys  Gln  His  Asn  Ile  Asn  Glu  Cys  Glu  Val  Glu  Pro  Cys
145                      150                      155                      160

Lys  Asn  Gly  Gly  Ile  Cys  Thr  Asp  Leu  Val  Ala  Asn  Tyr  Ser  Cys  Glu
                    165                      170                      175

Cys  Pro  Gly  Glu  Phe  Met  Gly  Arg  Asn  Cys  Gln  Tyr  Lys  Cys  Ser  Gly
               180                      185                      190

Pro  Leu  Gly  Ile  Glu  Gly  Gly  Ile  Ile  Ser  Asn  Gln  Ile  Thr  Ala
               195                      200                      205

Ser  Ser  Thr  His  Arg  Ala  Leu  Phe  Gly  Leu  Gln  Lys  Trp  Tyr  Pro  Tyr
     210                      215                      220

Tyr  Ala  Arg  Leu  Asn  Lys  Lys  Gly  Leu  Ile  Asn  Ala  Trp  Thr  Ala  Ala
225                      230                      235                      240

Glu  Asn  Asp  Arg  Trp  Lys  Arg  Trp  Ile  Gln  Ile  Asn  Leu  Gln  Arg  Lys
               245                      250                      255

Met  Arg  Val  Thr  Gly  Val  Ile  Thr  Gln  Gly  Ala  Lys  Arg  Ile  Gly  Ser
               260                      265                      270

Pro  Glu  Tyr  Ile  Lys  Phe  Tyr  Lys  Ile  Ala  Tyr  Ser  Asn  Asp  Gly  Lys
               275                      280                      285

Thr  Trp  Ala  Met  Tyr  Lys  Val  Lys  Gly  Thr  Asn  Glu  Asp  Met  Val  Phe
     290                      295                      300

Arg  Gly  Asn  Ile  Asp  Asn  Asn  Thr  Pro  Tyr  Ala  Asn  Ser  Phe  Thr  Pro
305                      310                      315                      320

Pro  Ile  Lys  Ala  Gln  Tyr  Val  Arg  Leu  Tyr  Pro  Gln  Val  Cys  Arg  Arg
                    325                      330                      335
```

```
                His  Cys  Thr  Leu  Arg  Met  Glu  Leu  Leu  Gly  Cys  Glu  Leu  Ser  Gly  Cys
                               340                     345                          350

Ser  Glu  Pro  Leu  Gly  Met  Lys  Ser  Gly  His  Ile  Gln  Asp  Tyr  Gln  Ile
                          355                     360                     365

Thr  Ala  Ser  Ser  Ile  Phe  Arg  Thr  Leu  Asn  Met  Asp  Met  Phe  Thr  Trp
                     370                          375                     380

Glu  Pro  Arg  Lys  Ala  Arg  Leu  Asp  Lys  Gln  Gly  Lys  Val  Asn  Ala  Trp
                385                     390                     395                          400

Thr  Ser  Gly  His  Asn  Asp  Gln  Ser  Gln  Trp  Leu  Gln  Val  Asp  Leu  Leu
                               405                     410                          415

Val  Pro  Thr  Lys  Val  Thr  Gly  Ile  Ile  Thr  Gln  Gly  Ala  Lys  Asp  Phe
                               420                     425                          430

Gly  His  Val  Gln  Phe  Val  Gly  Ser  Tyr  Lys  Leu  Ala  Tyr  Ser  Asn  Asp
                          435                     440                          445

Gly  Glu  His  Trp  Thr  Val  Tyr  Gln  Asp  Glu  Lys  Gln  Arg  Lys  Asp  Lys
                     450                          455                     460

Val  Phe  Gln  Gly  Asn  Phe  Asp  Asn  Asp  Thr  His  Arg  Lys  Asn  Val  Ile
                465                          470                     475                     480

Asp  Pro  Pro  Ile  Tyr  Ala  Arg  His  Ile  Arg  Ile  Leu  Pro  Trp  Ser  Trp
                                    485                     490                          495

Tyr  Gly  Arg  Ile  Thr  Leu  Ala  Ser  Glu  Leu  Leu  Gly  Cys  Thr  Glu  Glu
                                    500                     505                          510

Glu
```

( 2 ) INFORMATION FOR SEQ ID NO:15:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
                Gly  Glu  Ala  Thr  Phe  His  Asn  Arg  Leu  Pro  Tyr  Leu  Gly  Lys  Ser  Ile
                1                   5                        10                         15

Ser  Met  Glu
```

( 2 ) INFORMATION FOR SEQ ID NO:16:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
                Glu  Thr  Glu  Trp  Phe  Phe  Phe  Phe  Ser
                1                   5
```

( 2 ) INFORMATION FOR SEQ ID NO:17:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
                Lys  Ser  Gly  Gln  Ile  Met  Val  Gly  Asn
```

(2) INFORMATION FOR SEQ ID NO:18:

(i) SEQUENCE CHARACTERISTICS:
    (A) LENGTH: 4 amino acids
    (B) TYPE: amino acid
    (D) TOPOLOGY: linear (ii) MOLECULE TYPE: protein (xi) SEQUENCE DESCRIPTION: SEQ ID NO:18:

```
Arg  Cys  Phe  Tyr
 1
```

(2) INFORMATION FOR SEQ ID NO:19:

(i) SEQUENCE CHARACTERISTICS:
    (A) LENGTH: 318 base pairs
    (B) TYPE: nucleic acid
    (C) STRANDEDNESS: single
    (D) TOPOLOGY: unknown (ii) MOLECULE TYPE: DNA (genomic)

(xi) SEQUENCE DESCRIPTION: SEQ ID NO:19:

```
GACAGATGGC  CATGGATTCA  GATAAATTTG  CAAAGAAAAA  TGAGAGTCAC  TGGTGTTATT      60
ACCCAAGGAG  CAAAAAGGAT  TGGAAGCCCA  GAGTACATAA  AATCCTACAA  AATTGCCTAC     120
AGCAATGACG  GGAAGACCTG  GGCAATGTAC  AAAGTAAAAG  GCACCAATGA  AGAGATGGTC     180
TTTCGTGGAA  ATGTTGATAA  CAACACACCA  TATGCTAATT  CTTTCACACC  CCCAATCAAA     240
GCTCAGTATG  TAAGACTCTA  CCCCCAAATT  TGTCGAAGGC  ATTGTACTTT  AAGAATGGAA     300
CTTCTTGGCT  GTGAGCTC                                                       318
```

(2) INFORMATION FOR SEQ ID NO:20:

(i) SEQUENCE CHARACTERISTICS:
    (A) LENGTH: 320 amino acids
    (B) TYPE: amino acid
    (C) STRANDEDNESS:
    (D) TOPOLOGY: unknown (ii) MOLECULE TYPE: protein (xi) SEQUENCE DESCRIPTION: SEQ ID NO:20:

```
Cys  Ser  Thr  Gln  Leu  Gly  Met  Glu  Gly  Gly  Ala  Ile  Ala  Asp  Ser  Gln
 1                    5                        10                       15

Ile  Ser  Ala  Ser  Tyr  Val  Tyr  Met  Gly  Phe  Met  Gly  Leu  Gln  Arg  Trp
                      20                        25                       30

Gly  Pro  Glu  Leu  Ala  Arg  Leu  Tyr  Arg  Thr  Gly  Ile  Val  Asn  Ala  Trp
                35                        40                       45

His  Ala  Ser  Asn  Tyr  Asp  Xaa  Ser  Lys  Pro  Trp  Ile  Gln  Val  Asn  Leu
           50                        55                       60

Leu  Arg  Lys  Met  Arg  Val  Ser  Gly  Val  Met  Thr  Gln  Gly  Ala  Ser  Arg
 65                        70                        75                       80

Ala  Gly  Arg  Ala  Glu  Tyr  Leu  Lys  Thr  Phe  Lys  Val  Ala  Tyr  Ser  Leu
                      85                        90                       95

Asp  Gly  Xaa  Arg  Lys  Phe  Glu  Phe  Ile  Gln  Asp  Glu  Ser  Gly  Gly  Asp
                100                       105                      110

Lys  Glu  Phe  Leu  Gly  Asn  Leu  Asp  Asn  Asn  Ser  Leu  Lys  Val  Asn  Met
                115                       120                      125

Phe  Asn  Pro  Thr  Leu  Glu  Ala  Gln  Tyr  Ile  Arg  Leu  Tyr  Pro  Val  Ser
```

|     |     |     | 130 |     |     |     |     | 135 |     |     |     |     | 140 |     |
| --- | --- | --- | --- | --- | --- | --- | --- | --- | --- | --- | --- | --- | --- | --- |
| Cys 145 | His | Arg | Gly | Cys | Thr 150 | Leu | Arg | Phe | Glu | Leu 155 | Leu | Gly | Cys | Glu | Leu 160 |
| His | Gly | Cys | Leu | Glu 165 | Pro | Leu | Gly | Leu | Lys 170 | Asn | Asn | Thr | Ile | Pro 175 | Asp |
| Ser | Gln | Met | Ser 180 | Ala | Ser | Ser | Ser | Tyr 185 | Lys | Thr | Trp | Asn | Leu 190 | Arg | Ala |
| Phe | Gly | Trp 195 | Tyr | Pro | His | Leu | Gly 200 | Arg | Leu | Asp | Asn | Gly 205 | Lys | Ile |
| Asn | Ala | Trp 210 | Thr | Ala | Gln | Ser 215 | Asn | Ser | Ala | Lys | Glu 220 | Trp | Leu | Gln | Val |
| Asp 225 | Leu | Gly | Thr | Gln | Arg 230 | Gln | Val | Thr | Gly | Ile 235 | Ile | Thr | Gln | Gly | Ala 240 |
| Arg | Asp | Phe | Gly | His 245 | Ile | Gln | Tyr | Val | Glu 250 | Ser | Tyr | Lys | Val | Ala 255 | His |
| Ser | Asp | Asp | Gly 260 | Val | Gln | Trp | Thr | Val 265 | Tyr | Xaa | Xaa | Glu | Glu 270 | Gly |
| Ser | Ser | Lys 275 | Val | Phe | Gln | Gly | Asn 280 | Leu | Asp | Asn | Ser | His 285 | Lys | Lys |
| Asn | Ile 290 | Phe | Glu | Lys | Pro | Phe 295 | Met | Ala | Arg | Tyr | Val 300 | Arg | Val | Leu | Pro |
| Val 305 | Ser | Trp | His | Asn | Arg 310 | Ile | Thr | Leu | Arg | Leu 315 | Glu | Leu | Leu | Gly | Cys 320 |

( 2 ) INFORMATION FOR SEQ ID NO:21:

( i ) SEQUENCE CHARACTERISTICS:
        ( A ) LENGTH: 321 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:21:

| Cys 1 | Ser | Gly | Pro | Leu 5 | Gly | Ile | Glu | Gly | Ile 10 | Ile | Ser | Asn | Gln 15 | Gln |
| --- | --- | --- | --- | --- | --- | --- | --- | --- | --- | --- | --- | --- | --- | --- |
| Ile | Thr | Ala | Ser 20 | Ser | Thr | His | Arg | Ala 25 | Leu | Phe | Gly | Leu | Gln 30 | Lys | Trp |
| Tyr | Pro | Tyr 35 | Tyr | Ala | Arg | Leu | Asn 40 | Lys | Lys | Gly | Leu | Ile 45 | Asn | Ala | Trp |
| Thr | Ala 50 | Ala | Glu | Asn | Asp | Arg 55 | Trp | Asn | Arg | Trp | Ile 60 | Gln | Ile | Asn | Leu |
| Gln 65 | Arg | Lys | Met | Arg | Val 70 | Thr | Gly | Val | Ile | Thr 75 | Gln | Gly | Ala | Lys | Arg 80 |
| Ile | Gly | Ser | Pro | Glu 85 | Tyr | Ile | Lys | Phe | Tyr 90 | Lys | Ile | Ala | Tyr | Ser 95 | Asn |
| Asp | Gly | Lys | Thr 100 | Trp | Ala | Met | Tyr | Lys 105 | Val | Lys | Gly | Thr | Asn 110 | Glu | Asp |
| Met | Val | Phe 115 | Arg | Gly | Asn | Ile | Asp 120 | Asn | Asn | Thr | Pro | Tyr 125 | Ala | Asn | Ser |
| Phe | Thr 130 | Pro | Pro | Ile | Lys | Ala 135 | Gln | Tyr | Val | Arg | Leu 140 | Tyr | Pro | Gln | Val |
| Cys 145 | Arg | Arg | His | Cys | Thr 150 | Leu | Arg | Met | Glu | Leu 155 | Leu | Gly | Cys | Glu | Leu 160 |
| Ser | Gly | Cys | Ser | Glu 165 | Pro | Leu | Gly | Met | Lys 170 | Ser | Gly | His | Ile | Gln 175 | Asp |

```
        Tyr   Gln   Ile   Thr   Ala   Ser   Ser   Ile   Phe   Arg   Thr   Leu   Asn   Met   Asp   Met
                          180                            185                             190

Phe   Thr   Trp   Glu   Pro   Arg   Lys   Ala   Arg   Leu   Asp   Lys   Gln   Gly   Lys   Val
                    195                     200                           205

Asn   Ala   Trp   Thr   Ser   Gly   His   Asn   Asp   Gln   Ser   Gln   Trp   Leu   Gln   Val
              210                           215                     220

Xaa   Leu   Leu   Val   Pro   Thr   Lys   Val   Thr   Gly   Ile   Ile   Thr   Gln   Gly   Ala
        225                           230                     235                                 240

Lys   Asp   Xaa   Gly   His   Val   Gln   Phe   Val   Gly   Ser   Tyr   Lys   Leu   Ala   Tyr
                                245                           250                           255

Ser   Asn   Asp   Gly   Glu   His   Trp   Thr   Val   Xaa   Gln   Asp   Glu   Lys   Gln   Arg
                          260                           265                           270

Lys   Asp   Lys   Val   Xaa   Gln   Gly   Asn   Phe   Asp   Asn   Asp   Thr   His   Arg   Lys
                    275                           280                           285

Asn   Val   Ile   Asp   Pro   Pro   Ile   Tyr   Ala   Arg   His   Ile   Arg   Ile   Leu   Pro
                    290                           295                           300

Trp   Ser   Trp   Tyr   Gly   Arg   Ile   Thr   Leu   Ala   Ser   Glu   Leu   Leu   Gly   Cys
        305                           310                           315                           320

Thr
```

( 2 ) INFORMATION FOR SEQ ID NO:22:

( i ) SEQUENCE CHARACTERISTICS:
        ( A ) LENGTH: 25 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:22:

```
        Met   Lys   Arg   Ser   Val   Ala   Val   Trp   Leu   Leu   Val   Gly   Leu   Ser   Leu   Gly
        1                       5                             10                            15

Val   Pro   Gln   Phe   Gly   Lys   Gly   Asp   Ile
                          20                      25
```

( 2 ) INFORMATION FOR SEQ ID NO:23:

( i ) SEQUENCE CHARACTERISTICS:
        ( A ) LENGTH: 57 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:23:

```
        Cys   Asp   Pro   Asn   Pro   Cys   Glu   Asn   Gly   Gly   Ile   Cys   Leu   Pro   Gly   Leu
        1                       5                             10                            15

Ala   Val   Gly   Xaa   Xaa   Xaa   Xaa   Xaa   Ser   Phe   Ser   Cys   Glu   Cys   Pro   Asp
                          20                            25                            30

Gly   Phe   Thr   Asp   Pro   Asn   Cys   Ser   Ser   Val   Val   Glu   Val   Ala   Ser   Asp
                    35                            40                            45

Glu   Glu   Glu   Pro   Thr   Ser   Ala   Gly   Pro
                    50                            55
```

( 2 ) INFORMATION FOR SEQ ID NO:24:

( i ) SEQUENCE CHARACTERISTICS:
        ( A ) LENGTH: 43 amino acids
        ( B ) TYPE: amino acid (C) STRANDEDNESS:
(D) TOPOLOGY: unknown (ii) MOLECULE TYPE: peptide (xi) SEQUENCE DESCRIPTION: SEQ ID NO:24:

| Cys | Thr | Pro | Asn | Pro | Cys | His | Asn | Gly | Gly | Thr | Cys | Glu | Ile | Ser | Glu |
|---|---|---|---|---|---|---|---|---|---|---|---|---|---|---|---|
| 1 | | | | 5 | | | | | 10 | | | | | 15 | |

| Ala | Tyr | Arg | Gly | Asp | Thr | Phe | Ile | Gly | Tyr | Val | Cys | Lys | Cys | Pro | Arg |
|---|---|---|---|---|---|---|---|---|---|---|---|---|---|---|---|
| | | | 20 | | | | | 25 | | | | | 30 | | |

| Gly | Phe | Asn | Gly | Ile | His | Cys | Gln | His | Asn | Ile |
|---|---|---|---|---|---|---|---|---|---|---|
| | | | 35 | | | | 40 | | | |

(2) INFORMATION FOR SEQ ID NO:25:

(i) SEQUENCE CHARACTERISTICS:
(A) LENGTH: 42 amino acids
(B) TYPE: amino acid
(C) STRANDEDNESS:
(D) TOPOLOGY: unknown (ii) MOLECULE TYPE: peptide (xi) SEQUENCE DESCRIPTION: SEQ ID NO:25:

| Cys | Glu | Val | Glu | Pro | Cys | Lys | Asn | Gly | Gly | Ile | Cys | Thr | Asp | Leu | Val |
|---|---|---|---|---|---|---|---|---|---|---|---|---|---|---|---|
| 1 | | | | 5 | | | | | 10 | | | | | 15 | |

| Ala | Xaa | Xaa | Xaa | Xaa | Xaa | Xaa | Xaa | Asn | Tyr | Ser | Cys | Glu | Cys | Pro | Gly |
|---|---|---|---|---|---|---|---|---|---|---|---|---|---|---|---|
| | | | 20 | | | | | 25 | | | | | 30 | | |

| Glu | Phe | Met | Gly | Arg | Asn | Cys | Gln | Tyr | Lys |
|---|---|---|---|---|---|---|---|---|---|
| | | 35 | | | | | 40 | | |

(2) INFORMATION FOR SEQ ID NO:26:

(i) SEQUENCE CHARACTERISTICS:
(A) LENGTH: 40 amino acids
(B) TYPE: amino acid
(C) STRANDEDNESS:
(D) TOPOLOGY: unknown (ii) MOLECULE TYPE: peptide (xi) SEQUENCE DESCRIPTION: SEQ ID NO:26:

| Cys | Xaa | Xaa | Xaa | Pro | Cys | Xaa | Asn | Gly | Gly | Xaa | Cys | Xaa | Xaa | Xaa | Xaa |
|---|---|---|---|---|---|---|---|---|---|---|---|---|---|---|---|
| 1 | | | | 5 | | | | | 10 | | | | | 15 | |

| Xaa | Xaa | Xaa | Xaa | Xaa | Xaa | Xaa | Xaa | Xaa | Tyr | Xaa | Cys | Xaa | Cys | Xaa | Xaa |
|---|---|---|---|---|---|---|---|---|---|---|---|---|---|---|---|
| | | | 20 | | | | | 25 | | | | | 30 | | |

| Gly | Tyr | Xaa | Gly | Xaa | Xaa | Cys | Xaa |
|---|---|---|---|---|---|---|---|
| | | | 35 | | | | 40 |

(2) INFORMATION FOR SEQ ID NO:27:

(i) SEQUENCE CHARACTERISTICS:
(A) LENGTH: 310 base pairs
(B) TYPE: nucleic acid
(C) STRANDEDNESS: single
(D) TOPOLOGY: unknown (ii) MOLECULE TYPE: DNA (genomic)

(ix) FEATURE:
(A) NAME/KEY: CDS
(B) LOCATION: 1..309

(xi) SEQUENCE DESCRIPTION: SEQ ID NO:27:

| NGTGATATTT | GTGATCCCAA | TCCATGTGAA | AATGGAGGTA | TCTGTTTGCC | AGGATTGGCT | 60 |
|---|---|---|---|---|---|---|
| GTAGGTTCCT | TTTCCTGTGA | GTGTCCAGAT | GGCTTCACAG | ACCCCAACTG | TTCTAGTGTT | 120 |

| | | | | | |
|---|---|---|---|---|---|
| GTGGAGGTTG | GTCCCTGCAC | TCCTAATCCA | TGCCATAATG | GAGGAACCTG | TGAAATAAGT | 180 |
| GAAGCATACC | GAGGGGATAC | ATTCATAGGC | TATGTTTGTA | AATGTCCCCG | AGGATTTAAT | 240 |
| GGGATTCACT | GTCAGCACAA | CATAAATGAA | TGCGAAGTTG | AGCCTTGCAA | AAATGGTGGA | 300 |
| ATATGTACAG | | | | | | 310 |

( 2 ) INFORMATION FOR SEQ ID NO:28:

( i ) SEQUENCE CHARACTERISTICS:
        ( A ) LENGTH: 2308 base pairs
        ( B ) TYPE: nucleic acid
        ( C ) STRANDEDNESS: single
        ( D ) TOPOLOGY: linear ( i x ) FEATURE:
        ( A ) NAME/KEY: Coding Sequence
        ( B ) LOCATION: 550...1212
        ( D ) OTHER INFORMATION:

( x i ) SEQUENCE DESCRIPTION: SEQ ID NO:28:

| | | | | | |
|---|---|---|---|---|---|
| GAATTCCGGG | AGGGAGGGTA | GGGGGGCGGG | CCGCGGGGGC | CCAAAGCCAG | CTAGGCTCAG | 60 |
| TCTCACACGC | GCGCCGCCAC | TGTTTGTATA | TAGTGCGCTC | CTGGCCTCAG | GCTCGCTCCC | 120 |
| CTCCAGCTCT | CGCTTCATTG | TTCTCCAAGT | CAGAAGCCCC | CGCATCCGCC | GCGCAGCAGC | 180 |
| GTGAGCCGTA | GTCACTGCTG | GCCGCTTCGC | CTGCGTGCGC | GCACGGAAAT | CGGGGAGCCA | 240 |
| GGAACCCAAG | GAGCCGCCGT | CCGCCCGCTG | TGCCTCTGCT | AGACCACTCG | CAGCCCCAGC | 300 |
| CTCTCTCAAG | CGCACCCACC | TCCGCGCACC | CCAGCTCAGG | CGAAGCTGGA | GTGAGGGTGA | 360 |
| ATCACCCTTT | CTCTAGGGCC | ACCACTCTTT | TATCGCCCTT | CCCAAGATTT | GAGAAGCGCT | 420 |
| GCGGGAGGAA | AGACGTCCTC | TTGATCTCTG | ACAGGGCGGG | GTTTACTGCT | GTCCTGCAGG | 480 |
| CGCGCCTCGC | CTACTGTGCC | CTCCGCTACG | ACCCCGGACC | AGCCCAGGTC | ACGTCCGTGA | 540 |

| | | | | | | | | | | | | | |
|---|---|---|---|---|---|---|---|---|---|---|---|---|---|
| GAAGGGATC | ATG | AAG | CAC | TTG | GTA | GCA | GCC | TGG | CTT | TTG | GTT | GGA | CTC | AGC | 591 |
| | Met | Lys | His | Leu | Val | Ala | Ala | Trp | Leu | Leu | Val | Gly | Leu | Ser | |
| | 1 | | | | 5 | | | | | 10 | | | | | |

| | | | | | | | | | | | | | |
|---|---|---|---|---|---|---|---|---|---|---|---|---|---|---|
| CTC | GGG | GTG | CCC | CAG | TTC | GGC | AAA | GGT | GAC | ATT | TGC | AAC | CCG | AAC | CCC | 639 |
| Leu | Gly | Val | Pro | Gln | Phe | Gly | Lys | Gly | Asp | Ile | Cys | Asn | Pro | Asn | Pro | |
| 1 5 | | | | | 20 | | | | | 25 | | | | | 30 | |

| | | | | | | | | | | | | | |
|---|---|---|---|---|---|---|---|---|---|---|---|---|---|---|
| TGT | GAA | AAT | GGT | GGC | ATC | TGT | CTG | TCA | GGA | CTG | GCT | GAT | GAT | TCC | TTT | 687 |
| Cys | Glu | Asn | Gly | Gly | Ile | Cys | Leu | Ser | Gly | Leu | Ala | Asp | Asp | Ser | Phe | |
| | | | | 3 5 | | | | | 40 | | | | | 4 5 | | |

| | | | | | | | | | | | | | |
|---|---|---|---|---|---|---|---|---|---|---|---|---|---|---|
| TCC | TGT | GAG | TGT | CCA | GAA | GGC | TTC | GCA | GGT | CCG | AAC | TGC | TCT | AGT | GTT | 735 |
| Ser | Cys | Glu | Cys | Pro | Glu | Gly | Phe | Ala | Gly | Pro | Asn | Cys | Ser | Ser | Val | |
| | | | 50 | | | | | 5 5 | | | | | 60 | | | |

| | | | | | | | | | | | | | |
|---|---|---|---|---|---|---|---|---|---|---|---|---|---|---|
| GTG | GAG | GTT | GCA | TCA | GAT | GAA | GAA | AAG | CCT | ACT | TCA | GCA | GGT | CCC | TGC | 783 |
| Val | Glu | Val | Ala | Ser | Asp | Glu | Glu | Lys | Pro | Thr | Ser | Ala | Gly | Pro | Cys | |
| | | 6 5 | | | | | 70 | | | | | 7 5 | | | | |

| | | | | | | | | | | | | | |
|---|---|---|---|---|---|---|---|---|---|---|---|---|---|---|
| ATC | CCT | AAC | CCA | TGC | CAT | AAC | GGA | GGA | ACC | TGT | GAG | ATA | AGC | GAA | GCC | 831 |
| Ile | Pro | Asn | Pro | Cys | His | Asn | Gly | Gly | Thr | Cys | Glu | Ile | Ser | Glu | Ala | |
| | 80 | | | | | 8 5 | | | | | 90 | | | | | |

| | | | | | | | | | | | | | |
|---|---|---|---|---|---|---|---|---|---|---|---|---|---|---|
| TAT | CGA | GGA | GAC | ACA | TTC | ATA | GGC | TAT | GTT | TGT | AAA | TGT | CCT | CGG | GGA | 879 |
| Tyr | Arg | Gly | Asp | Thr | Phe | Ile | Gly | Tyr | Val | Cys | Lys | Cys | Pro | Arg | Gly | |
| 9 5 | | | | | 100 | | | | | 105 | | | | | 110 | |

| | | | | | | | | | | | | | |
|---|---|---|---|---|---|---|---|---|---|---|---|---|---|---|
| TTT | AAT | GGG | ATT | CAC | TGT | CAG | CAC | AAT | ATA | AAT | GAA | TGT | GAA | GCT | GAG | 927 |
| Phe | Asn | Gly | Ile | His | Cys | Gln | His | Asn | Ile | Asn | Glu | Cys | Glu | Ala | Glu | |
| | | | | 115 | | | | | 120 | | | | | 125 | | |

| | | | | | | | | | | | | | |
|---|---|---|---|---|---|---|---|---|---|---|---|---|---|---|
| CCT | TGC | AGA | AAT | GGC | GGA | ATA | TGT | ACC | GAC | CTT | GTT | GCT | AAC | TAC | TCT | 975 |
| Pro | Cys | Arg | Asn | Gly | Gly | Ile | Cys | Thr | Asp | Leu | Val | Ala | Asn | Tyr | Ser | |
| | | | 130 | | | | | 135 | | | | | 140 | | | |

| | | | | | | | | | | | | | |
|---|---|---|---|---|---|---|---|---|---|---|---|---|---|---|
| TGT | GAA | TGC | CCA | GGA | GAA | TTT | ATG | GGA | CGA | AAT | TGT | CAA | TAT | AAA | TGC | 1023 |

-continued

| | | | | | | | | | | | | | | |
|---|---|---|---|---|---|---|---|---|---|---|---|---|---|---|
| Cys | Glu | Cys | Pro | Gly | Glu | Phe | Met | Gly | Arg | Asn | Cys | Gln | Tyr | Lys | Cys |
| | 145 | | | | 150 | | | | | 155 | | | | |

```
TCT  GGG  CAC  TTG  GGA  ATC  GAA  GGT  GGG  ATC  ATA  TCT  AAT  CAG  CAA  ATC       1071
Ser  Gly  His  Leu  Gly  Ile  Glu  Gly  Gly  Ile  Ile  Ser  Asn  Gln  Gln  Ile
     160                 165                      170

ACA  GCT  TCA  TCT  AAT  CAC  CGA  GCT  CTT  TTT  GGA  CTC  CAG  AAG  TGG  TAT       1119
Thr  Ala  Ser  Ser  Asn  His  Arg  Ala  Leu  Phe  Gly  Leu  Gln  Lys  Trp  Tyr
175                      180                 185                           190

CCC  TAC  TAT  GCT  AGA  CTT  AAT  AAG  AAG  GGC  CTT  ATA  AAT  GCC  TGG  ACA       1167
Pro  Tyr  Tyr  Ala  Arg  Leu  Asn  Lys  Lys  Gly  Leu  Ile  Asn  Ala  Trp  Thr
               195                      200                      205

GCT  GCT  GAA  AAT  GAC  AGA  TGG  CCA  TGG  ATT  CAG  GTA  ACA  GTG  GGA  TGAGA    1217
Ala  Ala  Glu  Asn  Asp  Arg  Trp  Pro  Trp  Ile  Gln  Val  Thr  Val  Gly
               210                      215                 220
```

```
CAAATCCATT  TCCCAAATTA  TCAGAATCAT  TATAGAAGTA  GGTTAGGGAG  AATTGGCTGT    1277
GATTCTTTCT  CATGGTTAAA  ATGTGATTTA  GTTCAGAATT  AACATGGTTG  GAAACTCTAA    1337
AAAATGTGGA  AAACAGGAAC  ATTCTATGTC  TGAAAATCTG  AAAATAGCAT  CAAGATGAAA    1397
ACATTCTTTA  GTCATAAATA  TACTCTTTTA  AGTTATAGTA  GAGAAAAAGA  TCTTATCATT    1457
TCATAAGTGG  ACTTTTGGGA  TAGCATTGGA  AATGTAAATG  AATAAATAC   CTAATTGAAA    1517
AAAGTTTATT  CTAAAGTGTT  AATATTTAGC  AACAGATTCA  GAGACAAGAA  AGTAACAATT    1577
CAATCTGTGT  ATTTTTTGTG  AGAAATAGTT  TCCCATGTGC  AAATATAAAG  TGCGCATCAT    1637
ATCATGATAA  TATCCAACTG  TCTGCAGAAC  TCCCTTTCAT  AAATGAGAGA  ATTTTAATTC    1697
ATAGTGCCTT  ATATCCTCAT  CAGCCATCTG  ACTTTACTAC  AGAAGAAAAC  AATGAAATGA    1757
TGCATTAAGT  GCTTTGCTAG  AAGAAACATC  ATAGCAAAGC  TGATAGCCCA  CATTCTGTGC    1817
ANNNAAGCTT  CCAGAGCACT  CGAGAAAAAG  CAGAAATGAG  ATGTTTTATG  AAAACCGAAA    1877
AGATAATCTG  ATTTCTGTGA  AATATACTTT  TGATCATGTG  GTTCTTTAAG  ATAGTCACTA    1937
ACAAGTCATT  AGTAGCAGAT  ACCAAATGGG  AGAAAATTTC  CAGTATACTG  AGGGTCAAGG    1997
CAGTCATGCT  GAAACTACAT  GAGGTCAGGA  AAGTTTTGAA  ATAAGGTGAT  TTTGGAAGGA    2057
TACCTTCAAC  TGGCCTAGAT  TTTCAAGAAA  CAGTGTAATC  AACAGCCAAA  CATGAGAATC    2117
TAGCTAACAG  CATTTAGAAA  ACCAGAACTA  AGAGTGTTAC  TGGGGAATTG  CATTTAAATC    2177
CAGTATGAGA  GTTTGCAAAT  GCCGTATTCT  TCTAAGGGGT  TTGTGCCACA  TTTTGTTACC    2237
ATGGAGTCCT  CTGTAAGAAC  TTTATTAGAT  AAATCATCTT  TACACTATAA  TTTGAATAAA    2297
AGCCGGAATT  C                                                            2308
```

( 2 ) INFORMATION FOR SEQ ID NO:29:

( i ) SEQUENCE CHARACTERISTICS:
        ( A ) LENGTH: 221 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:29:

```
Met  Lys  His  Leu  Val  Ala  Ala  Trp  Leu  Leu  Val  Gly  Leu  Ser  Leu  Gly
1                   5                   10                      15

Val  Pro  Gln  Phe  Gly  Lys  Gly  Asp  Ile  Cys  Asn  Pro  Asn  Pro  Cys  Glu
               20                  25                  30

Asn  Gly  Gly  Ile  Cys  Leu  Ser  Gly  Leu  Ala  Asp  Asp  Ser  Phe  Ser  Cys
          35                  40                  45
```

-continued

| | | | | | | | | | | | | | | |
|---|---|---|---|---|---|---|---|---|---|---|---|---|---|---|
| Glu | Cys 50 | Pro | Glu | Gly | Phe | Ala 55 | Gly | Pro | Asn | Cys | Ser 60 | Ser | Val | Val | Glu |
| Val 65 | Ala | Ser | Asp | Glu | Glu 70 | Lys | Pro | Thr | Ser | Ala 75 | Gly | Pro | Cys | Ile | Pro 80 |
| Asn | Pro | Cys | His | Asn 85 | Gly | Gly | Thr | Cys | Glu 90 | Ile | Ser | Glu | Ala | Tyr 95 | Arg |
| Gly | Asp | Thr | Phe 100 | Ile | Gly | Tyr | Val | Cys 105 | Lys | Cys | Pro | Arg | Gly 110 | Phe | Asn |
| Gly | Ile | His 115 | Cys | Gln | His | Asn | Ile 120 | Asn | Glu | Cys | Glu | Ala 125 | Glu | Pro | Cys |
| Arg | Asn 130 | Gly | Gly | Ile | Cys | Thr 135 | Asp | Leu | Val | Ala | Asn 140 | Tyr | Ser | Cys | Glu |
| Cys 145 | Pro | Gly | Glu | Phe | Met 150 | Gly | Arg | Asn | Cys | Gln 155 | Tyr | Lys | Cys | Ser | Gly 160 |
| His | Leu | Gly | Ile | Glu 165 | Gly | Gly | Ile | Ile | Ser 170 | Asn | Gln | Gln | Ile | Thr 175 | Ala |
| Ser | Ser | Asn | His 180 | Arg | Ala | Leu | Phe | Gly 185 | Leu | Gln | Lys | Trp | Tyr 190 | Pro | Tyr |
| Tyr | Ala | Ala 195 | Leu | Asn | Lys | Lys | Gly 200 | Leu | Ile | Asn | Ala | Trp 205 | Thr | Ala | Ala |
| Glu | Asn 210 | Asp | Arg | Trp | Pro | Trp 215 | Ile | Gln | Val | Thr | Val 220 | Gly | | | |